(12) United States Patent
Klueh et al.

(10) Patent No.: US 11,554,160 B2
(45) Date of Patent: *Jan. 17, 2023

(54) SYSTEMS, METHODS AND PRODUCTS FOR MINIMIZING TISSUE REACTIONS AND TISSUE INJURY AT AN INFUSION SITE

(71) Applicant: Cell and Molecular Tissue Engineering, LLC, Avon, CT (US)

(72) Inventors: Ulrike W. Klueh, Detroit, MI (US); Donald L. Kreutzer, Avon, CT (US)

(73) Assignee: Cell and Molecular Tissue Engineering, LLC, Avon, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/083,989

(22) Filed: Oct. 29, 2020

(65) Prior Publication Data

US 2021/0113666 A1    Apr. 22, 2021

Related U.S. Application Data

(63) Continuation of application No. 16/092,566, filed as application No. PCT/US2017/027146 on Apr. 12, 2017, now Pat. No. 10,821,156.

(60) Provisional application No. 62/321,523, filed on Apr. 12, 2016, provisional application No. 62/321,597, filed on Apr. 12, 2016.

(51) Int. Cl.

| *A61K 38/28* | (2006.01) |
| *A61K 9/00* | (2006.01) |
| *A61K 47/40* | (2006.01) |
| *A61M 5/158* | (2006.01) |
| *C07K 14/62* | (2006.01) |
| *A61P 3/10* | (2006.01) |
| *A61P 29/00* | (2006.01) |

(52) U.S. Cl.
CPC ............ *A61K 38/28* (2013.01); *A61K 9/0019* (2013.01); *A61K 47/40* (2013.01); *A61M 5/1582* (2013.01); *A61P 3/10* (2018.01); *A61P 29/00* (2018.01); *C07K 14/62* (2013.01)

(58) Field of Classification Search
CPC ...... A61K 38/28; A61K 9/0019; A61K 47/40; A61M 5/1582; C07K 14/62
See application file for complete search history.

(56) References Cited

U.S. PATENT DOCUMENTS

| 10,821,156 B2* | 11/2020 | Klueh ................ A61M 5/1582 |
| 2003/0118510 A1‡ | 6/2003 | Patton ....................... A61P 3/08 424/45 |
| 2007/0207189 A1‡ | 9/2007 | Belcheva ................ A61L 27/54 424/44 |
| 2010/0120660 A1‡ | 5/2010 | Balschmidt ............... A61P 3/10 514/1 |
| 2010/0210506 A1‡ | 8/2010 | Quay ................... A61K 9/0043 514/1 |
| 2011/0104069 A1‡ | 5/2011 | Xu .......................... A61P 29/00 424/9 |
| 2011/0144585 A1‡ | 6/2011 | Bianchi ............. A61M 5/14244 604/12 |
| 2011/0171140 A1‡ | 7/2011 | Illum ....................... A61P 1/08 424/43 |
| 2013/0022592 A1‡ | 1/2013 | Vaughn .................. A61K 38/47 424/94 |
| 2014/0262879 A1‡ | 9/2014 | Klueh ................ A61B 5/14532 206/363 |
| 2015/0051141 A9* | 2/2015 | Shandler ................... A61P 3/08 530/308 |
| 2015/0112302 A1‡ | 4/2015 | Chattaraj .......... A61M 5/14248 604/50 |
| 2019/0054233 A1‡ | 2/2019 | Demaria ................ B01J 20/264 |

FOREIGN PATENT DOCUMENTS

| GB | 2173503 | ‡ 10/1986 |
| GB | 2173503 A | 10/1986 |
| WO | 2012065996 A1 | 5/2012 |
| WO | WO-2012065996 A1 ‡ | 5/2012 ................ A61P 3/10 |

OTHER PUBLICATIONS

Chen et al, The adsorption of phenol, m-cresol and m-catechol on β-Cyclodextrin derivative-grafted chitosan and the removal of phenols from industrial wastewater, Adsorption science and technology vol. 24, No. 7, 2006. (Year: 2006).*

Zhang, Liefeng et al., "Effects of Hydroxypropyl-β-Cyclodextrin on in Vitro Insulin Stability," Int. J. Mol. Sci, 10, 2031-40 (2009).‡

International Search Report and Written Opinion dated Jul. 17, 2017 (PCT/US2017/027146).‡

Brewster, Marcus E. et al., "Use of 2-Hydroxypropyl-β-cyclodextrin as a Solubilizing and Stabilizing Excipient for Protein Drugs," Pharmaceutical Research, vol. 8, No. 6, 792-5 (1991).‡

Kitagawa, Keisuke et al., "Inhibition of insulin amyloid fibril formation by cyclodextrins," Amyloid, vol. 22, No. 3, p. 181-186, Jul. 3, 2015.‡

Supplementary Partial European Search Report dated Nov. 12, 2019 (European Patent Application No. 17783033.8).‡

Oliveri, Valentina et al., "Cyclodextrins as Protective Agents of Protein Aggregation: An Overview," Chemistry—An Asian Journal, vol. 11, No. 11, p. 1648-1657, Apr. 2, 2016.‡

(Continued)

*Primary Examiner* — Mina Haghighatian

(74) *Attorney, Agent, or Firm* — Alix, Yale & Ristas, LLP

(57) ABSTRACT

Products, systems and methods are disclosed for lowering the concentrations of at least one of preservatives and fibrils in a liquid insulin composition. One method comprises replacing at least a portion of at least one of phenol and m-cresol with at least one of cyclodextrins, cyclodextrin polymers, cyclodextrin beads, and an ion exchange resin.

15 Claims, 64 Drawing Sheets

(56) References Cited

OTHER PUBLICATIONS

Banga, A. K. et al., "Minimization of Shaking-induced Formation of Insoluble Aggregates of Insulin by Cyclodextrins," Journal of Drug Targeting, vol. 1, No. 4, p. 341-345, Jan. 20, 1993.‡
Al-Tabakha, M. M. et al., "Recent Challenges in Insulin Delivery Systems: A Review," Indian Journal of Pharmaceutical Sciences, vol. 70, No. 3, p. 278-286, Jan. 1, 2008.‡

\* cited by examiner
‡ imported from a related application

IMPACT EXCIPIENTS/DILUENTS ON PBMC

Cytokines induced in PBMC's by diluent:

TNFa, IL-1B and IL-1a and IL-6

(pro-inflammatory cytokines)

Chemokines induced in PBMC's by diluent:

IL-8 (pro-inflammatory chemokine)

Cytokines NOT induced in PBMC's by diluent:

IL-2, IL-4 and IL-10 (anti-inflammatory)

H&E stained mouse skin and SC tissue sections after three-day infusion via an implanted polymer SC infusion catheter of [top] saline (control) and [middle] insulin diluent in normal mice, and [bottom] insulin infusion in a NOD diabetic mouse.

SALINE INFUSION OVER 3 DAYS

DILUENT INFUSION OVER 3 DAYS

INSULIN INFUSION IN A DIABETIC MOUSE OVER 3 DAYS

Leukocyte influx into murine air pouch after infusion of insulin, diluent or saline in normal mice Leukocyte influx into murine air pouch after infusion of insulin, diluent or saline in diabetic mice

HISTOLOGICAL EVALUATION AT AIR POUCH INFUSION SITE

SALINE INFUSION — EXCIPIENT INFUSION

UPTAKE OF FITC-INSULIN BY PBMCs *IN VITRO*

IMPACT OF LEUKOCYTE PROTEASE ON INSULIN

IMPACT OF ANTI-PROTEASES ON FITC INSULIN DEGRADATION

| INHIBITORS | DOES INHIBITOR BLOCK FITC-INSULIN/INSULIN DEGRADATION? | | | |
|---|---|---|---|---|
| | PROTEASES | | | |
| | Elastase | Trypsin | IDE | WBC Extract |
| Aprotinin | Yes | Yes | No | Yes |
| AAT | Yes | Yes | No | Yes |
| SP16 | Yes | Yes | No | Yes |
| HALT | Yes | Yes | Yes | Yes |
| HALT + EDTA | Yes | Yes | Yes | Yes |
| Pepstatin A | No | No | No | +/- |

<u>HALT</u> = AEBSF HCl, Aprotinin, Bestatin, E-64, Leupeptin and Pepstatin A
<u>Other protease targets</u>: Cathepsin D, Plasmin, Plasminogen Activator

Fig. 14

Mouse Models

>C57B6 (normal) mouse +/- streptozotocin (STZ)

>NOD (type 1)

>db/db Diabetic mice

Fig. 16

Insulin and Excipients Used in Studies

>Humalog: 0.01-3 mg insulin

>Insulin lispro without preservatives: 0.01-3 mg/ml

>m-cresol (mC): 0.01-3 mg/ml

>phenol (P): 0.01-3 mg/ml

Fig. 17

Initial Evaluation of Tissue Reactions

*Histopathology*: H&E & Trichrome

*Immunohistochemistry*: Leukocyte populations, fibroblasts, mast cells, as well as human insulin and fibrils, and proteins

*Insulin/fibril distribution in tissue*: FITC-insulin and Insulin IHC using anti-insulin antibodies

*Detection of RNA in cells*: RNA Scope Analysis (Advanced Cell Diagnostics)

Fig. 18

SALINE      DILUENT

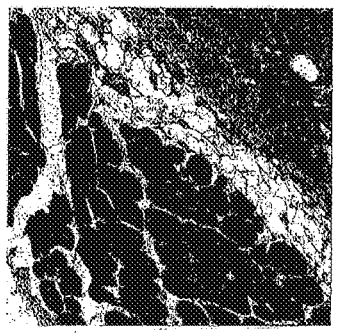 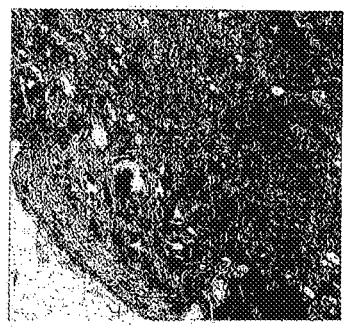

Fig. 19

| Inhibitors & Inducers |
|---|
| Candidate Inhibitors |
| 1. General Anti-Inflammatory |
| Corticosteroids |
| Methylprednisolone |
| NSAID |
| Aspirin (acetylsalicylic acid) |
| 2. Targeted Anti-Inflammatory |
| Inhibitors of pro-inflammatory cytokines |
| IL-1B: Anakinra & IL-1 Trap |
| TNFa: anti-TNF Bupropion |
| 3. Chemokine Inhibitors |
| PMN Inhibitors: pentoxifyline, Reparixin, Antileukinate |
| MQ Inhibitors: Bindarit |
| 4. Angiogenic Agents (blood vessels and lymphatic vessels) |
| Blood Vessels: VEGFa<br>Lymphogenic Vessels: VEGFc and VEGFd |
| 5. Anti-Fibrosis Agents |
| Bortezomib |
| 6. Protease Inhibitors |
| Alpha-2-Macroglobulin, Alpha-1-Antitrypsin (AAT), Aprotinin, SP16, Pepstatin, and/or HALT |

Fig. 22

Mouse Models

>C57B6 (normal) mouse +/- streptozotocin (STZ)

>NOD (type 1)

>ob/ob obese diabetic mice (type 2)

>ob/ob normal (non-diabetic littermates)

>mutant/transgenic mice +/- STZ

Fig. 30

IFP Used in Studies

>Humalog: 0.01-3 mg insulin formulations

>Insulin lispro without preservatives: 0.01-3 mg/ml

>Insulin fibrils: 0.01-3 mg insulin equivalents/ml (+/-P +/-mC)

>m-cresol (mC): 0.01-3 mg/ml
>phenol (P): 0.01-3 mg/ml
>m-cresol (mC) + Phenol (P): 0.01-3 mg/ml

Fig. 31

Evaluation of Tissue Reactions

*Histopathology*: H&E & Trichrome staining

*Immunohistochemistry*: Leukocyte populations, fibroblasts, mast cells etc., as well as human insulin and fibrils, and albumin

*IFP distribution in tissue*: FITC-insulin or Evans blue dye-albumin (diluent and saline)

*Tissue gene expression*: Qiagen qPCR panels

Fig. 32

MQ/DC DEPLETION MODELS

| PHASE | TARGET CELL | MECHANISM | TECHNIQUE | USES |
|---|---|---|---|---|
| I | MQ | Chemical Depletion of Macrophages | Etoposide and Clodronate Liposome Depletion | Systemic and Local MQ Depletion |
| II | MQ | Transgenic Depletion of Macrophage (CD11b – Diphtheria Toxin Receptor Expressing MQ Mice) | CD11b Diphtheria Toxin Receptor Expressing Mice (Jackson Labs) | Systemic and Local MQ Depletion |
| I | MQ | Genetically MQ Deficiency Mice (op/op mice) | CSF-1/MQ Deficient op/op Mice (Jackson Labs) | Systemic and Local MQ Deficiency |
| AIM2 | DC | Transgenic Depletion of Dendritic Cell (CD11c-Diphtheria Toxin Receptor Expressing DC Mice) | CD11c Diphtheria Toxin Receptor Expressing Mice (Jackson Labs) | Systemic and Local DC Depletion |

Fig. 34

| IMPACT OF LOCAL DRUG INFUSION TO IFP TISSUE REACTIONS AND BLOOD GLUCOSE REGULATION [1] (BORTEZOMIB) | | |
|---|---|---|
| TARGET | AGENTS | ACTION |
| Inflammation | Dexmethasone / Prednisone | Blocker |
| Mast Cells | Cromolyn / Doxantrozole | Blocker |
| PMNs / Edema | Aspirin (acetylsalicylic acid) | Blocker |
| Macrophages | Etoposide / Clodronate | Depletion |
| Fibrosis | Bortezomib (peptide) | Blocker |
| Blood Vessels | VEGFa | Inducer |
| Lymphatic vessel | VEGFc / VEGFd | Inducer |

Fig. 35

| TABLE OF OBSERVED TISSUE AND CELLULAR EFFECTS AFTER EXPOSURE TO IFP COMPONENTS | | | |
|---|---|---|---|
| | INSULIN (Stock: 3mg/ml insulin with preservatives) | INSULIN FIBRILS (Stock: 2.5 mg/ml, no preservatives) | INSULIN Preservatives only (Stock: 3 mg/ml m-cresol/phenol) |
| Induces inflammation when injected or infused into skin at standard concentrations (evaluated at 3 days) | YES | YES | YES |
| Toxic to human cells in culture (leukocytes and tissue cells) | YES (>0.01 mg/ml insulin) | YES (>0.005 mg/ml insulin fibrils) | YES (>0.01 mg/ml preservatives) |
| Induces morphologic changes in human leukocytes and tissue cells (cell swelling) | YES (>0.001 mg/ml insulin) | YES (>0.0005 mg/ml insulin fibrils) | YES (>0.001 mg/ml preservatives) |
| Induces increased pro-inflammatory cytokine expression from human leukocytes in culture (i.e. IL-1B, IL-8 and interferon gamma) | YES (2-5x) (>0.001 mg/ml insulin) | YES (2-5x) (>0.0005 mg/ml insulin fibrils) | YES (2-5x) (>0.001 mg/ml preservatives) |

Fig. 36

| TARGET | AGENTS | ACTION |
|---|---|---|
| Inflammation | Dexmethasone / Prednisone | Blocker |
| Mast Cells | Cromolyn / Doxantrozole | Blocker |
| PMNs / Edema | Aspirin (acetylsalicylic acid) | Blocker |
| Macrophages | Etoposide / Clodronate | Depletion |
| Fibrosis | Bortezomib (peptide) | Blocker |
| Blood Vessels | VEGFa | Inducer |
| Lymphatic vessel | VEGFc / VEGFd | Inducer |

Fig. 37

TABLE OF OBSERVED TISSUE AND CELLULAR EFFECTS AFTER EXPOSURE TO IFP COMPONENTS

| | INSULIN (Stock: 3mg/ml insulin with preservatives) | INSULIN FIBRILS (Stock: 2.5 mg/ml, no preservatives) | INSULIN Preservatives only (Stock: 3 mg/ml m-cresol/phenol) |
|---|---|---|---|
| Induces inflammation when injected or infused into skin at standard concentrations (evaluated at 3 days) | YES | YES | YES |
| Toxic to human cells in culture (leukocytes and tissue cells) | YES (>0.01 mg/ml insulin) | YES (>0.005 mg/ml insulin fibrils) | YES (>0.01 mg/ml preservatives) |
| Induces morphologic changes in human leukocytes and tissue cells (cell swelling) | YES (>0.001 mg/ml insulin) | YES (>0.0005 mg/ml insulin fibrils) | YES (>0.001 mg/ml preservatives) |
| Induces increased pro-inflammatory cytokine expression from human leukocytes in culture (i.e. IL-1B, IL-8 and interferon gamma) | YES (2-5x) (>0.001 mg/ml insulin) | YES (2-5x) (>0.0005 mg/ml insulin fibrils) | YES (2-5x) (>0.001 mg/ml preservatives) |

Fig. 38

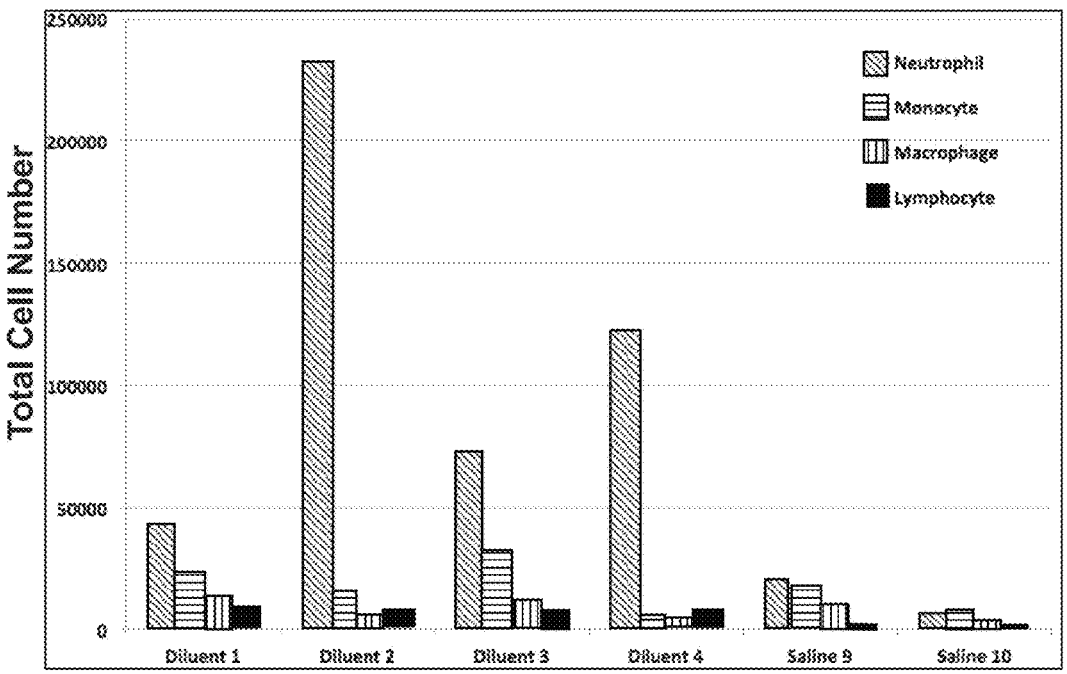

Insulin preservative / diluent induced inflammation in a normal CD-1 mouse using a modified "air pouch" model. To determine whether insulin related diluents/preservatives induce inflammation in vivo, a modification of the classical air pouch was utilized. For that, air was injected subcutaneously into the mouse skin creating a sustained compartment (pouch) for injection of diluent or saline (control). The diluent and the control agent (saline) were infused continuously for 7 days at a rate of 5 units equivalents/hour one-day post air pouch creation. After 7 days of infusion, the air pouch was lavaged. The resulting fluid was characterized for cell number (auto-hemo-cytometer), and cell type using Fluorescence Activated Cell Sorting (FACS). Consistently diluent preservative treated mice demonstrated a dramatically higher cell counts when compared to saline infused mice. Additionally Neutrophil, Monocyte/Macrophage and Lymphocyte counts were significantly higher in the diluent/preservative infused mice when compared to the saline treated mice.

Fig. 43

1) Toxicity: Are insulin and its preservatives toxic to human neutrophils (PMN's) *in vitro*?

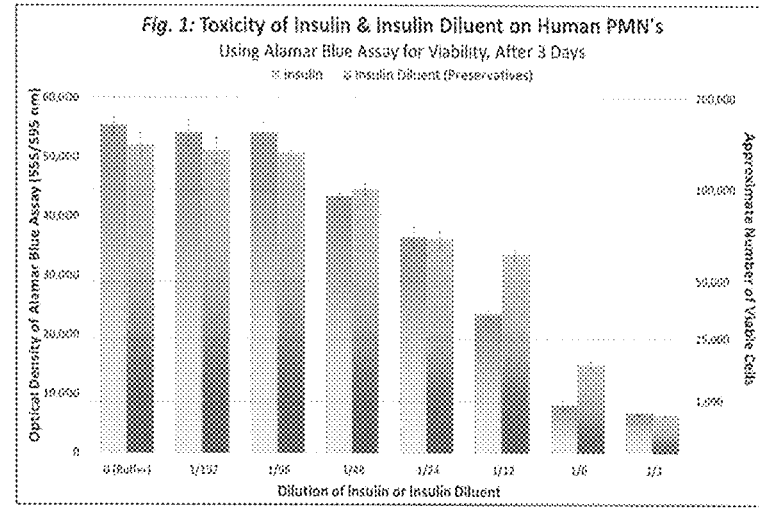

*Figure 1* shows the number of PMN's surviving after 3 days in buffer +/- a serial dilution of insulin or its preservatives (phenol and m-cresol). Even at a 1:48 dilution, there were significantly fewer cells surviving than in buffer alone. As the concentration increased, the number of cells surviving decreased for both insulin and insulin diluent. At the highest concentration tested (a 1:3 dilution of standard insulin formulations), fewer than 1,000 cells survived, compared to over 100,000 in the buffer solution (estimated from optical density).

Fig. 52

3) Degradation: Do leukocytes and leukocyte proteases degrade insulin *in vitro*?

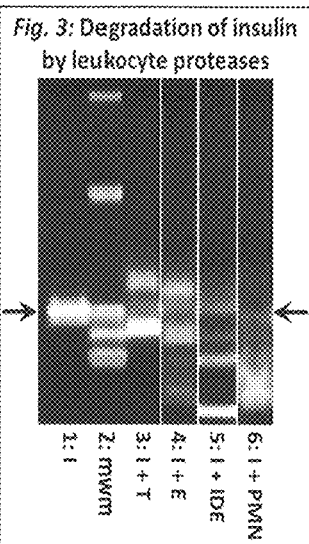

Fig. 3: Degradation of insulin by leukocyte proteases

Key: I = Insulin, T = Trypsin, E = Elastase, IDE = Insulin Degrading Enzyme, PMN = Triton X100 extract of human PMN, mwm = molecular weight marker.

*Figure 3* shows degradation of insulin by leukocyte proteases. Analysis by lane:
1) Insulin appears as a bright yellow band (MW = 5.8kDa).
2) Molecular marker with 2kDa, 25kDa, and 75kDa in red; insulin in yellow.
3) Trypsin degrades insulin so that the original band is no longer visible, replaced by two primary degradation products.
4) Elastase cleaves insulin at many sites, leaving a streak of products at a wide range of molecular weights.
5) Insulin Degrading Enzyme cleaves insulin into several smaller peptides, including a bright band at a very low molecular weight.
6) PMN's taken from a Type 1 diabetic patient and lysed with Triton X100 completely degrade insulin into a wide range of products.

Lymphocytes and monocytes taken from human peripheral blood also degraded insulin, although not to the same extent (data not shown). PMN's from non-diabetic patients degraded insulin as well (data not shown).

Fig. 53

SYSTEMS, METHODS AND PRODUCTS FOR MINIMIZING TISSUE REACTIONS AND TISSUE INJURY AT AN INFUSION SITE

BACKGROUND

Despite their demonstrated clinical benefits, currently insulin infusion sets are only approved for in vivo usage for only 3 days. Even with this limited approved lifespan, a substantial portion of sets fail to meet this recommended lifespan during practical use. Nevertheless, Continuous Subcutaneous Insulin Infusion (CSII) therapy represents the most advanced form of insulin delivery technology currently available and administers more precise amounts of insulin in a programmable format as compared to traditional injection methods, which provides increased flexibility and enhanced quality of life for the user. To achieve effective glucostasis using an artificial pancreas, a combination of a highly accurate continuous glucose monitor (CGM) and reliable continuous subcutaneous insulin infusion (CSII) is required. Although CGM performance and lifespan has significantly improved over the last decade, CSII with a current lifespan of 3 days or less has not. As such the current approved usage lifespans for commercial CGM and CSII devices is highly mismatched with in vivo durations of 10+ days vs. 3d, respectively.

The high occurance of inflammation and scarring at insulin infusion sites in patients with diabetes is well known (i.e. 25-42%) particularly in pediatric populations and whereas infection at insulin infusion sites is also frequently seen. It would be useful to develop products and methods to reduce this inflammation and scarring.

SUMMARY

One embodiment described herein is a method of lowering the concentrations of at least one of preservatives and fibrils in a liquid insulin formulation, comprising replacing at least one of phenol and m-cresol with at least one of cyclodextrins, cyclodextrin polymers and cyclodextrin beads. Another embodiment is a method for removing at least one of preservatives at fibrils from a liquid insulin composition comprising incorporating at least one of an ion exchange resin and cyclodextrin polymers or beads into the infusion set. A liquid insulin formulation comprising cyclodextrins and/or cyclodextrin polymers as preservatives also is described.

Another embodiment is a method of lowering the concentration of phenol and/or m-cresol, and/or fibrils in a liquid insulin composition by replacing at least a portion of the phenol and/or m-cresol with at least one of cyclodextrins and cyclodextrin polymers. The disclosure also describes a method for removing insulin solubilizers from a liquid insulin composition comprising incorporating at least one of an ion exchange resin and cyclodextrin into the infusion set. A liquid insulin formulation comprising cyclodextrins and/or cyclodextrin polymers as solubilizers also is disclosed.

A further embodiment is a method for removing antimicrobial agents from a liquid insulin composition comprising incorporating at least one of an ion exchange resin and cyclodextrin polymers and/or beads into the infusion set. A liquid insulin formulation comprising cyclodextrins and/or cyclodextrin polymers as anti-microbial agents also is described.

An insulin delivery apparatus is disclosed comprising an ion exchange resin configured to remove insulin preservatives. An insulin delivery system comprising cyclodextrin preservatives is described herein.

Another embodiment is a method of preventing insulin degradation at an infusion site comprising incorporating an anti-protease into the insulin formulation. A system comprising the filter used to remove fibrils from a liquid insulin formulation is described. A method is disclosed for suppressing inflammation resulting from the injection or infusion of insulin, comprising delivering an anti-inflammatory drug, factor or agent to (a) the insulin formulation or (b) during an insulin infusion. Additionally, a method of suppressing fibrosis induced insulin delivery, comprising incorporating growth factor inhibitors into the liquid insulin formulation is disclosed.

A further embodiment is a method of inducing blood vessel and/or lymphatic vessel growth at an insulin infusion site, comprising introducing vascular endothilial growth factor to the infusion site. A method of introducing an anti-protease, anti-inflammatory, anti-fibrotic or lymphatic drug, factor or agent to a liquid insulin composition using a dual lumen cannula also is disclosed.

A further embodiment is a method of introducing an anti-protease, anti-inflammatory, anti-fibrotic or lymphatic drug, factor or agent to a liquid insulin composition using a dual lumen cannula. Yet another embodiment is a method for coating an insulin infusion set cannula and/or a biocompatible collar for the cannula with a composition that contains at least one of a basement membrane or another extracellular matrix, an oil, such as a high molecular weight silicone oil, and a lubricant, such as proteoglycan 4 (PRG4), Libricin and/or hyaluronan. Another embodiment is a method for local delivery of agents from these coatings to suppress inflammation, fibrosis and/or insulin degradation, and optionally also promoting blood and lymphatic vessel ingrowth into the infusion site.

In embodiments, the method further comprises removing fibrils by incorporating a fibril filtration system in the insulin pump system in order to remove at least one of proteins and protein complexes having a molecular weight between 36 thousand and 50 thousand. In some cases, the insulin formulation includes at least one of chlorohexidine and curcumin as an anti-microbial agent.

BRIEF DESCRIPTION OF THE DRAWINGS

In embodiments, the method further comprises removing fibrils by incorporating a fibril filtration system in the insulin pump system in order to remove at least one of proteins and protein complexes having a molecular weight between 36 thousand and 50 thousand. In some cases, the insulin formulation includes at least one of chlorohexidine and curcumin as an anti-microbial agent.

In embodiments, the method further comprises incorporating into an infusion site for the insulin pump system a chemokine inhibitor comprising at least one member selected from the group consisting of 3,7-dimethyl-1-(5-oxohexyl)purine-2,6-dione (pentoxifylline), (2R)-2-[4-(2-methylpropyl)phenyl]-N-methylsulfonylpropanamide (reparixin), (2S)-2-[[(2R)-2-[[(2S)-2-[[(2S)-2-[[(2S)-2-[[(2S)-2-acetamido-5-(diaminomethylideneamino)pentanoyl]amino]-5-(diaminomethylideneamino)pentanoyl]amino]-3-(1H-indol-3-yl)propanoyl]amino]-3-(1H-indol-3-yl)propanoyl]amino]-3-sulfanylpropanoyl]amino]-5-(diaminomethylideneamino)pentanamide (antileukinate) and 2-[(1-benzylindazol-3-yl)methoxy]-2-methylpropanoic acid (bindarit). In some cases, the method includes incorporating [(1R)-3-methyl-1-[[(2S)-3-phenyl-2-(pyrazine-2- carbonylamino)propanoyl]amino]butyl]boronic acid (bortezomib) into an infusion site for the insulin pump system to suppress fibrosis by blocking TGFb signaling pathways.

Figure 1A:
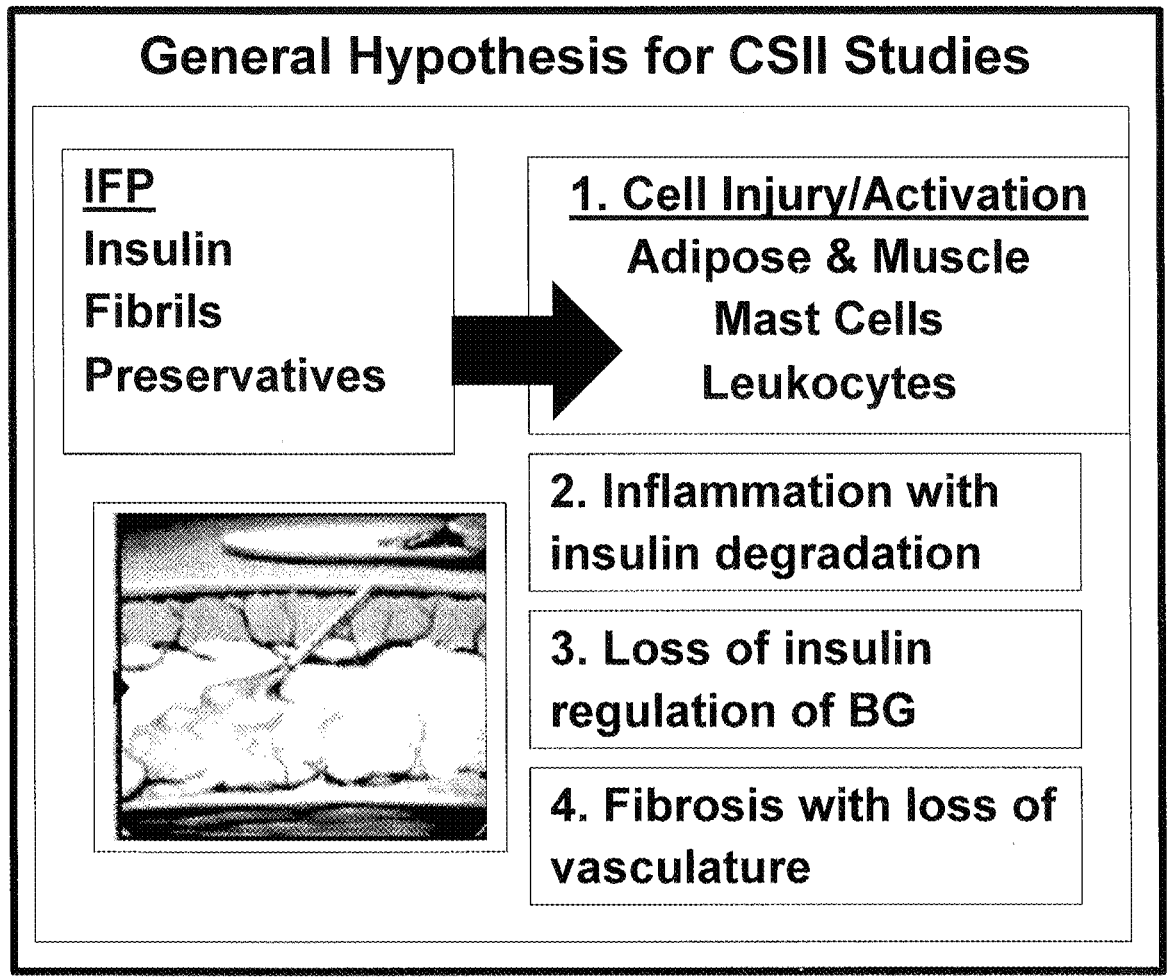

FIG. 1A schematically illustrates the effects of insulin fibrils and preservatives on tissue.

Figure 1B:
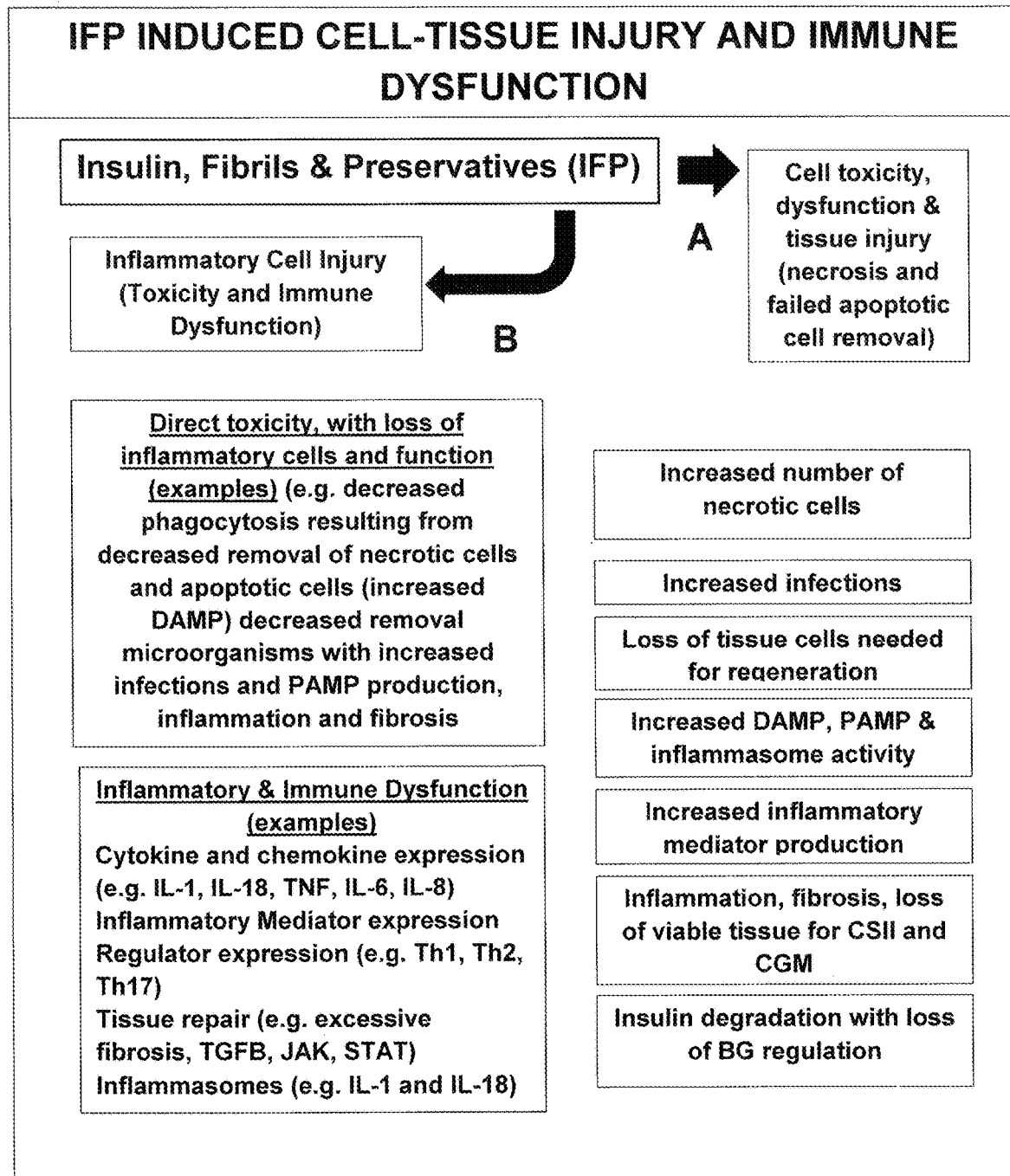

FIG. 1B is a chart showing the effect of insulin, fibrils and preservatives on cells and tissues.

Figure 2:
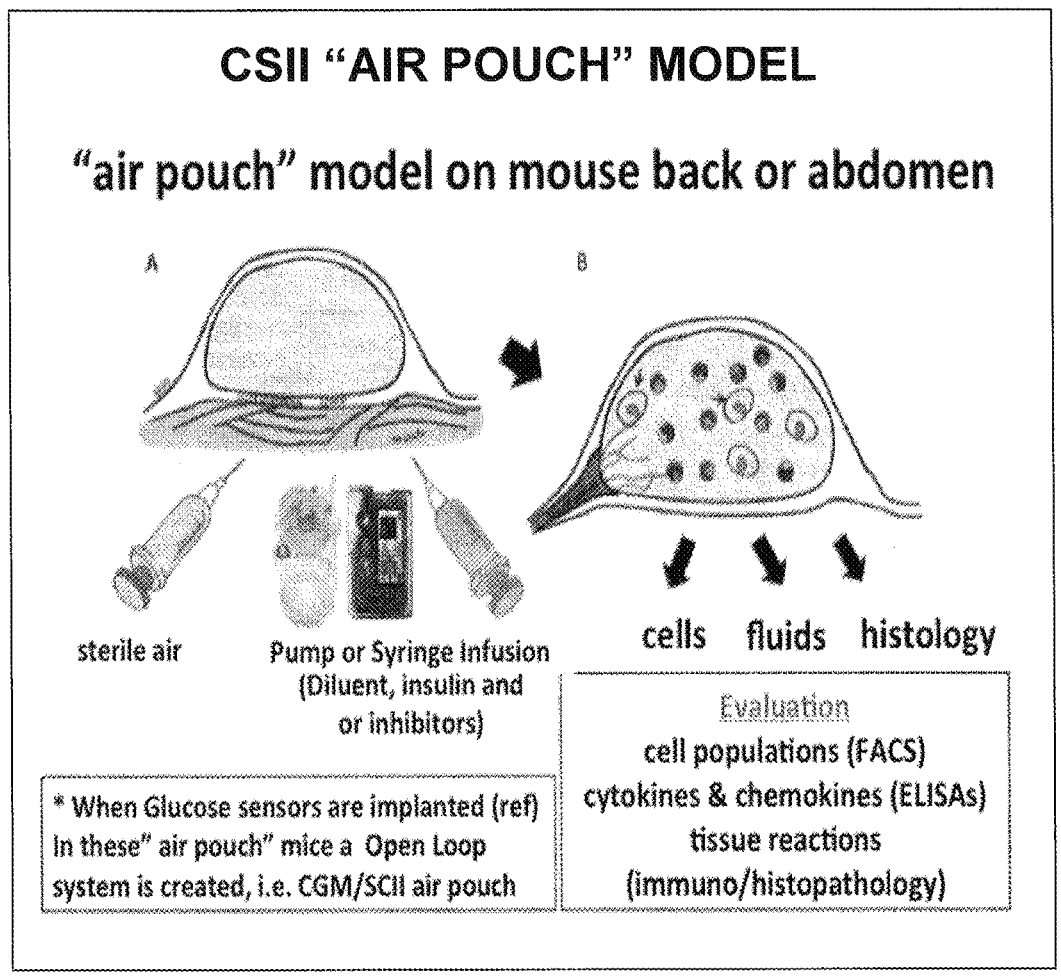

FIG. 2 schematically shows a mammalian CSII air pouch model used in testing described herein.

Figure 3:
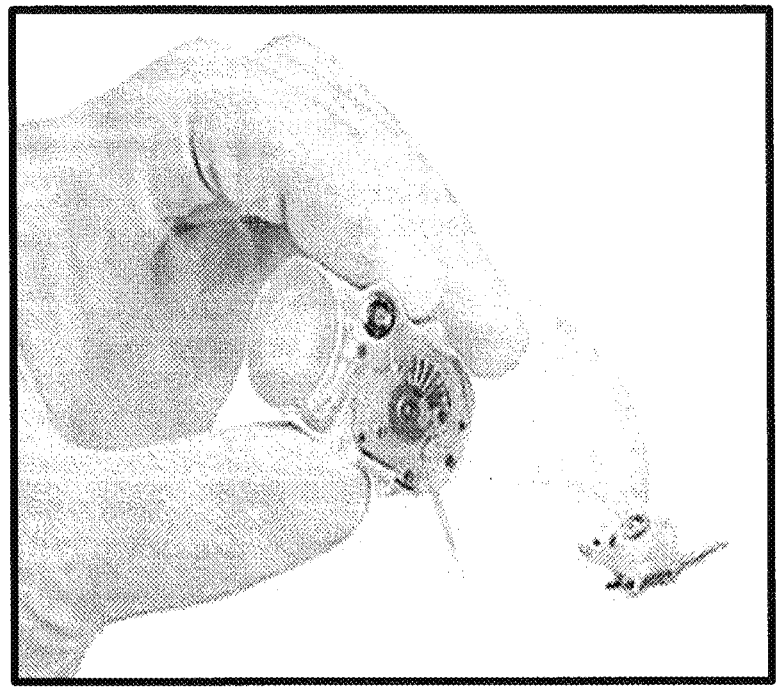

FIG. 3 shows an example of a murine transdermal insulin pump.

Figures 4A, 4B:
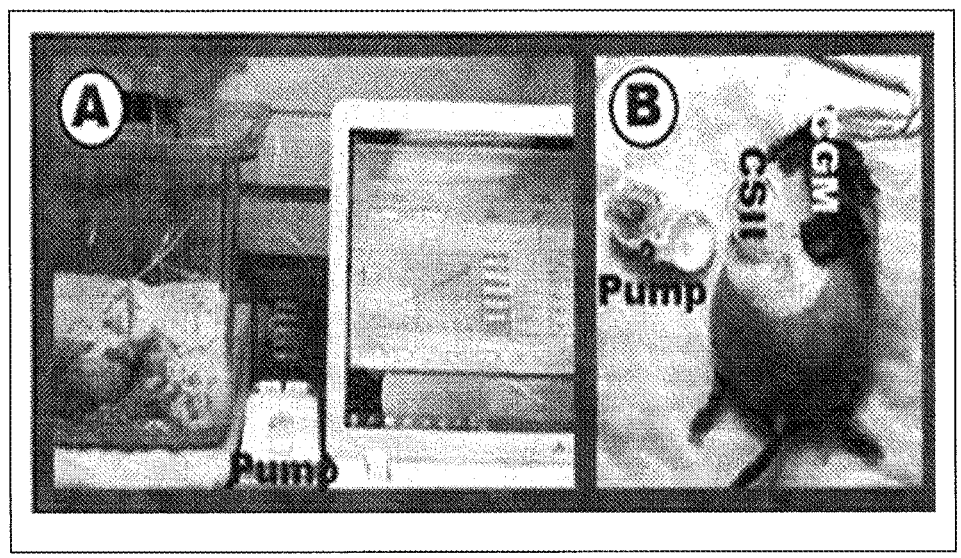

FIG. 4A shows equipment used in the mammalian air pouch open loop model.

FIG. 4B shows a mouse being studied using the equipment shown in FIG. 4A.

Figure 5:
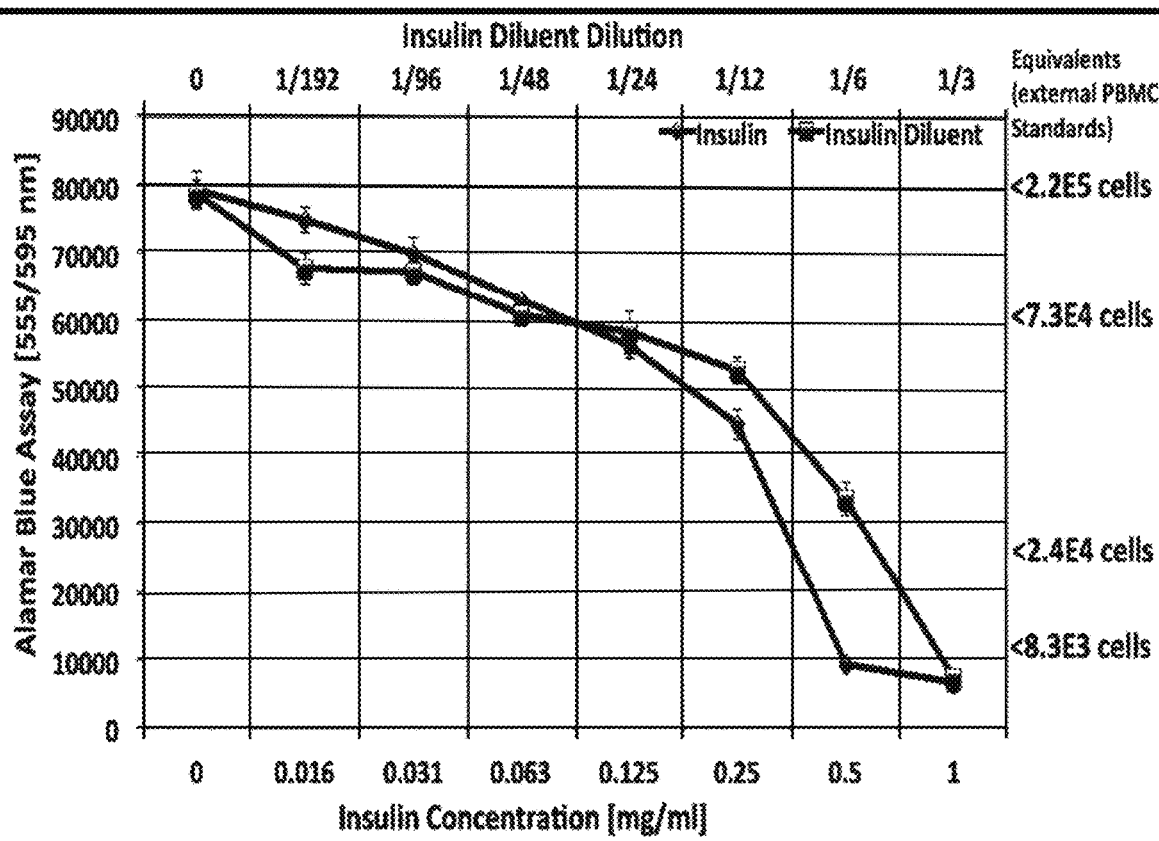

FIG. 5 is a graph showing the in vitro toxicity of insulin and insulin formulation excipients on human PBMC.

Figures 6, 7A:
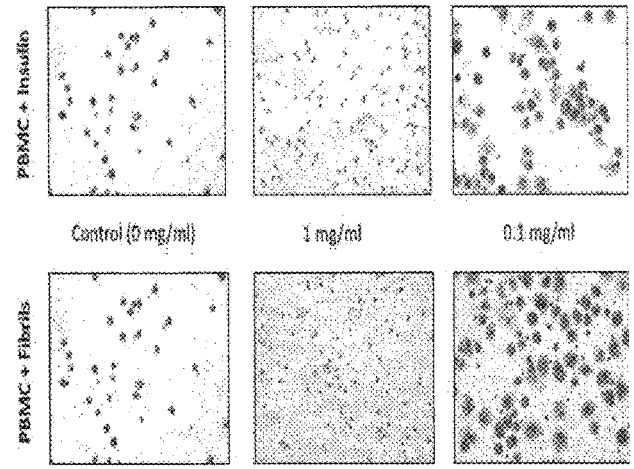

FIG. 6 shows PBMC morphology after exposure to insulin or fibrils.

FIG. 7A is a table showing the impact of excipients/diluents (preservatives) on PBMC expression in vitro.

Figure 7B:
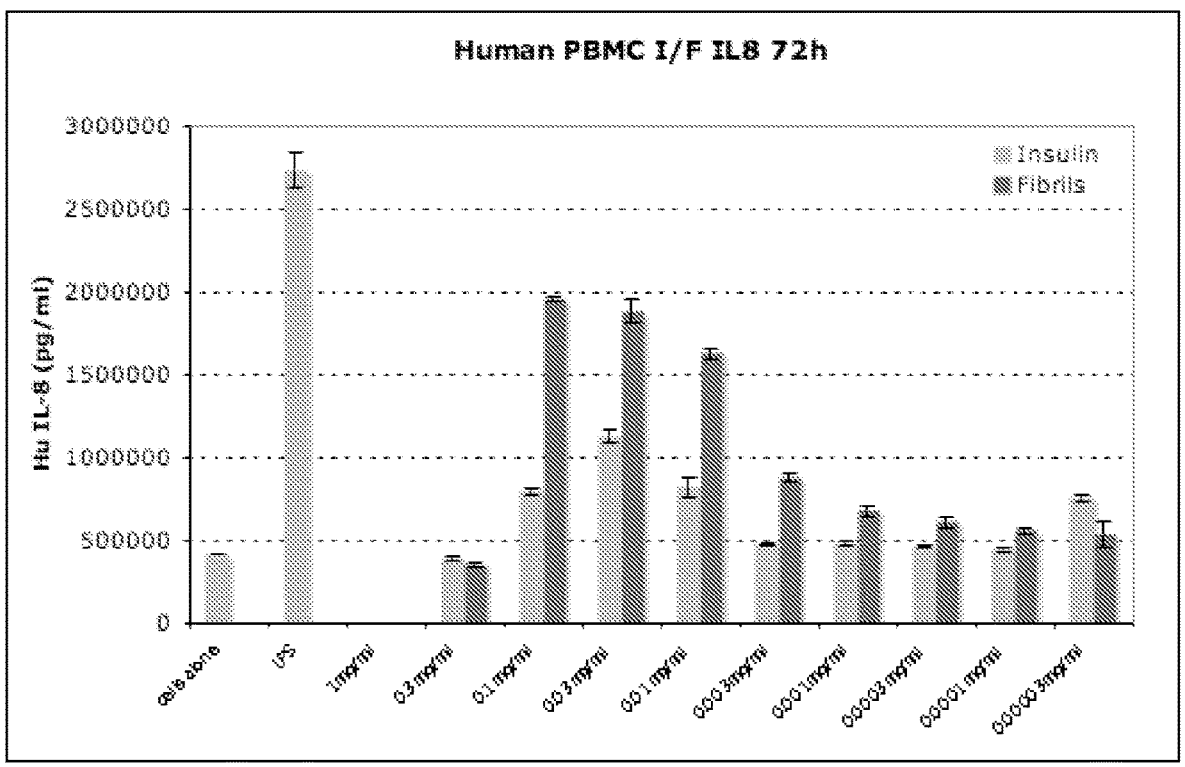

FIG. 7B is a graph showing IL-8 chemokine induction in human PBMC's by insulin and/or excipients.

Figure 7C:
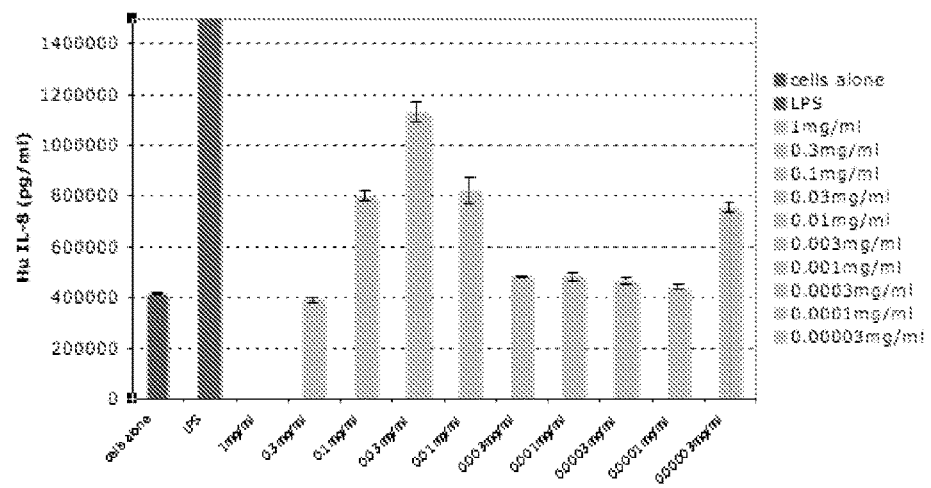

FIG. 7C is a graph showing IL-8 expression by human PBMC in vitro.

Figure 7D:
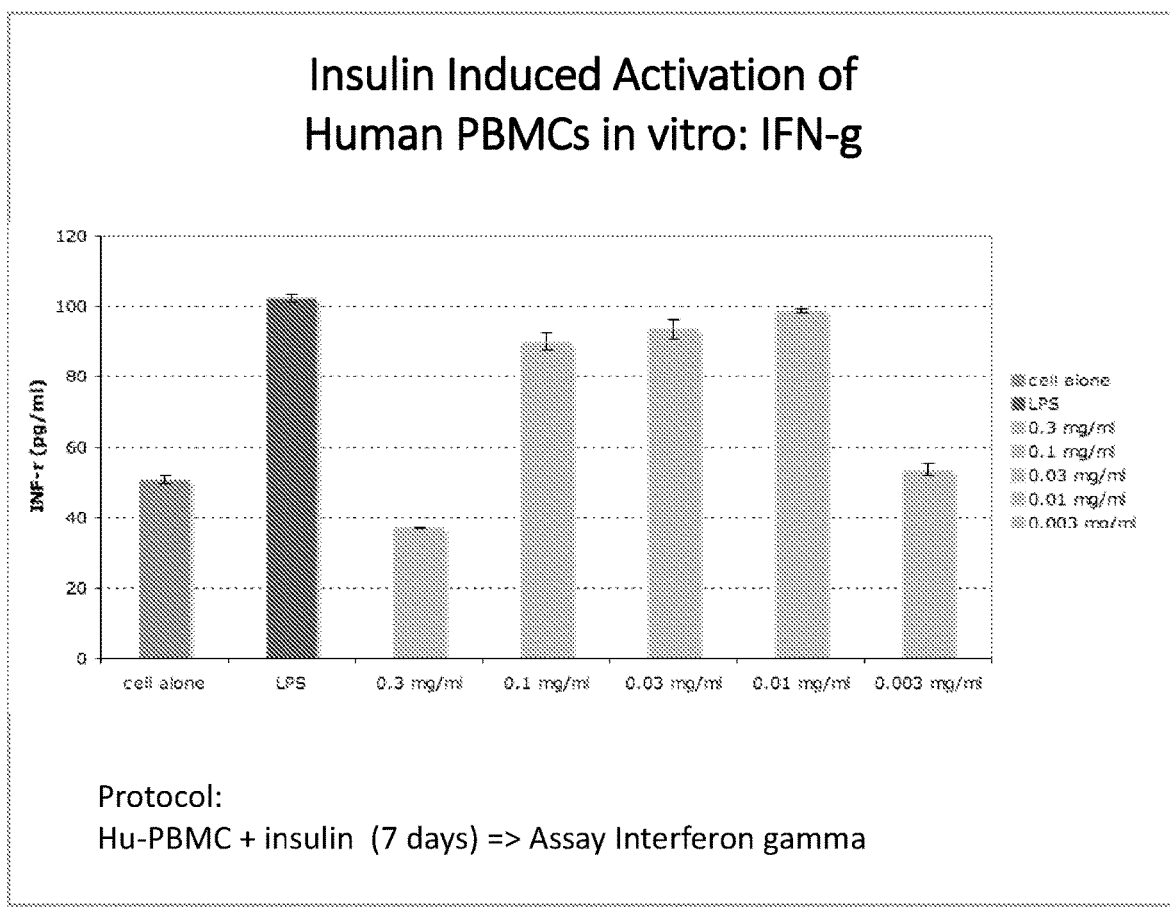

FIG. 7D is a graph showing INF-g expression by human PBMC in vitro.

Figures 8A, 8B, 8C:
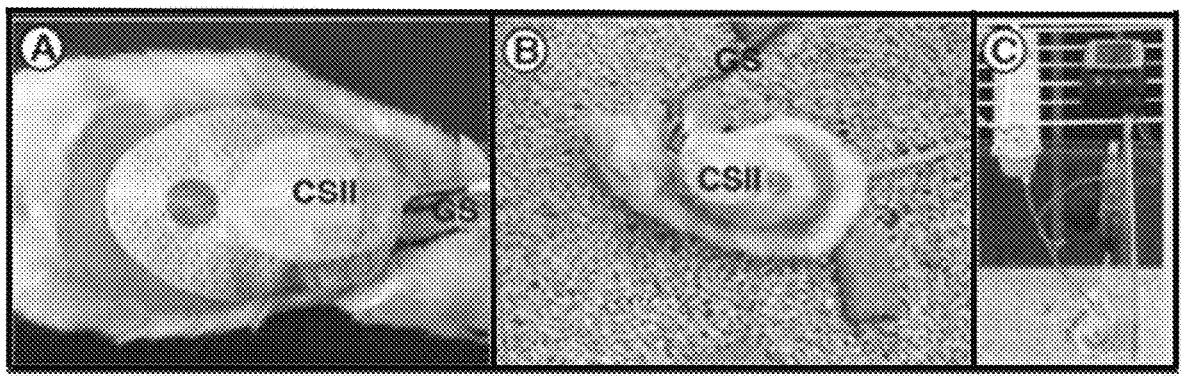

FIG. 8A shows a test mouse.

FIG. 8B is another view of the test mouse.

FIG. 8C shows a third view of the test mouse.

Figure 8D:
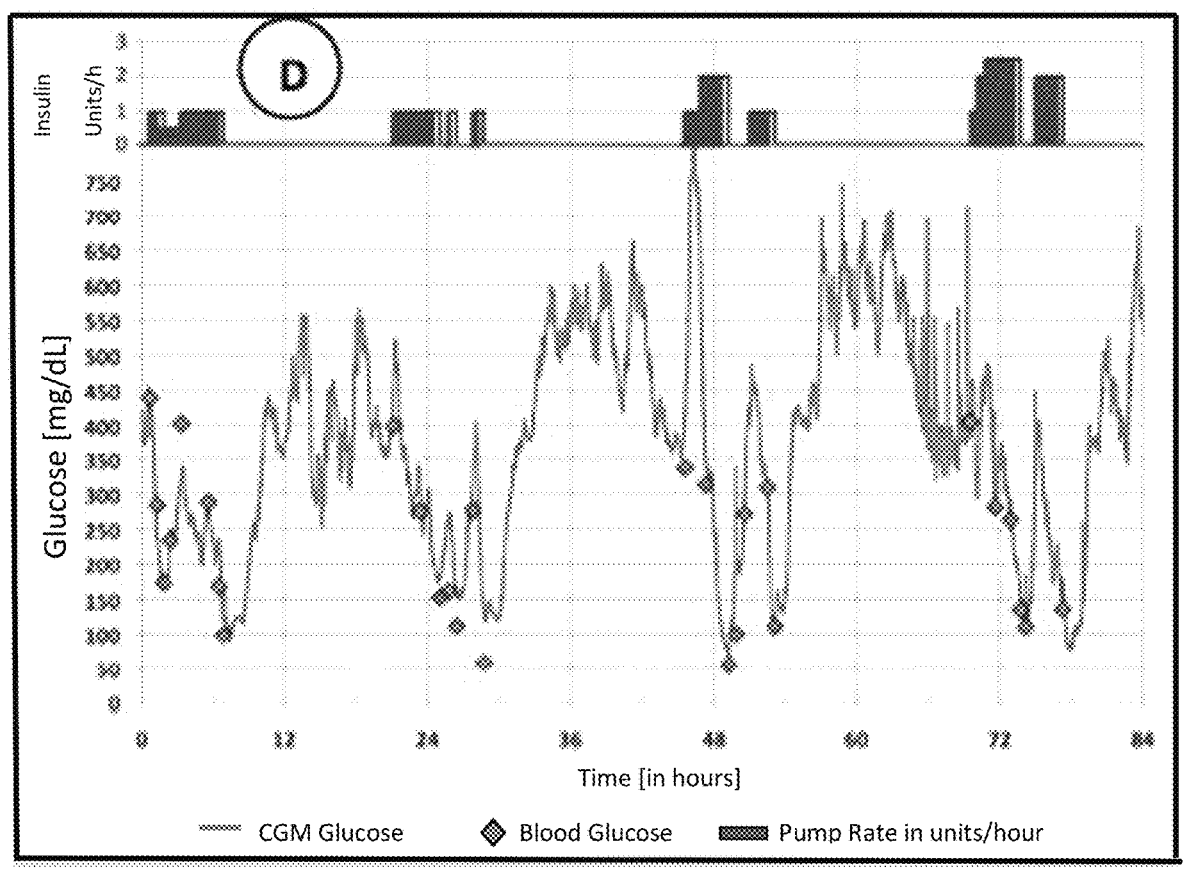

FIG. 8D is a graph showing continuous glucose monitoring (CGM) blood glucose levels and external BG control test monitored in a diabetic NOD mouse.

Figure 9A:
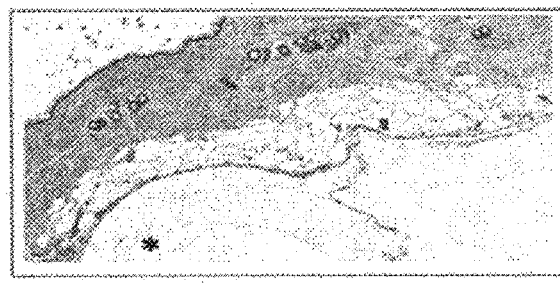

FIG. 9A shows H & E stained mouse skin and SC tissue sections in a control mouse that has been administered saline.

Figure 9B:
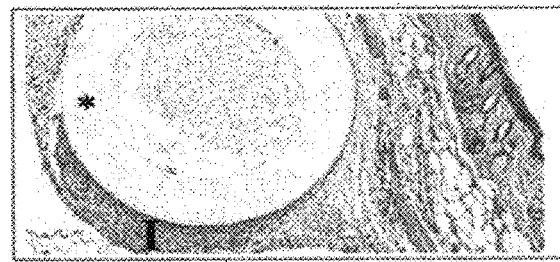

FIG. 9B shows H & E stained mouse skin and SC tissue sections in a normal mouse that has received insulin.

Figure 9C:
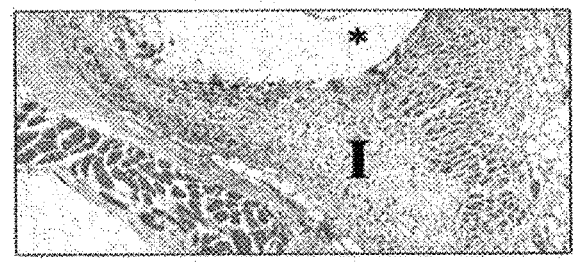

FIG. 9C shows H & E stained mouse skin and SC tissue sections in a diabetic mouse that has received insulin.

Figure 9D:
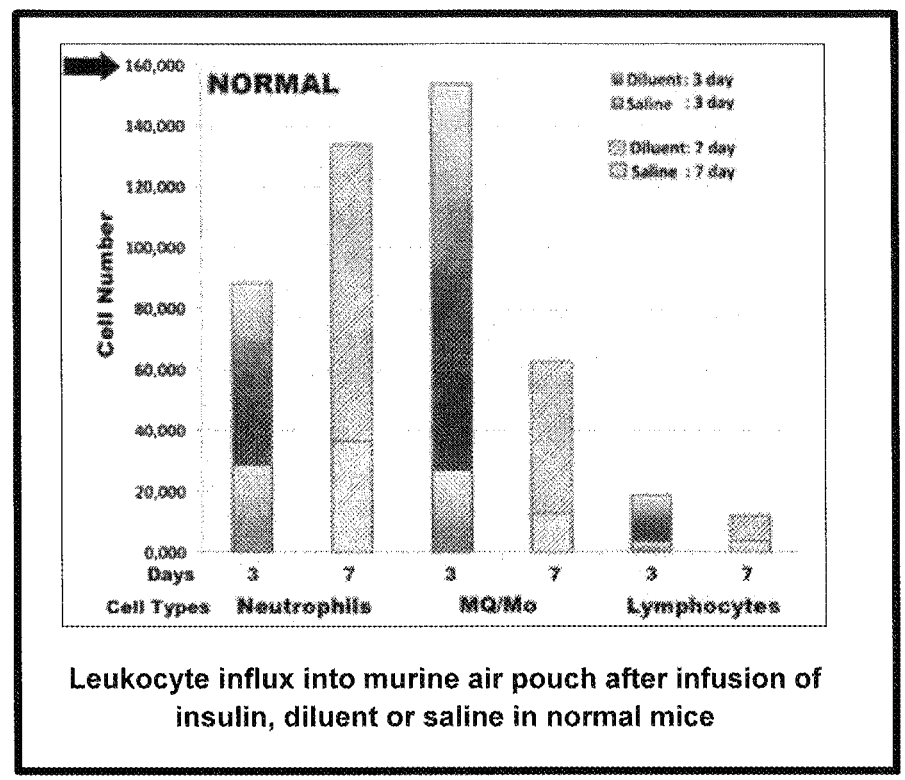

FIG. 9D is a bar graph showing leukocyte influx into a murine air pouch model for a normal mouse.

Figure 9E:
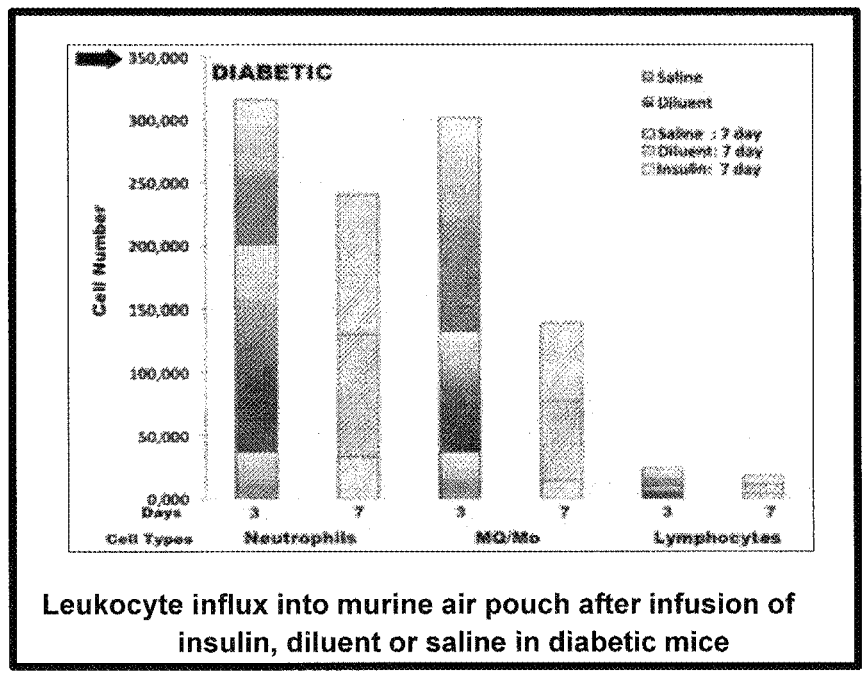

FIG. 9E is a bar graph showing leukocyte influx into a murine air pouch model for a diabetic mouse.

Figure 10:
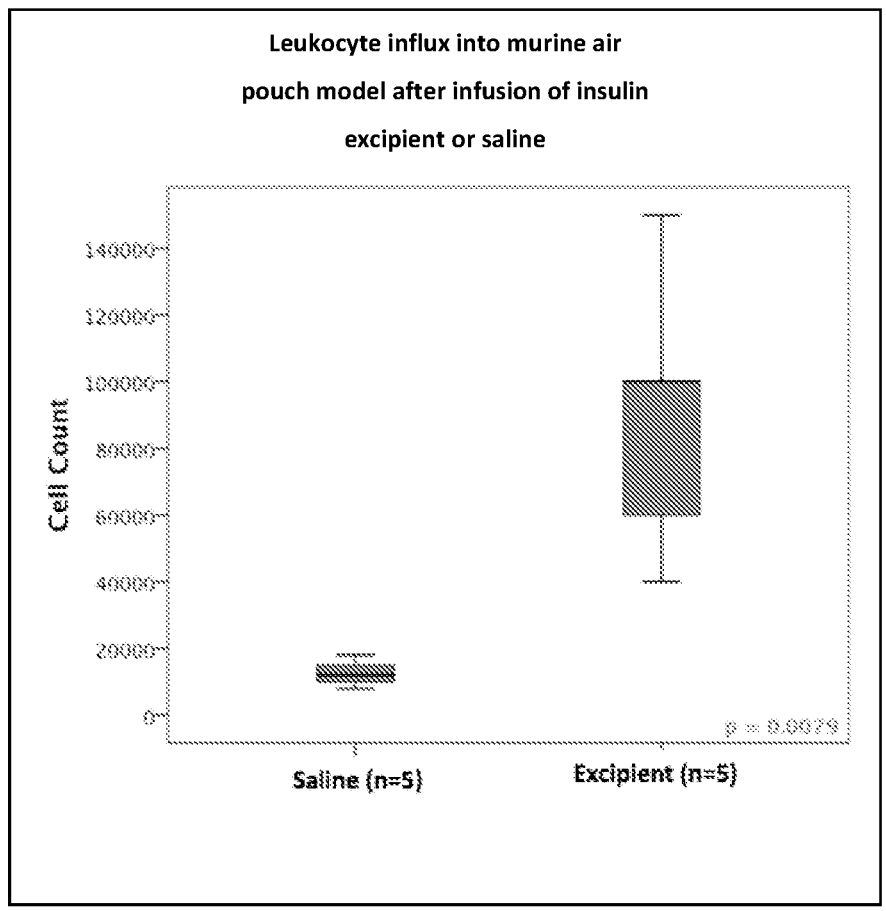
Figure 11A:
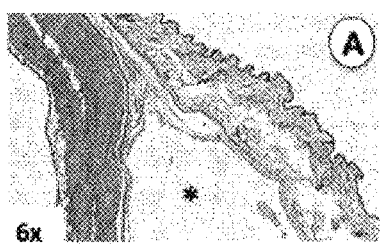
Figure 11B:
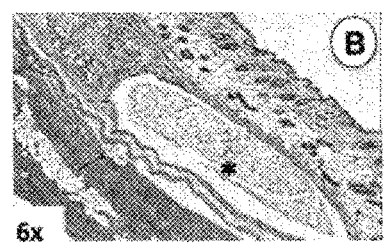
Figure 11C:
Figure 11D:
Figure 11E:
Figure 11F:
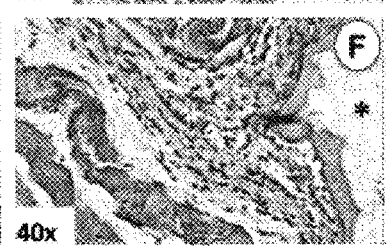

FIG. 10 is a graph showing leukocyte influx into a murine air pouch model after an infusion of insulin excipient or saline.

FIGS. 11A-11F show the effect of saline and insulin infusion excipients on inflammation over a three day period.

Figures 12A, 12B, 12C:
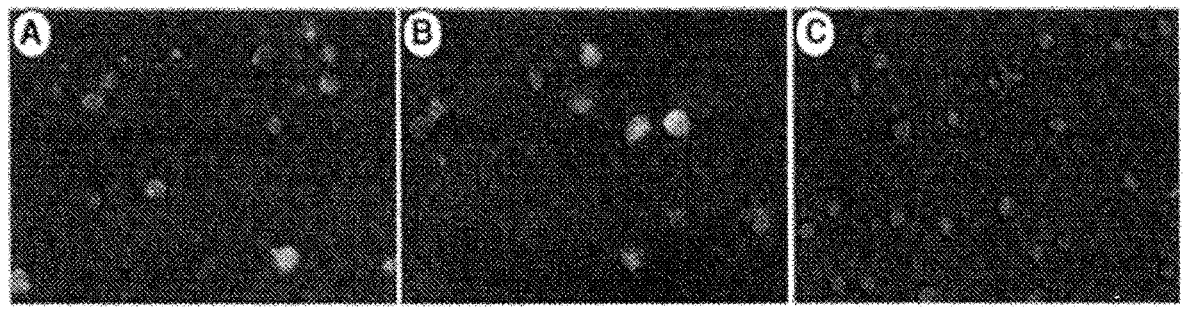

FIGS. 12A-12C show the uptake of FITC-insulin by PBMCs in vitro.

Figures 13A, 13B, 13C:
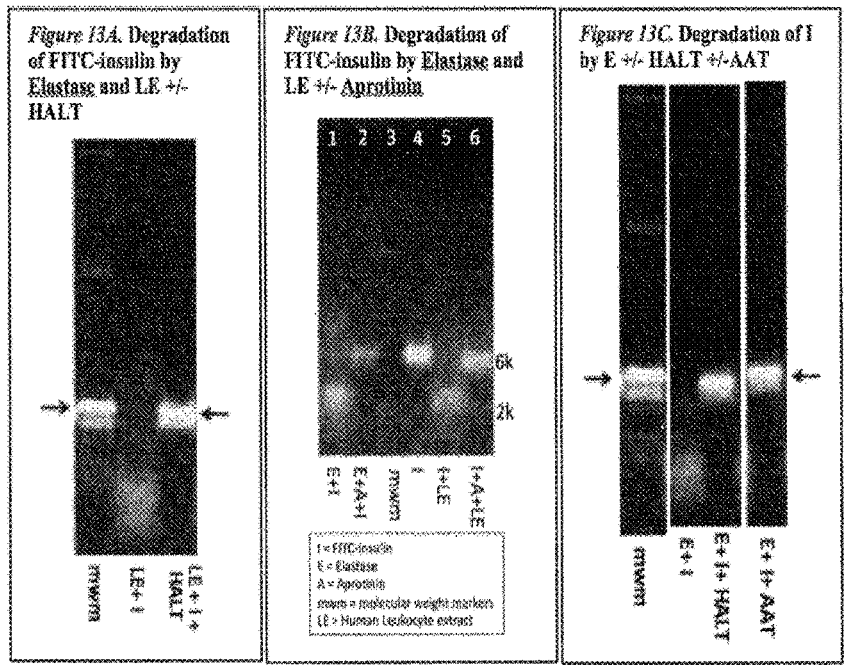

FIGS. 13A-13C show the impact of leukocyte protease on insulin.

FIG. 14 is a table showing the impact of anti-proteases on FITC insulin degradation.

Figure 15:
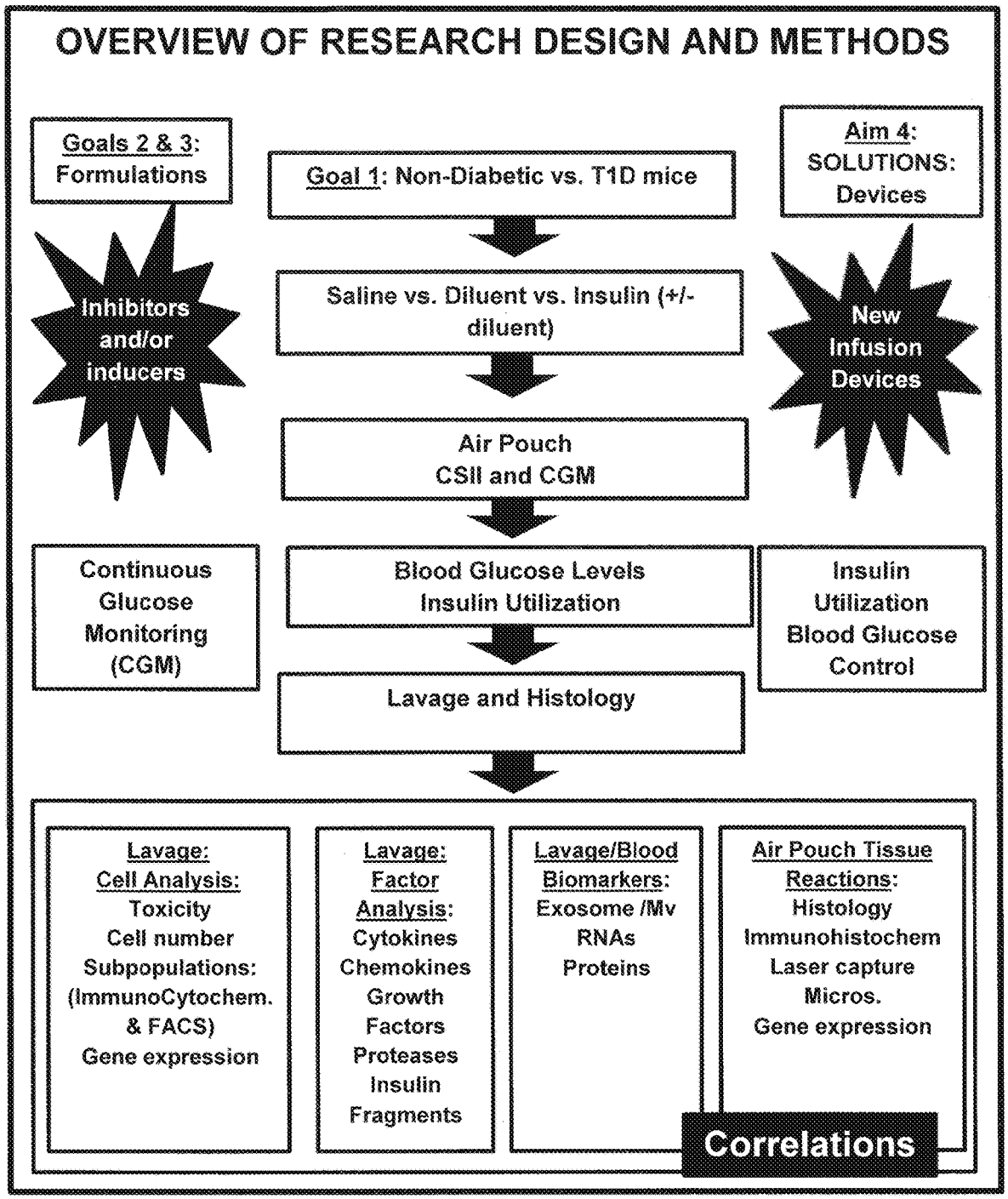

FIG. 15 is a table showing an overview of research described herein.

FIG. 16 is a table showing types of mice used in tests described herein.

FIG. 17 is a table describing the insulin and excipients used in studies described herein.

FIG. 18 is a table describing the initial evaluation of tissue reactions detected in tests described herein.

FIG. 19 shows photos of tissue exposed to saline vs. diluent.

Figures 20A, 20B, 20C:
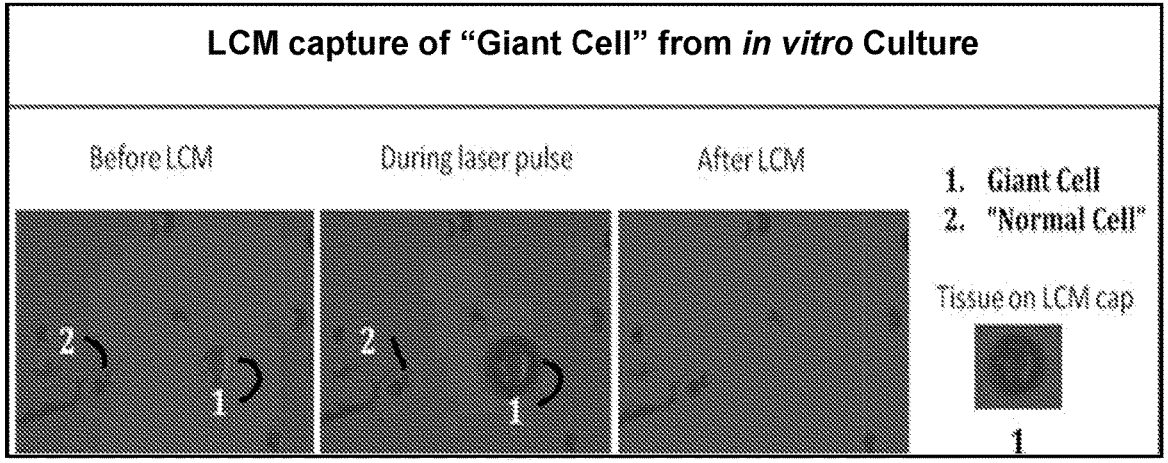

FIGS. 20A-20C are photomicrographs showing LCM capture of "Giant Cell" from in vitro culture.

Figure 21:
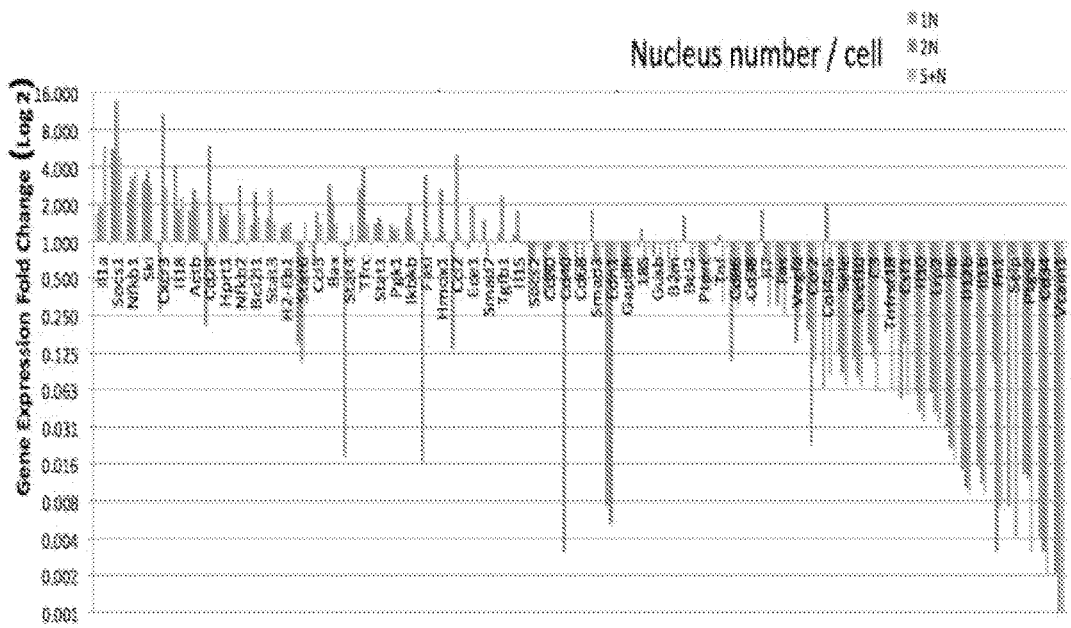

FIG. 21 is a graph of qPCR RNA analysis of macrophages (MQ) and giant cells obtained by LCM.

FIG. 22 is a table showing inhibitors and inducers.

Figure 23:
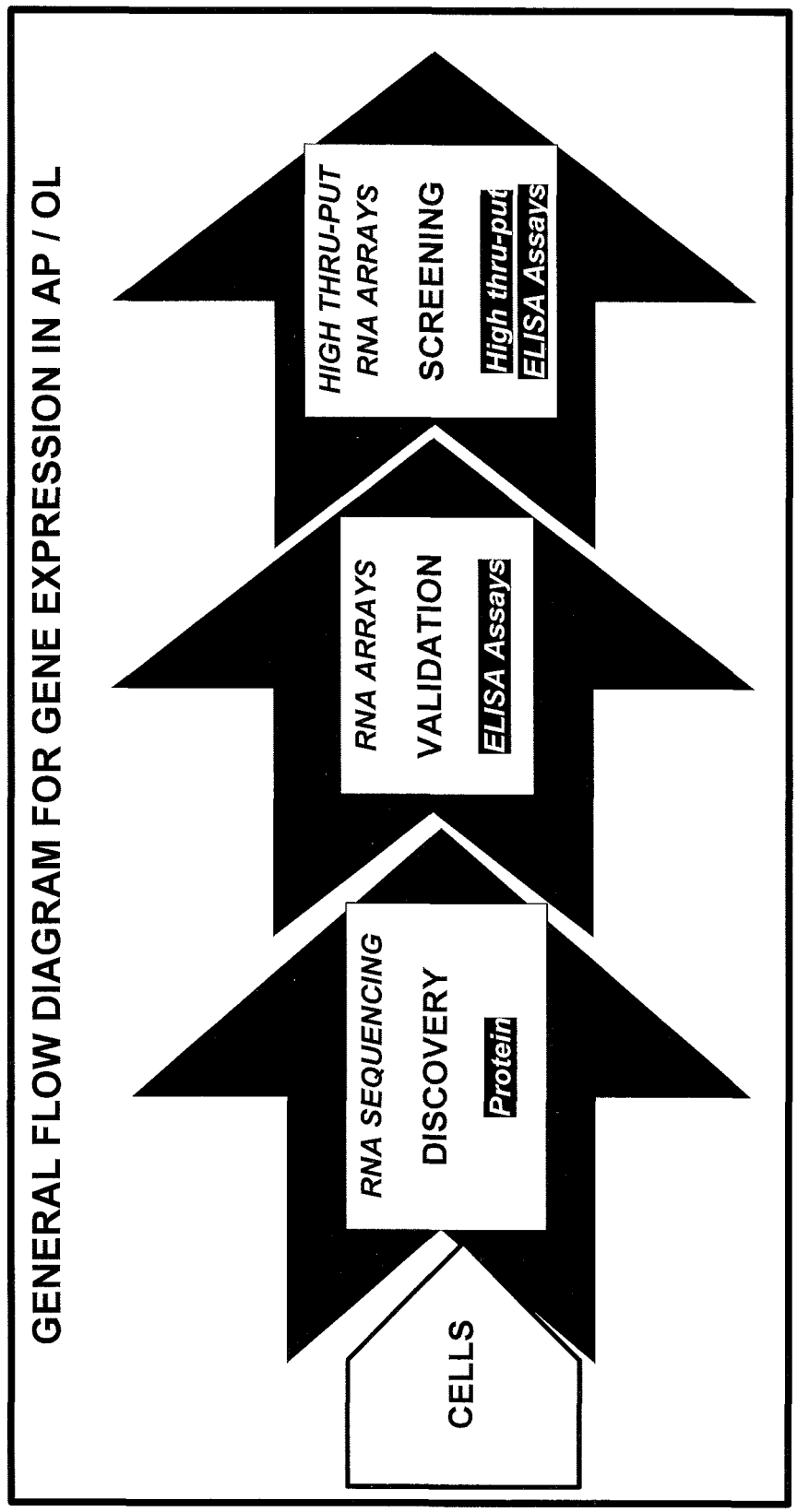

FIG. 23 is a general flow diagram for gene expression in AP/OL.

Figure 24:
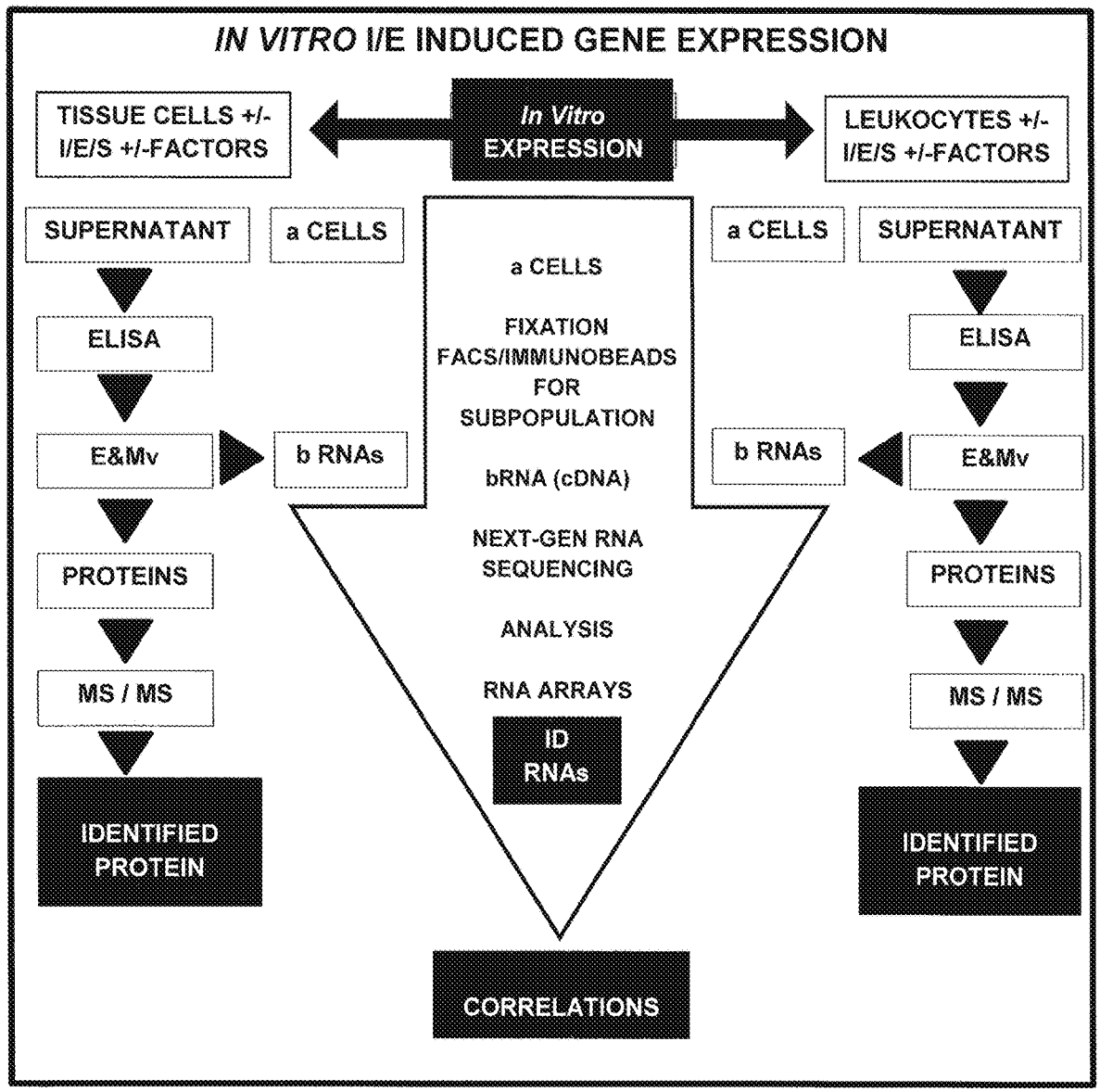
Figure 25A:
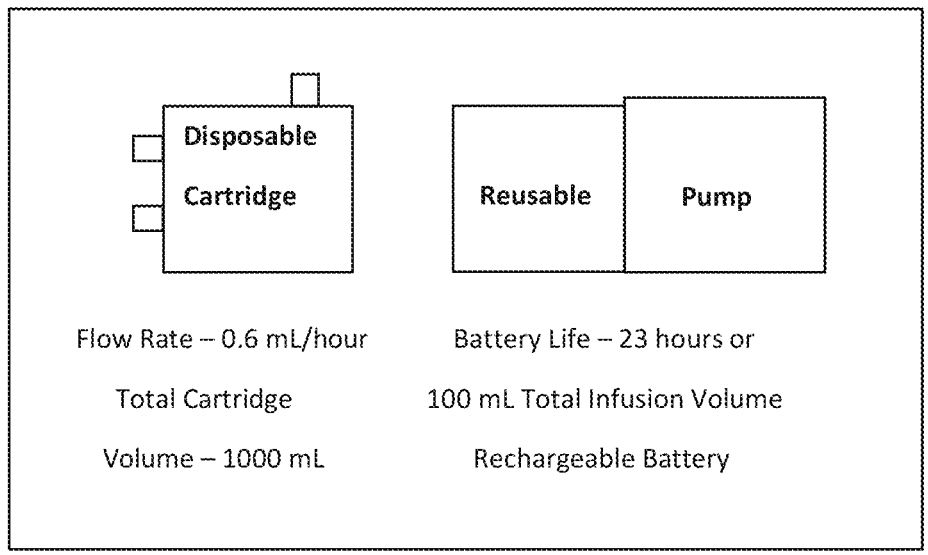
Figure 25B:
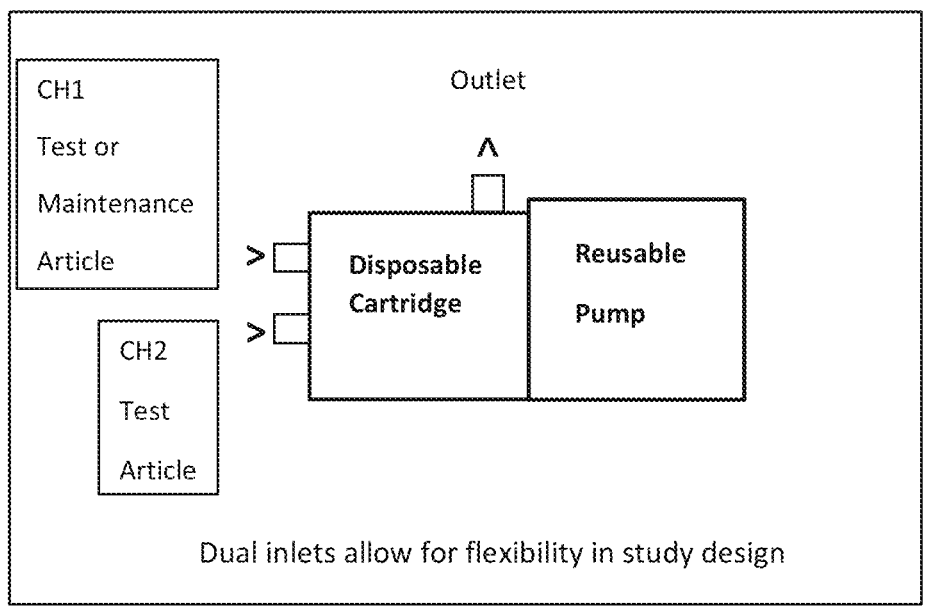
Figure 25C:
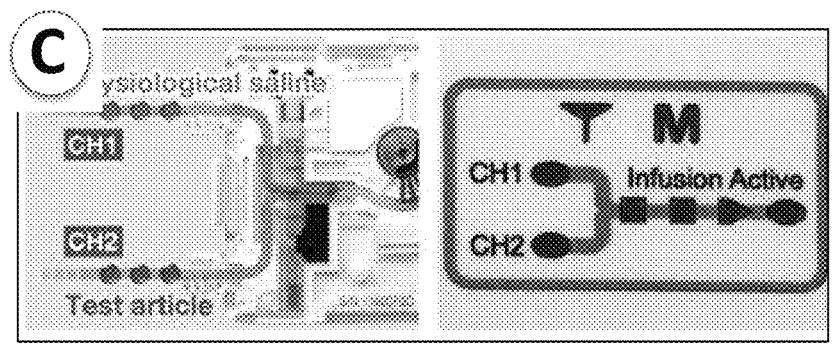
Figure 25D:
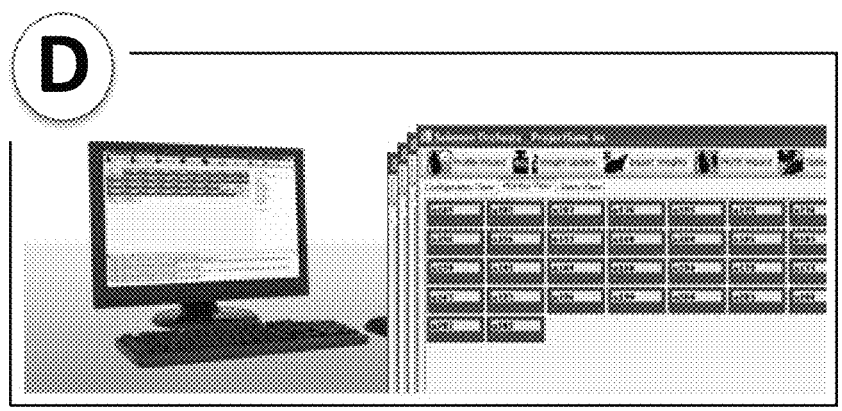

FIG. 24 is a chart showing in vitro I/E induced gene expression.

FIGS. 25A-25D show dual insulin pumps.

Figure 26:
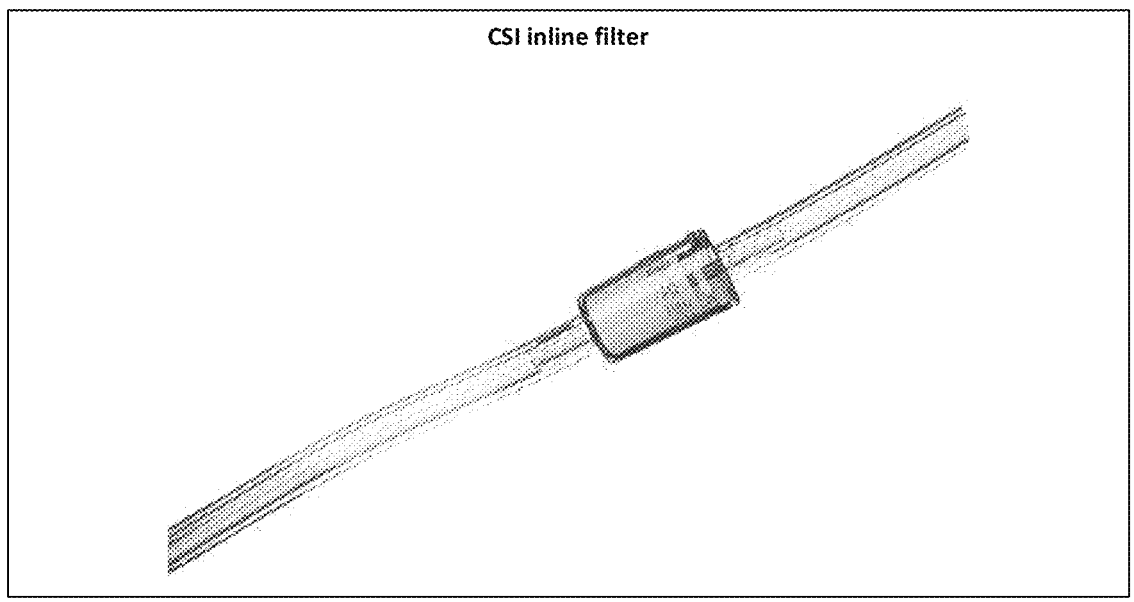

FIG. 26 shows a CSII inline filter.

Figure 27:
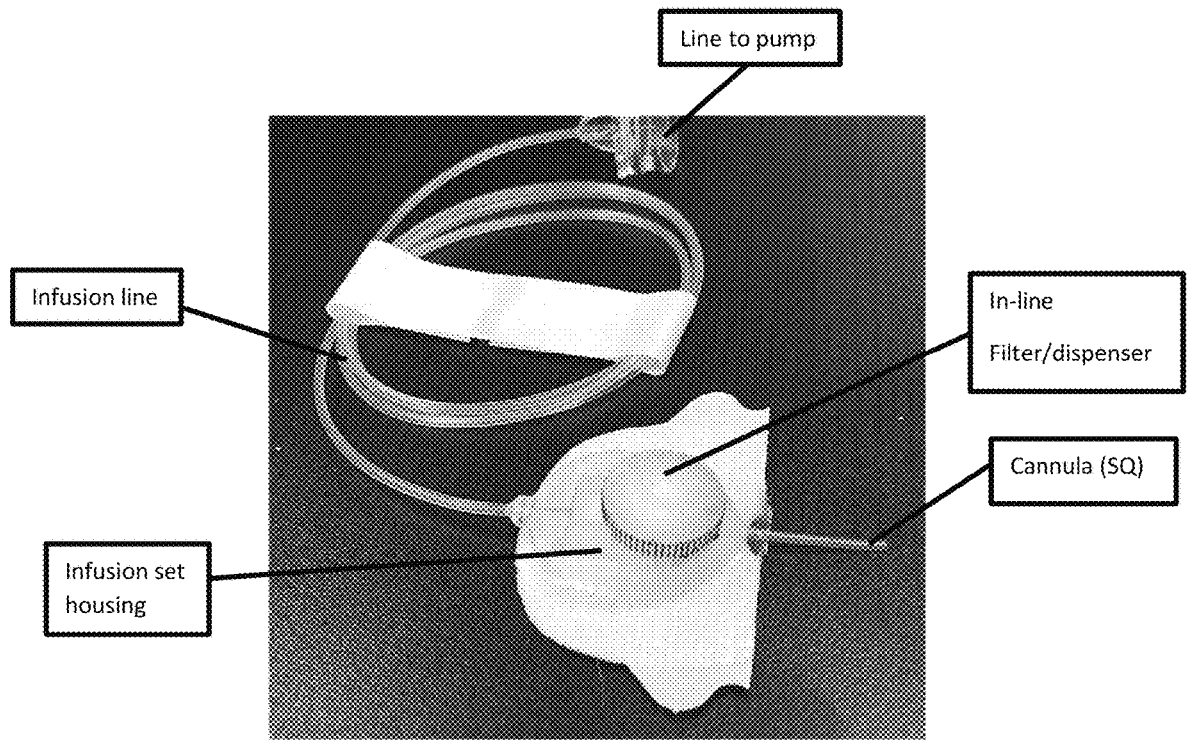

FIG. 27 shows an in-line filter/dispenser device for CSII.

Figure 28:
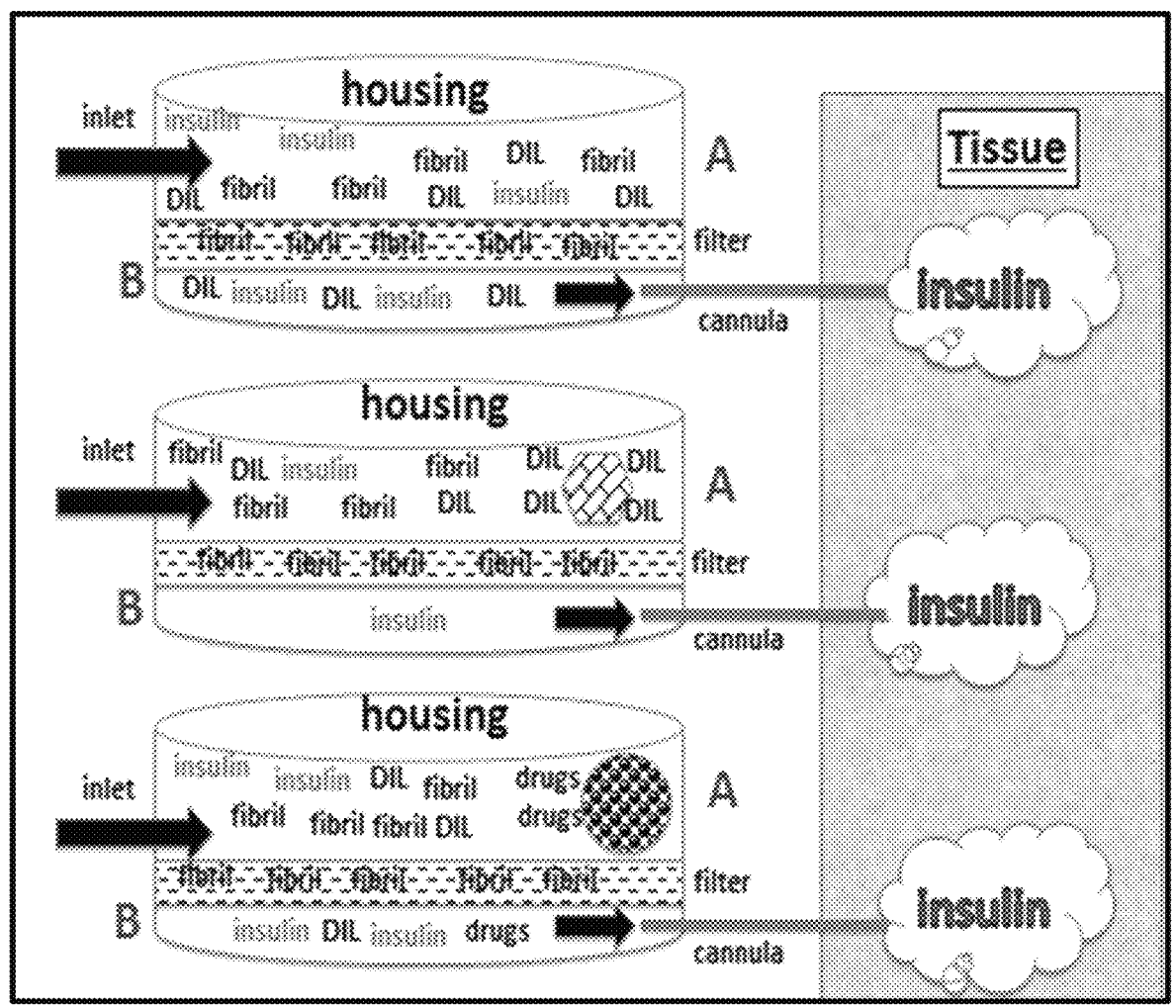

FIG. 28 shows the effect of filters on fibrils, insulin and diluent.

Figure 29:
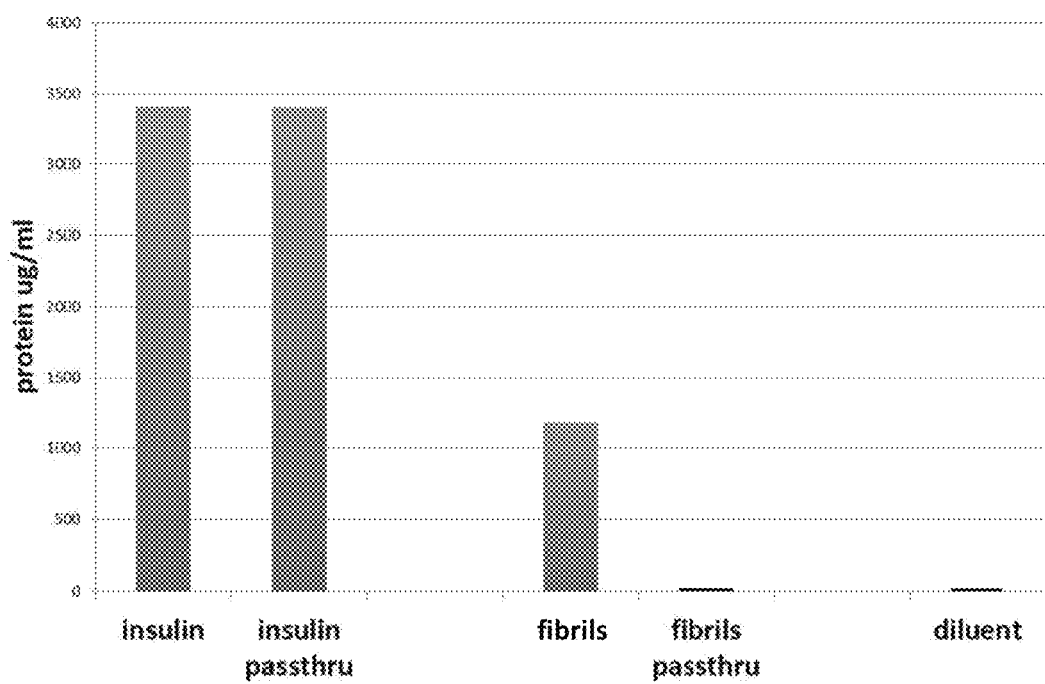

FIG. 29 is a graph showing uses of a filtration device (0.2 micron pore size) to remove insulin-fibrils but not insulin in diluent solutions.

FIG. 30 is a table describing test mice.

FIG. 31 is a table describing IFP used in studies described herein.

FIG. 32 is a table describing evaluation of tissue reactions.

Figure 33:
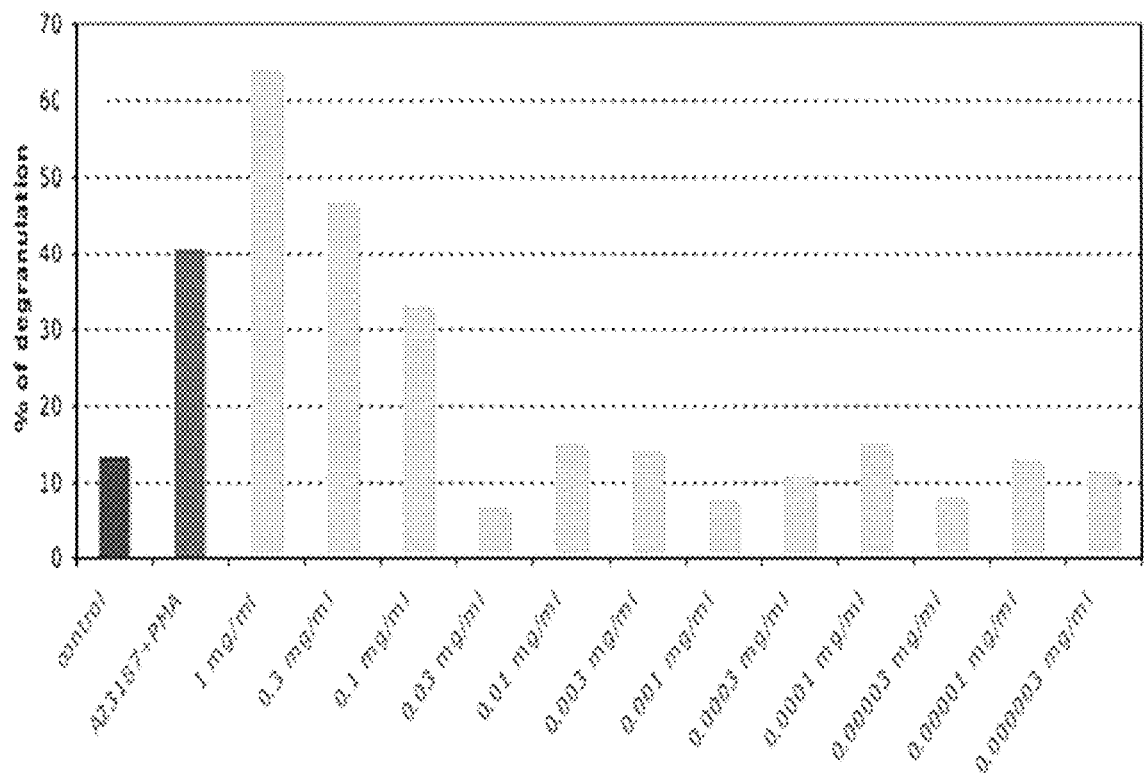

FIG. 33 is a graph showing insulin-induced degranulation of HMC-1 in human mast cells.

FIG. 34 is a table showing MQ/DC depletion models.

FIG. 35 is a chart showing the impact of local drug infusion on IFP tissue reactions and blood glucose regulation.

FIG. 36 is a table of observed tissue and cellular effects after exposure to IFP components.

FIG. 37 is a table of agents used to target certain biological conditions and/or components.

FIG. 38 is a table showing observed tissue and cellular effects after exposure to IFP components.

Figure 39:
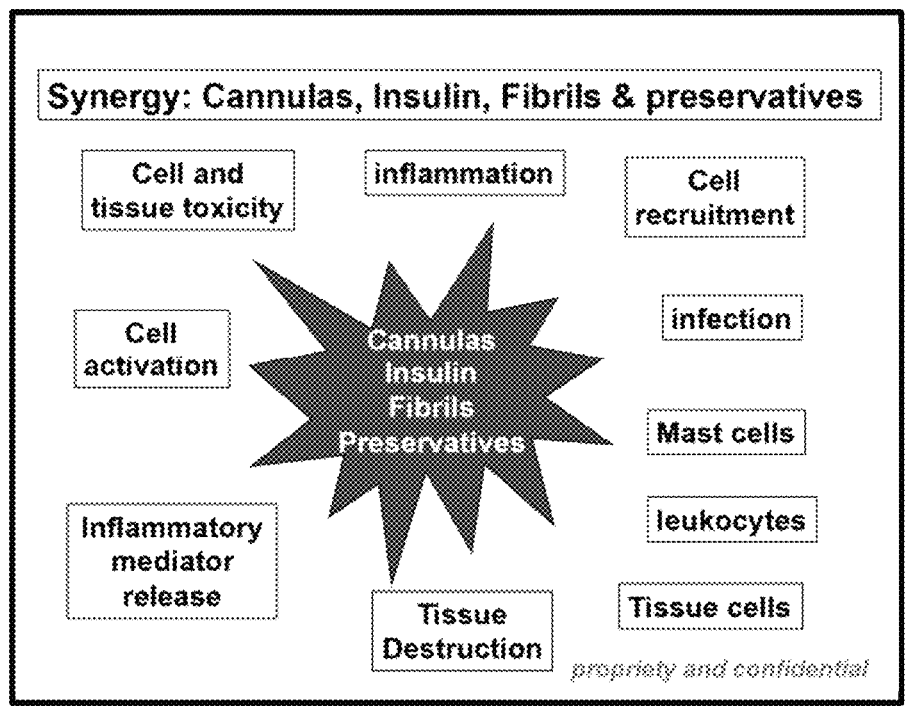

FIG. 39 is a table schematic drawing showing the effects of insulin, fibrils and preservatives on tissue surrounding a cannula.

Figure 40:
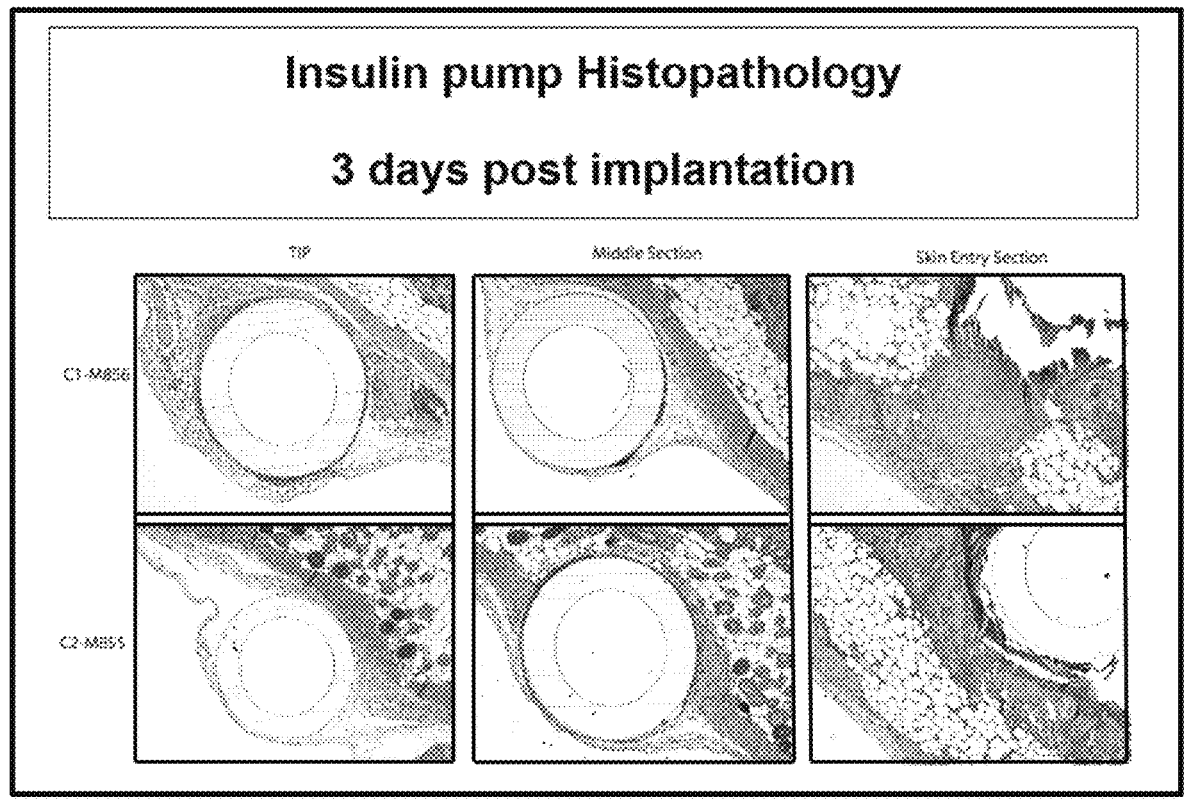

FIG. 40 is a set of photomicrographs showing the impact of an insulin pump on tissues 3 days post implantation.

Figure 41:
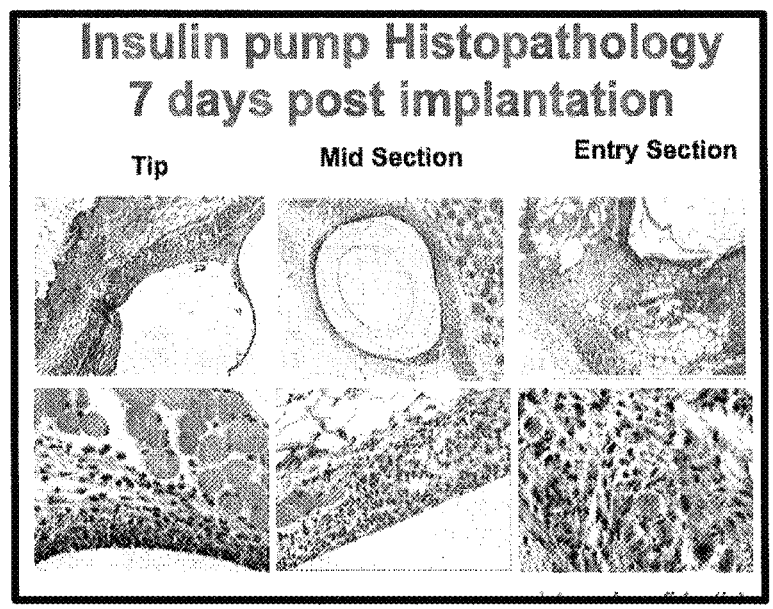

FIG. 41 is a set of photomicrographs showing the impact of an insulin pump on tissues 7 days post implantation.

Figure 42:
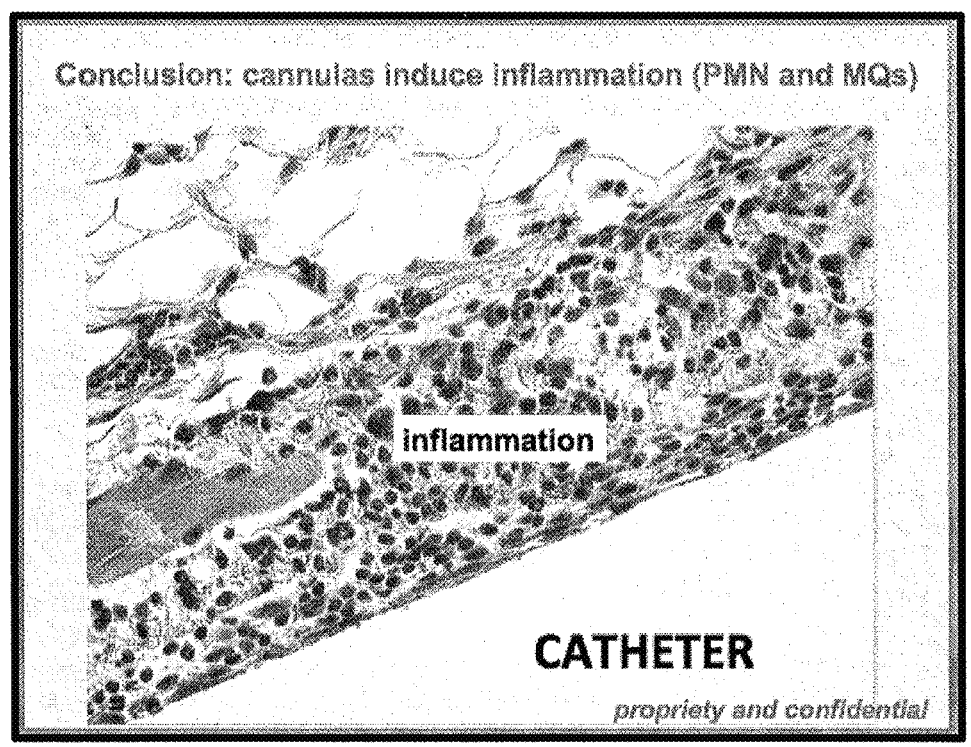

FIG. 42 illustrates tissue inflammation caused by a cannula.

FIG. 43 is a graph showing total cell number for various cell types in vivo in mice based on exposure to various diluents or saline.

Figure 44:
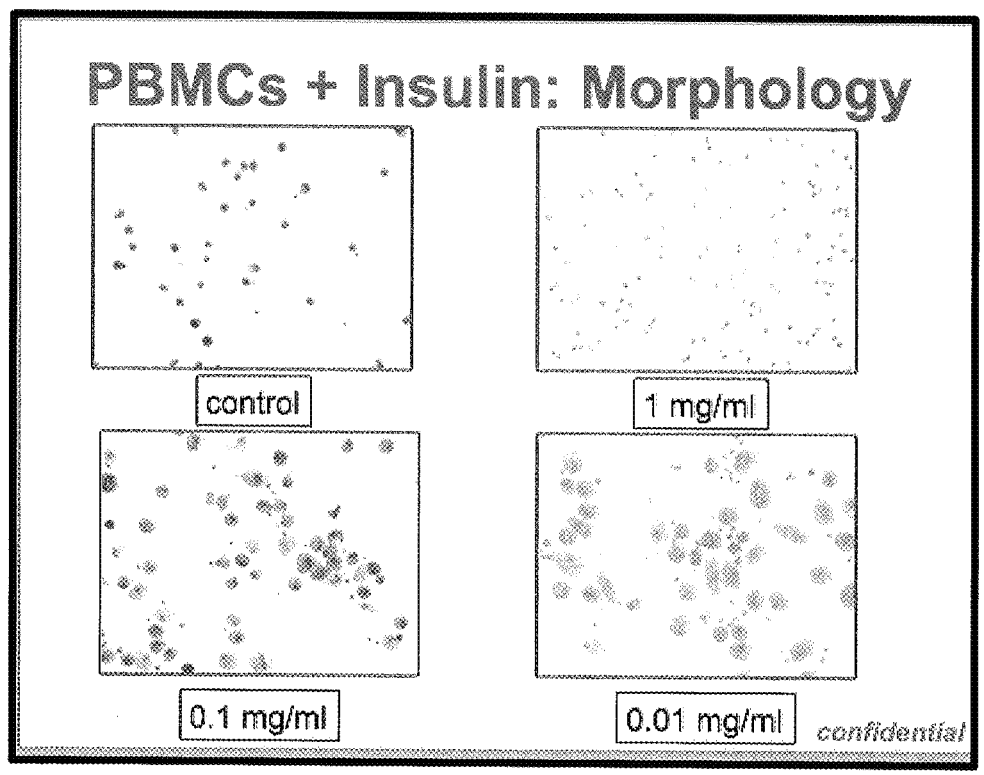

FIG. 44 is a set of photomicrographs showing PBMCs+Insulin-morphology.

Figure 45:
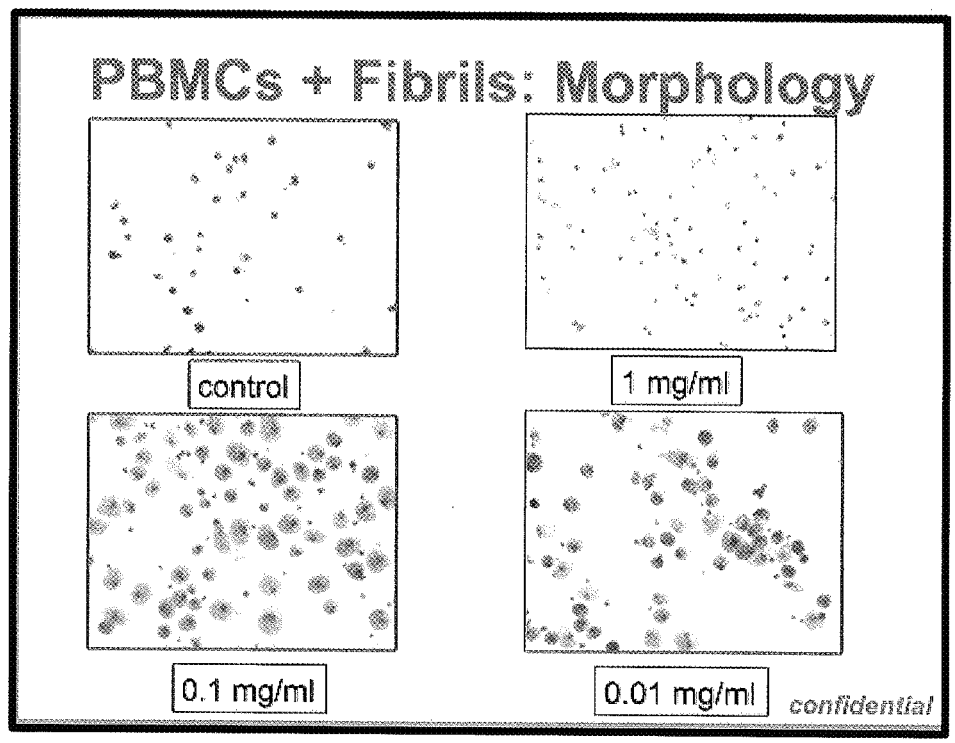

FIG. 45 is a set of photomicrographs showing PBMCs+fibrils-morphology.

Figure 46:
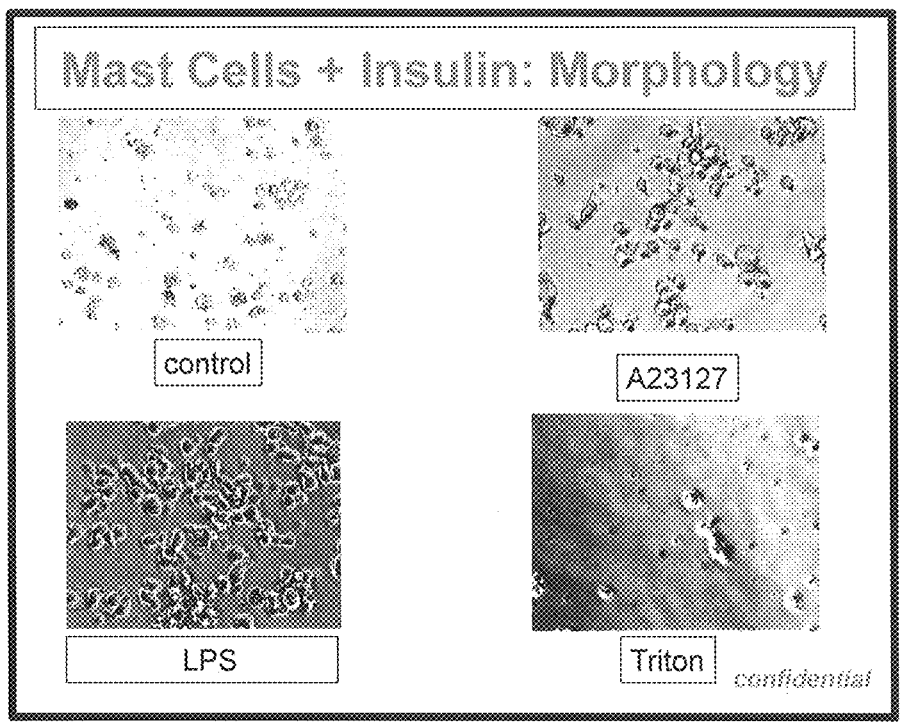

FIG. 46 is a set of photomicrographs showing mast cells+Insulin-morphology.

Figure 47:
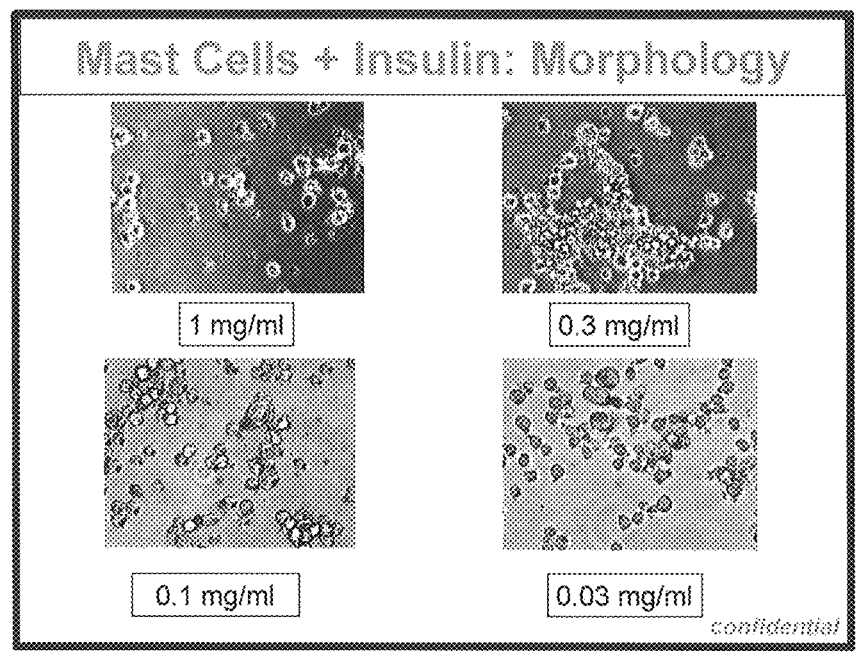

FIG. 47 is another set of photomicrographs showing PBMCs+insulin-morphology.

Figure 48:
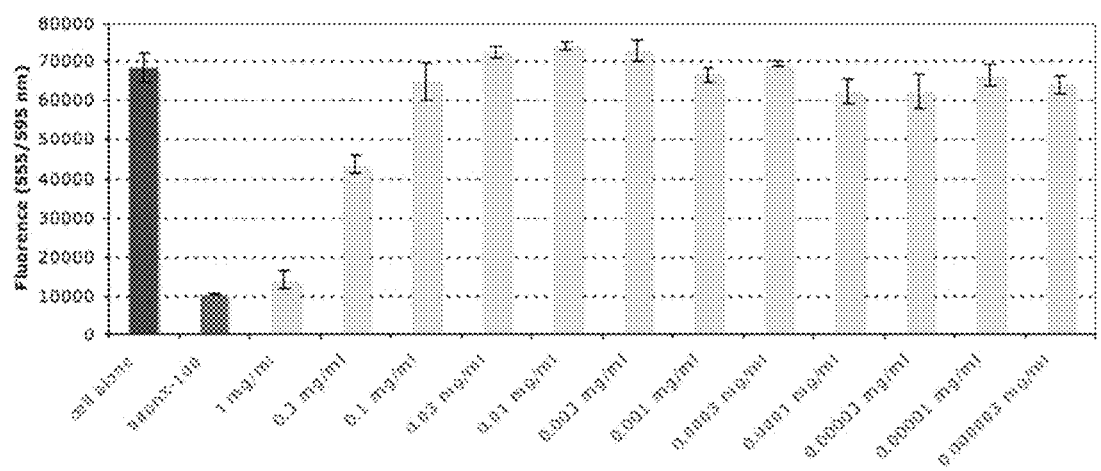

FIG. 48 is a bar graph showing insulin and mast cell viability at various concentrations.

Figure 49:
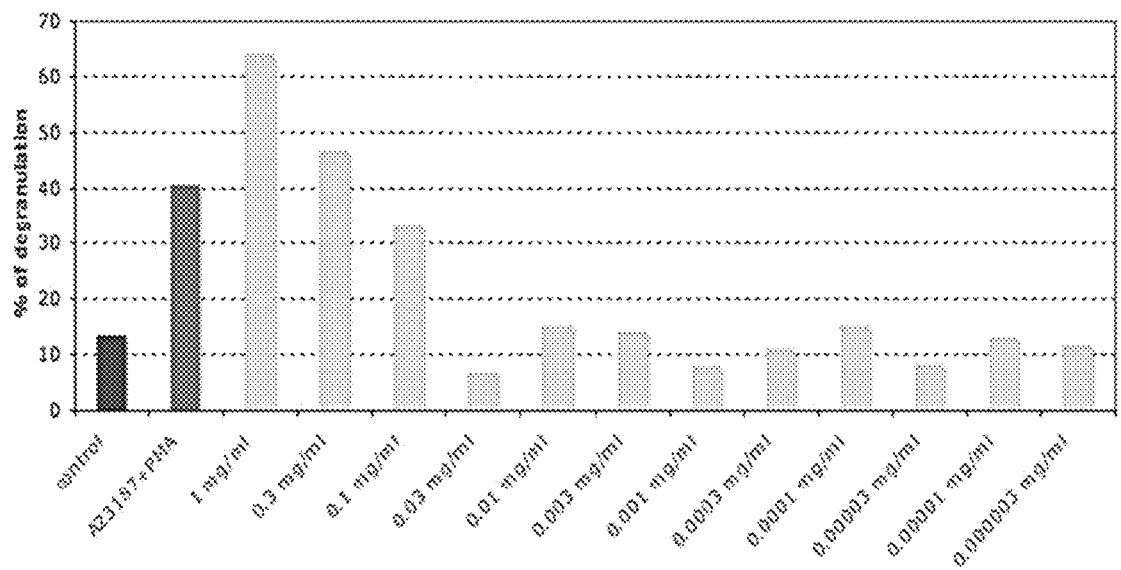

FIG. 49 is a bar graph showing insulin induced degranulation of HMC-1 human mast cells.

Figure 50A:
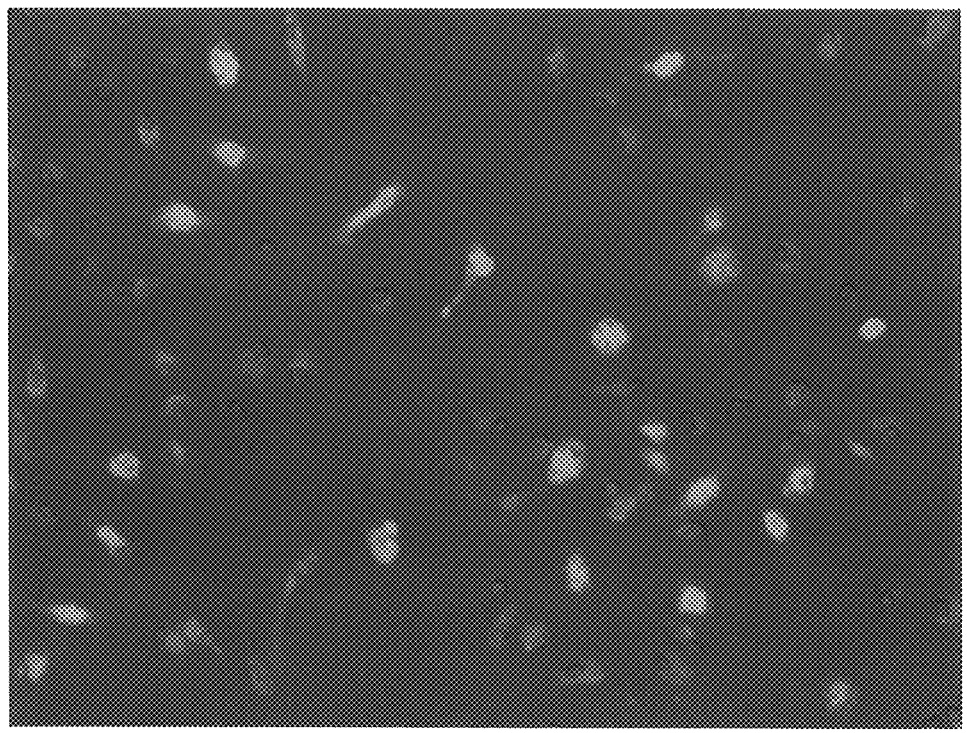
Figure 50B:
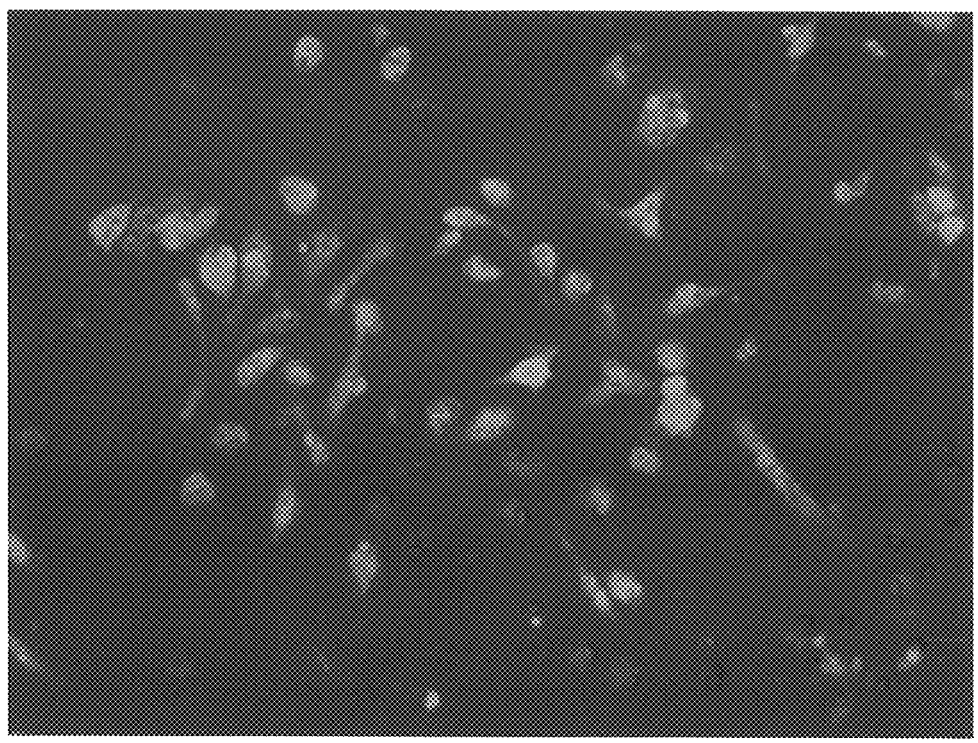

FIGS. 50A and 50B are bright light (50A) and fluorescence (50B) photos for mouse MQs plus GFP insulin study.

Figure 51A:
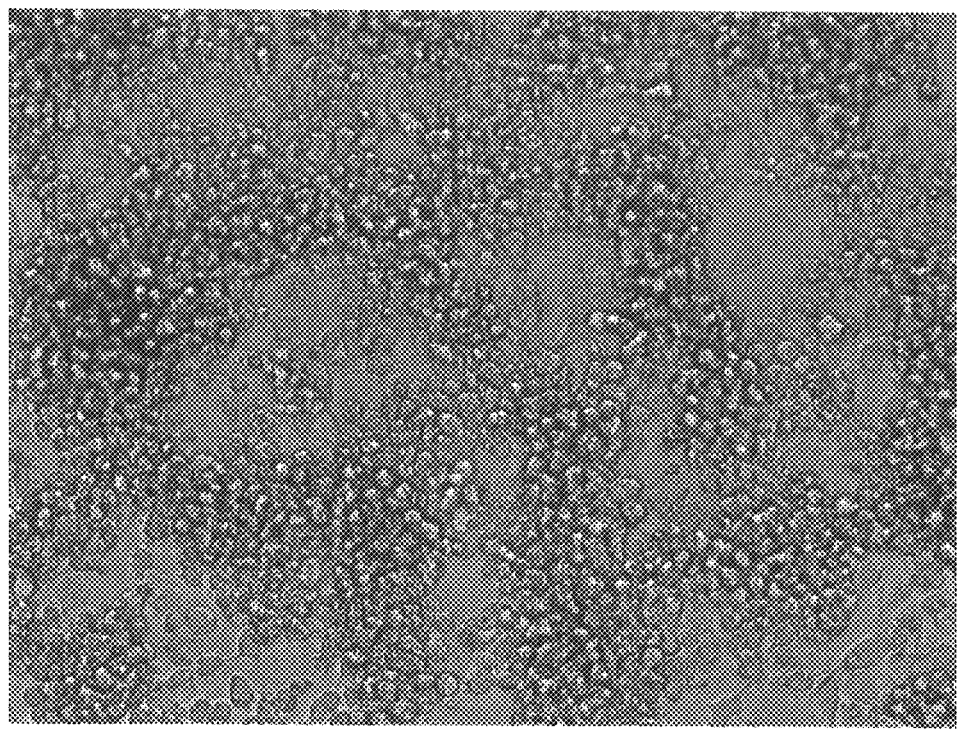
Figure 51B:
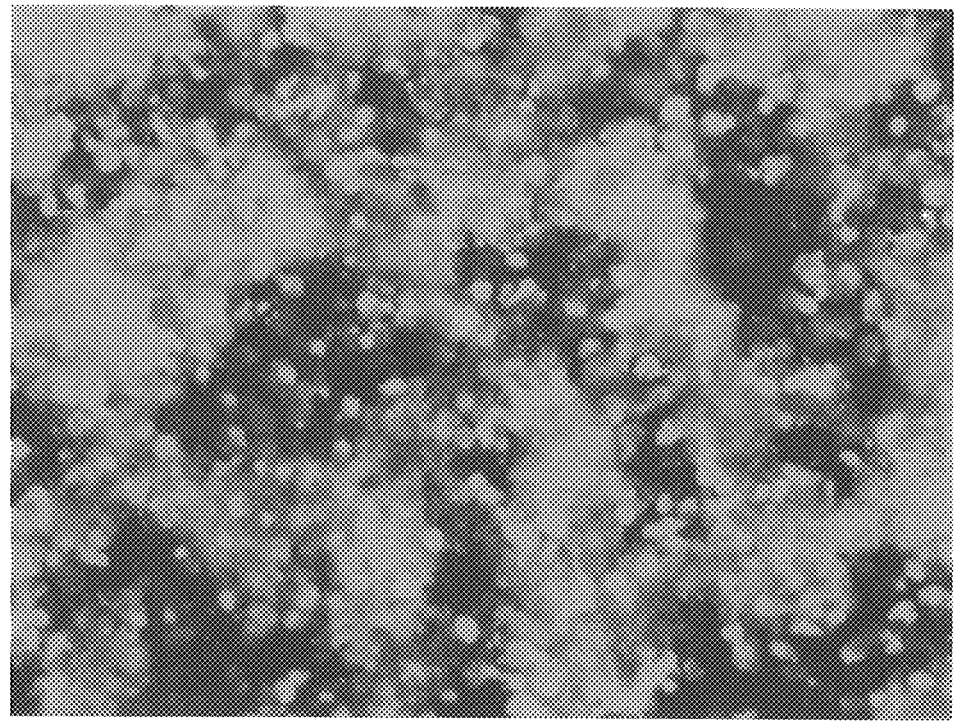

FIGS. 51A and 51B are bright light (%1A) and fluorescence (51B) photos for mouse MQs plus GFP fibril study.

FIG. 52 is a bar graph showing the effect of insulin and its preservatives on human neutrophils.

FIG. 53 shows the effect of leukocytes and leukocyte proteases on insulin.

Figure 54:
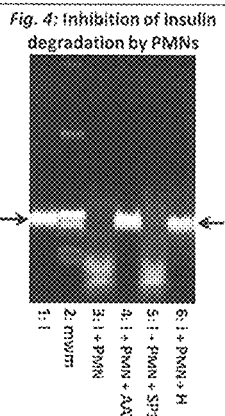

FIG. 54 shows the effect of inhibitors on insulin degradation.

Figure 55A:
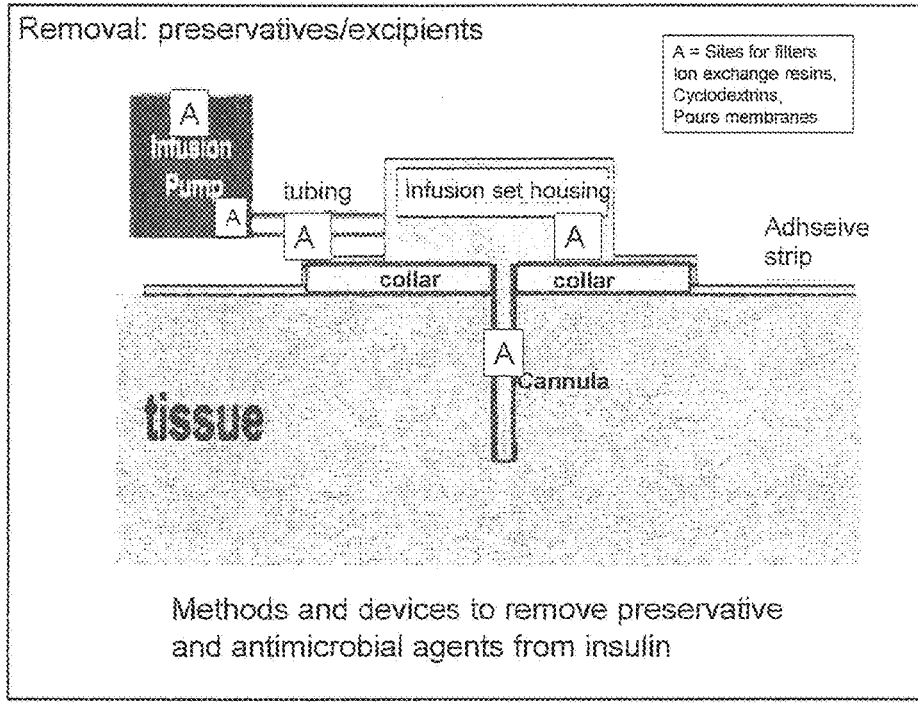

FIG. 55A shows devices and methods for removing preservative and antimicrobial agents from insulin.

Figure 55B:
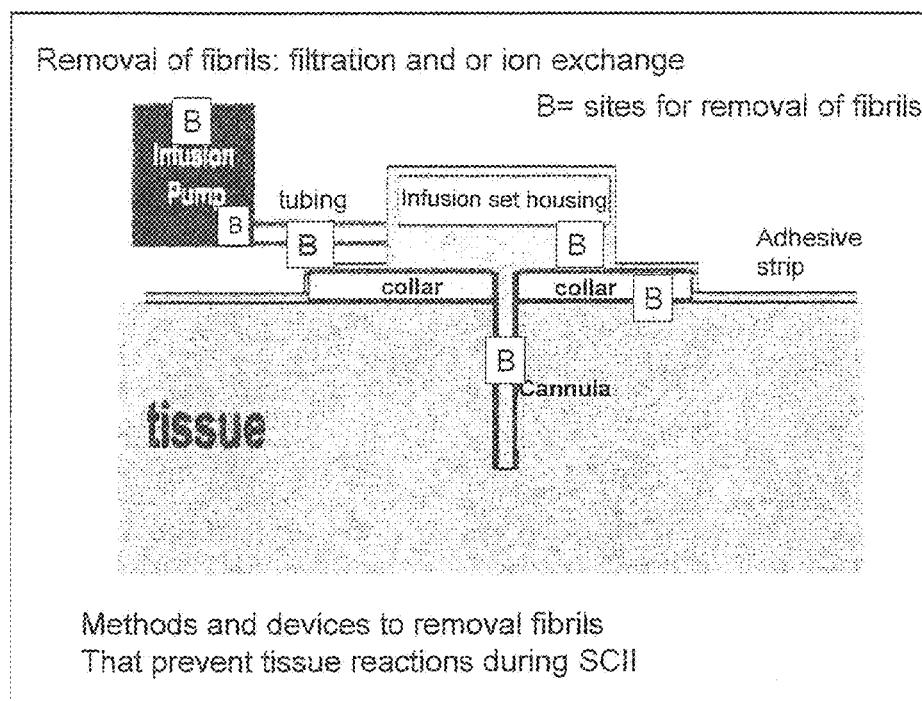

FIG. 55B shows devices and methods for removing fibrils during SCII.

Figure 55C:
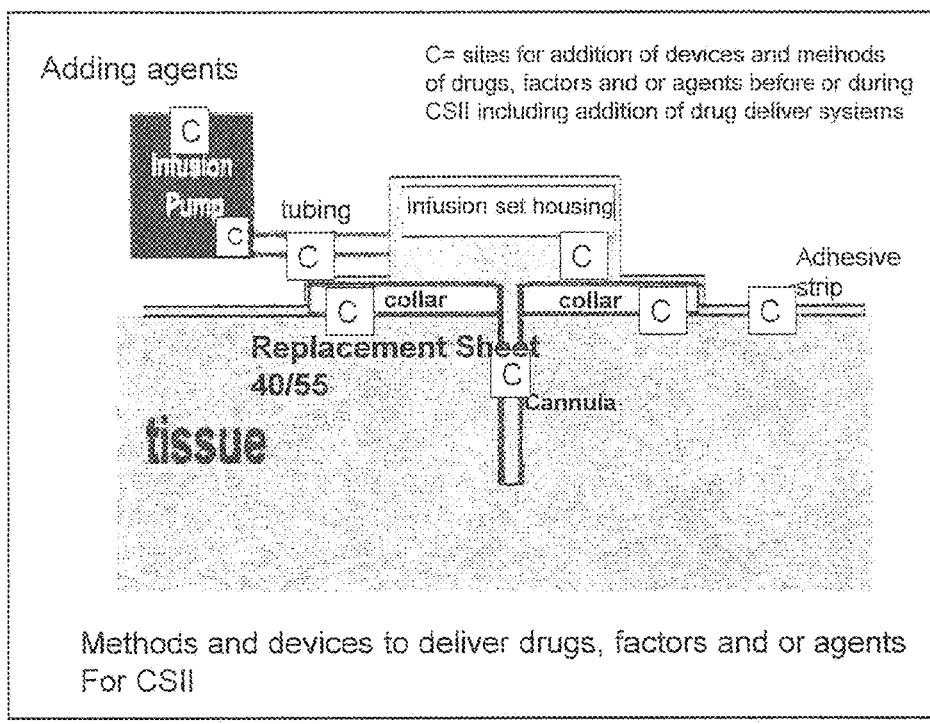

FIG. 55C shows devices and methods for delivering drugs, factor, and/or agents for CSII.

Figure 55D:
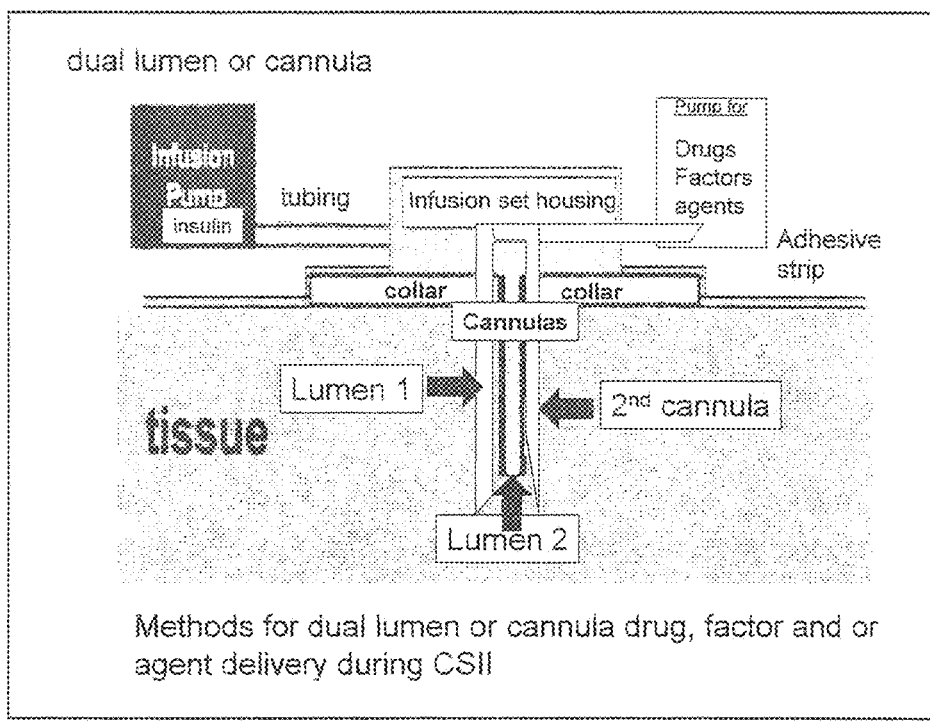

FIG. 55D shows method for dual lumen or cannula drug, factor and/or agent delivery during CSII.

Figure 55E:
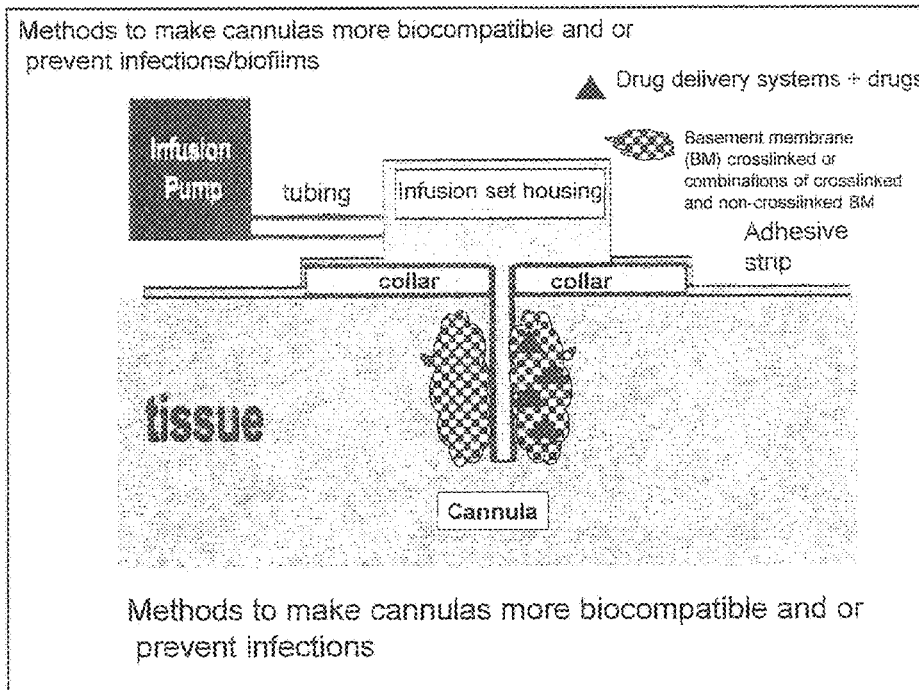

FIG. 55E shows methods and devices to make cannulas more biocompatible and/or prevent infections.

Figure 55F:
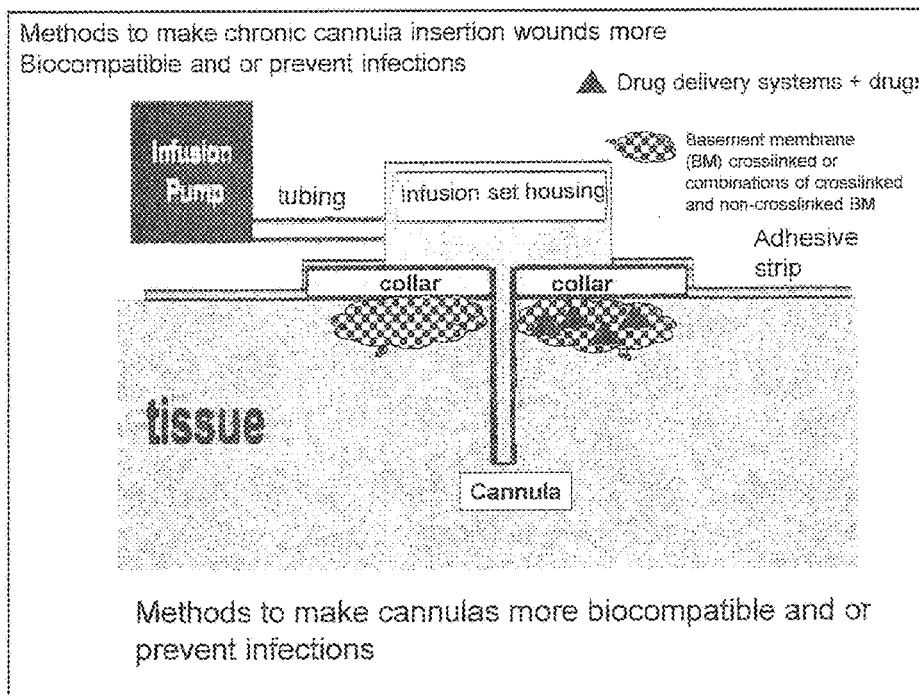

FIG. 55F shows additional methods and devices to make cannulas more biocompatible and/or prevent infections.

Figure 55G:
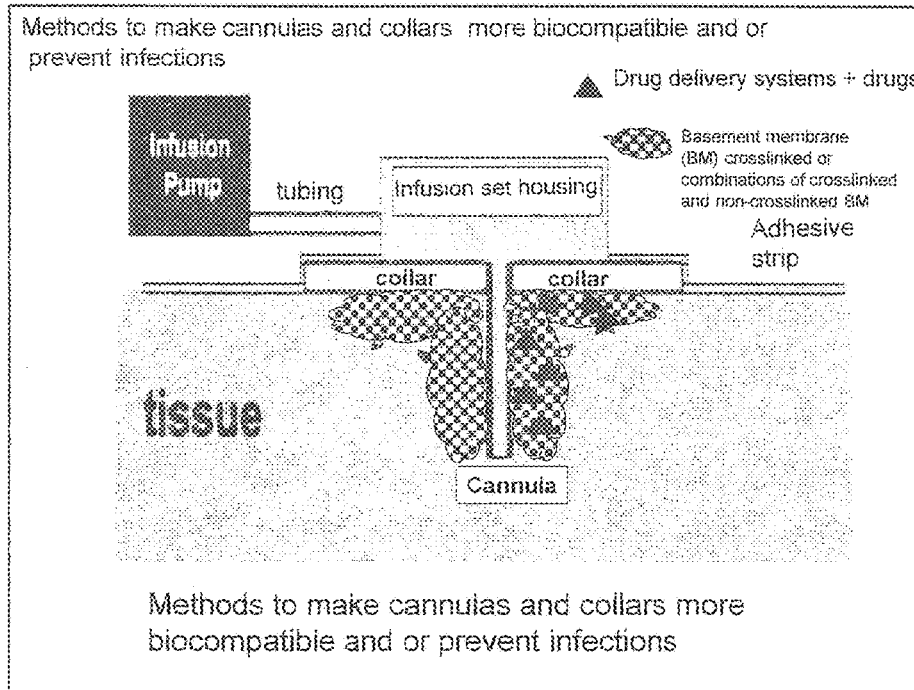

FIG. 55G shows methods and devices to make cannulas and collars more biocompatible and/or prevent infections.

Figure 55H:
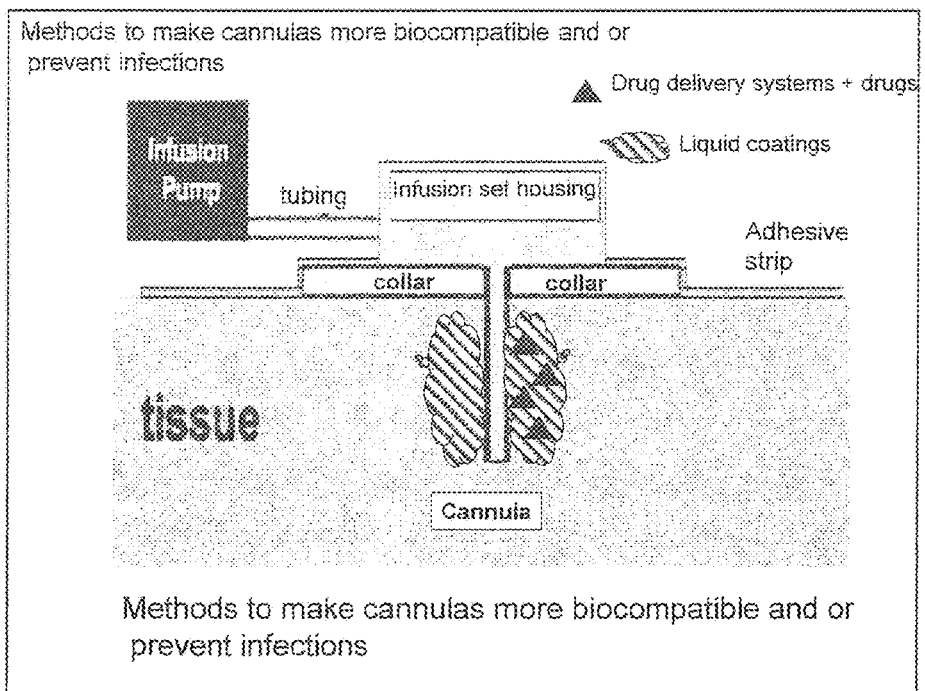

FIG. 55H shows further methods and devices to make cannulas more biocompatible and/or prevent infections.

Figure 55I:
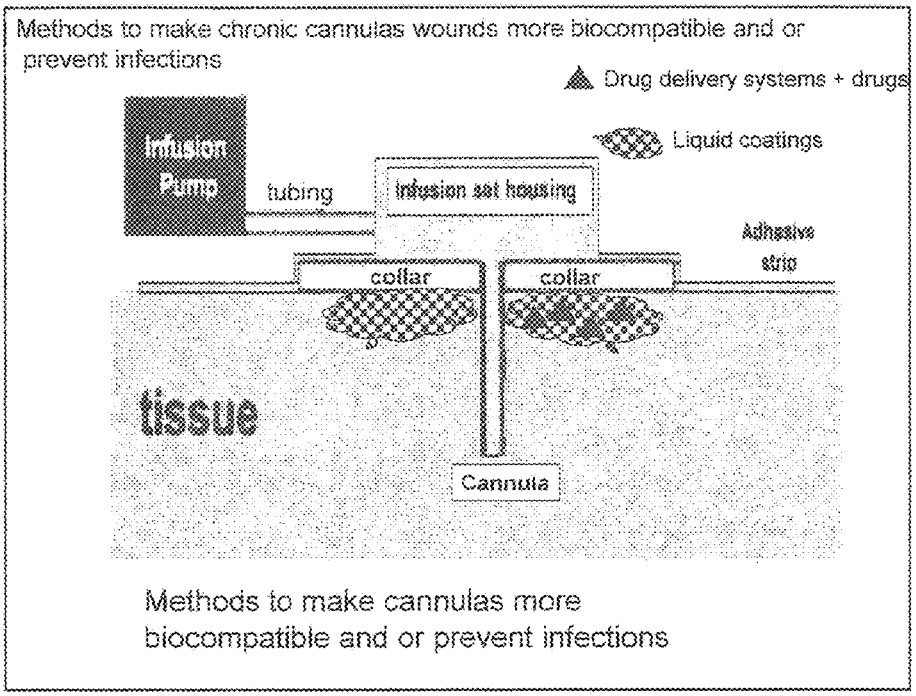

FIG. 55I shows more methods and devices to make cannulas more biocompatible and/or prevent infections.

Figure 55J:
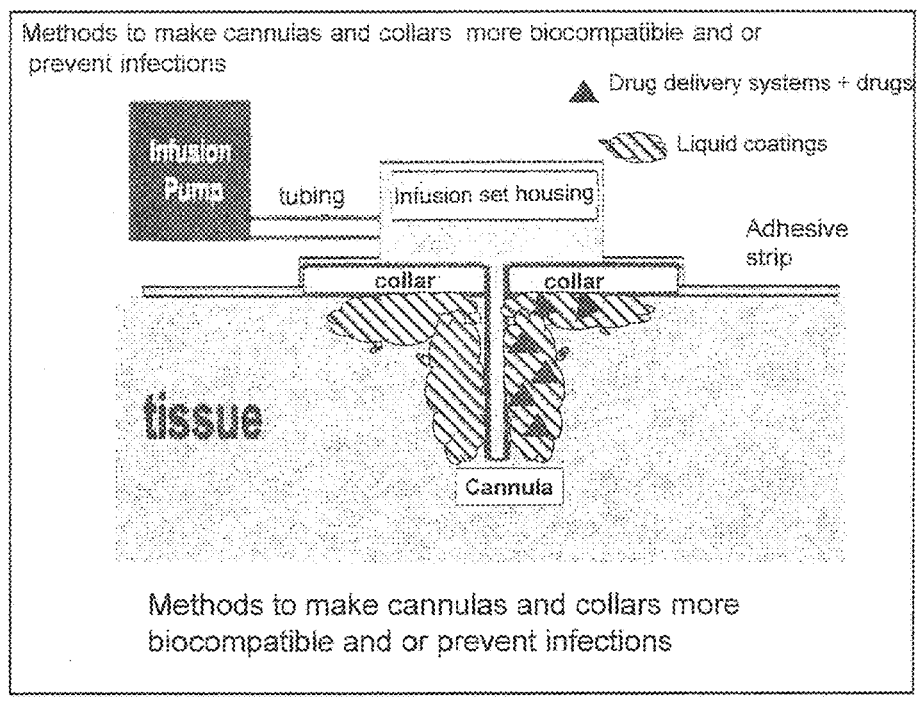

FIG. 55J shows additional methods and devices to make cannulas more biocompatible and/or prevent infections.

Figure 56A:
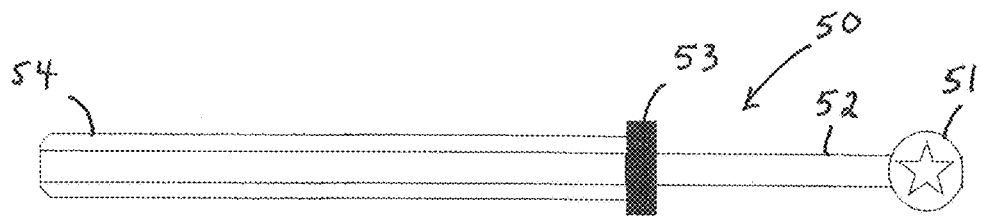

FIG. 56A shows a conventional cannula.

FIGS. 56B-56F show cannulas incorporating filters and/or absorbing materials.

Figure 57A:
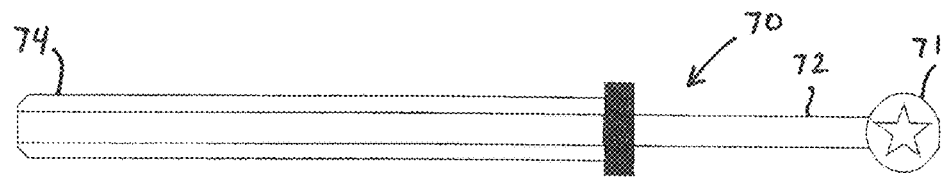

FIG. 57A shows a conventional cannula.

FIGS. 57B-57F show cannulas incorporating drugs, factors and/or agents.

Figure 58A:
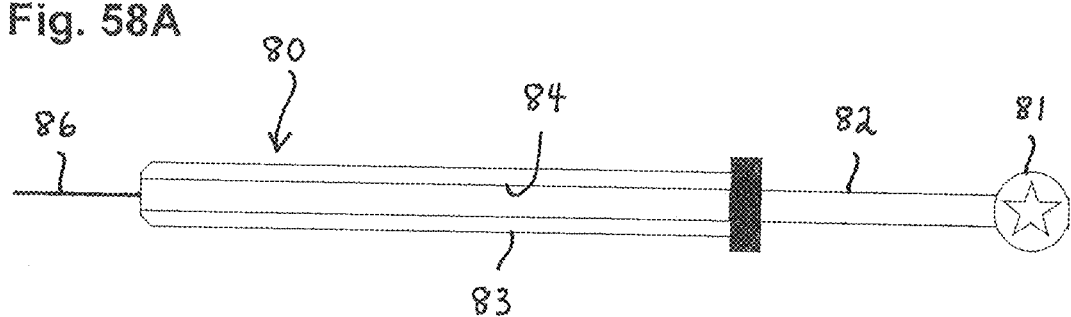

FIG. 58A shows a conventional syringe used to deliver insulin.

FIGS. 58B-58F show syringes incorporating filters and/or absorbing materials.

Figure 59:
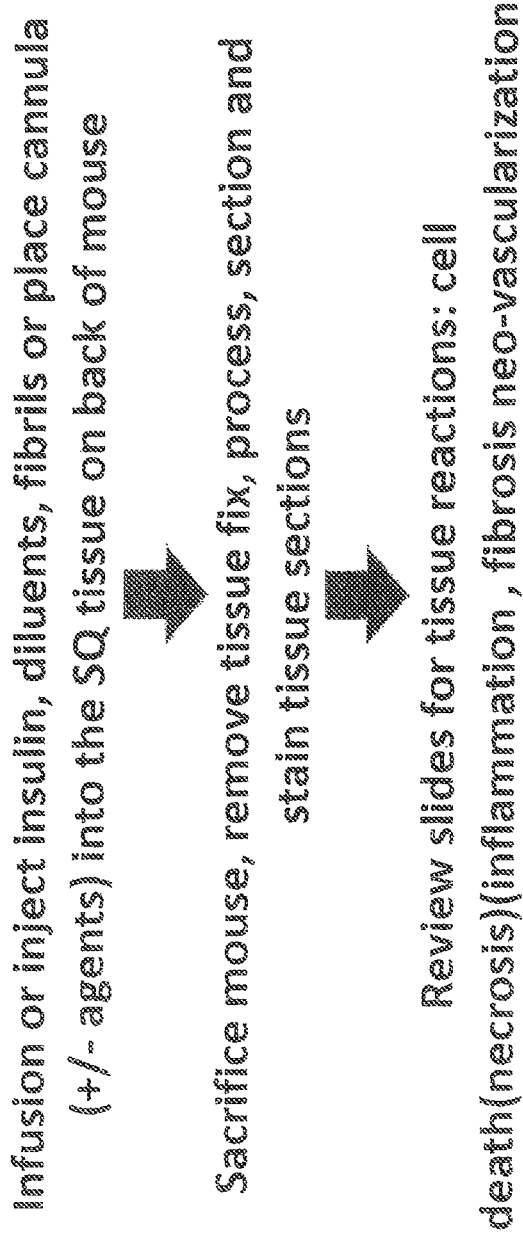

FIG. 59 is a flow chart for in vivo evaluation of cannula, insulin diluent or fibril biocompatibility in a mouse SQ model.

Figure 60:
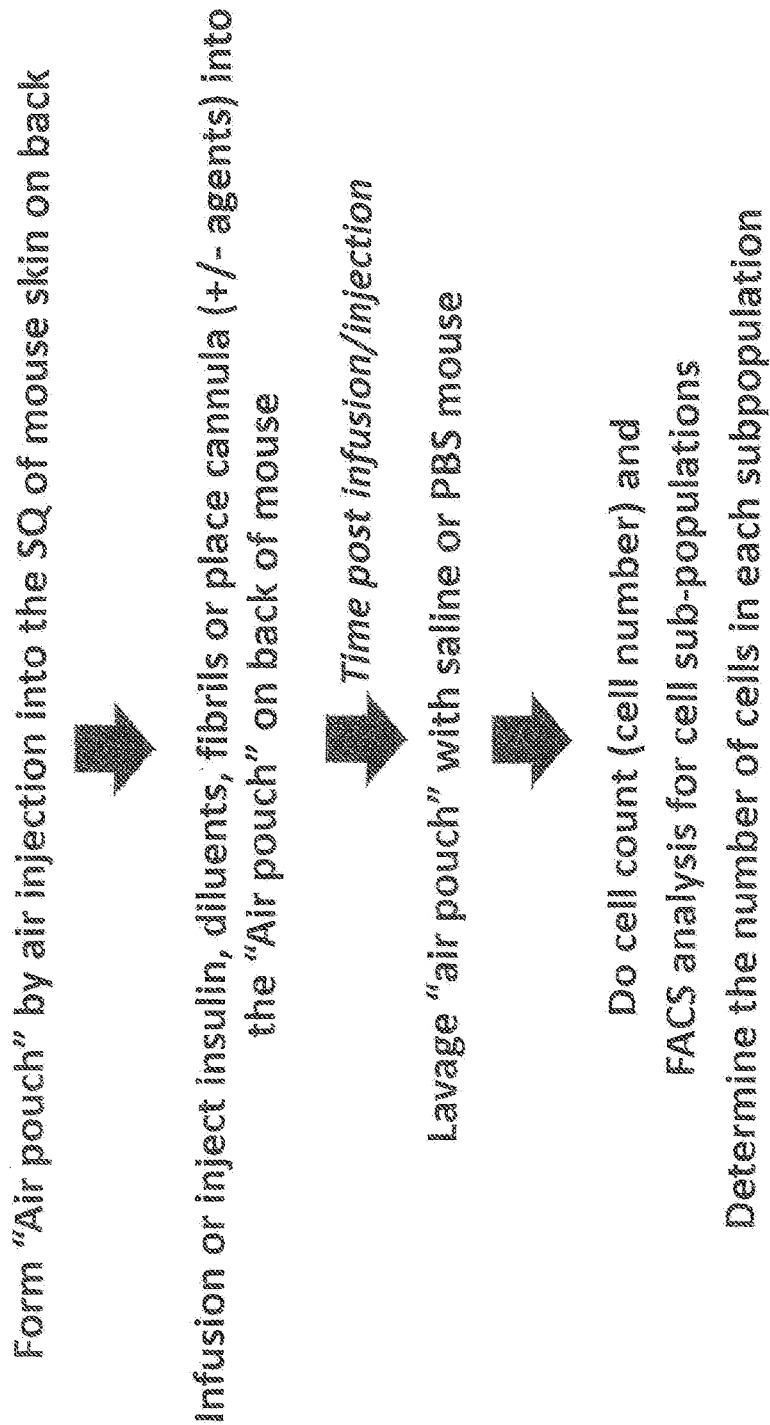

FIG. 60 is another flow chart for in vivo evaluation of cannula, insulin diluent or fibril biocompatibility in a mouse SQ model.

Figure 61:
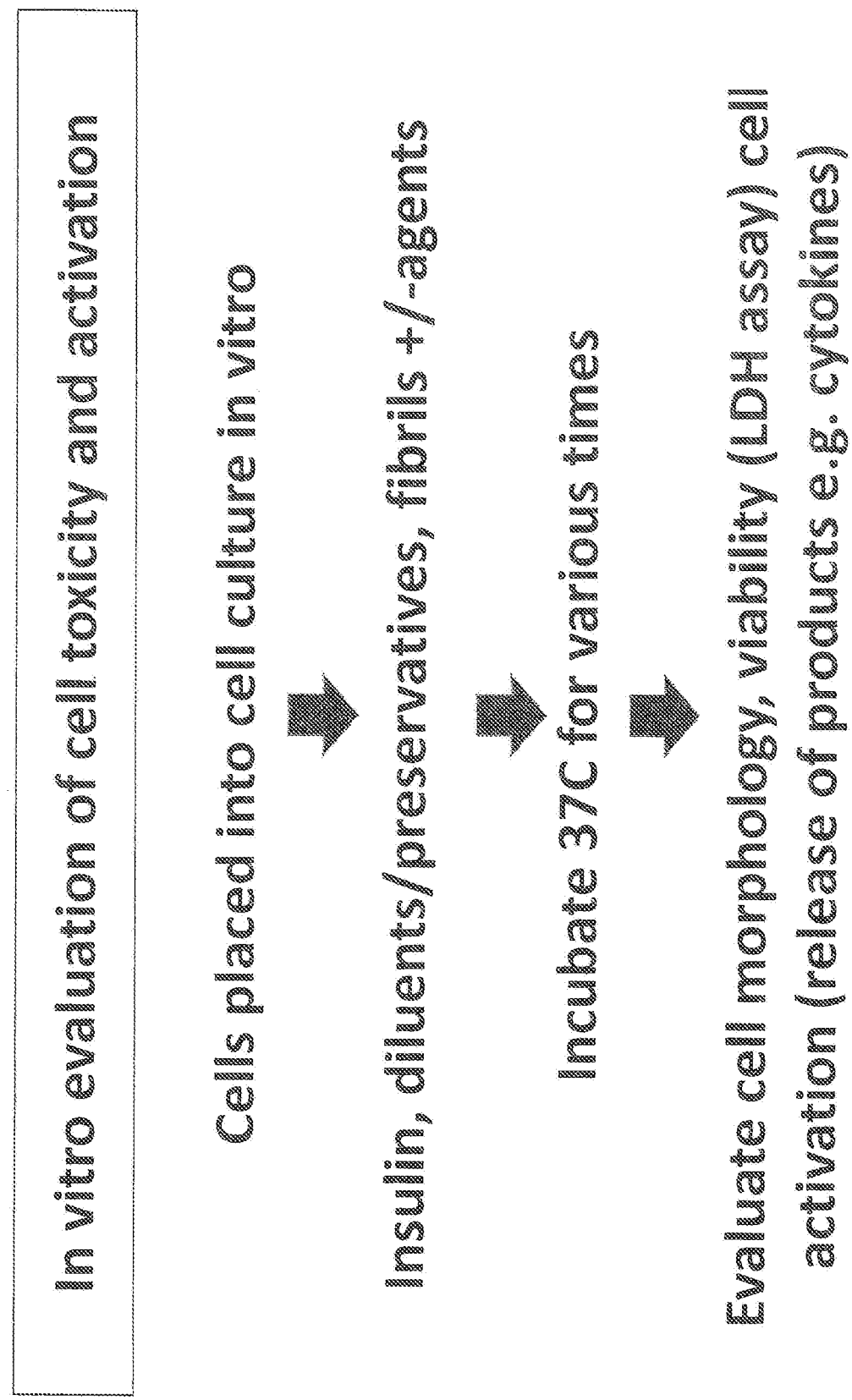

FIG. 61 is a flow chart for in vitro evaluation of cell toxicity and activation.

Figure 62:
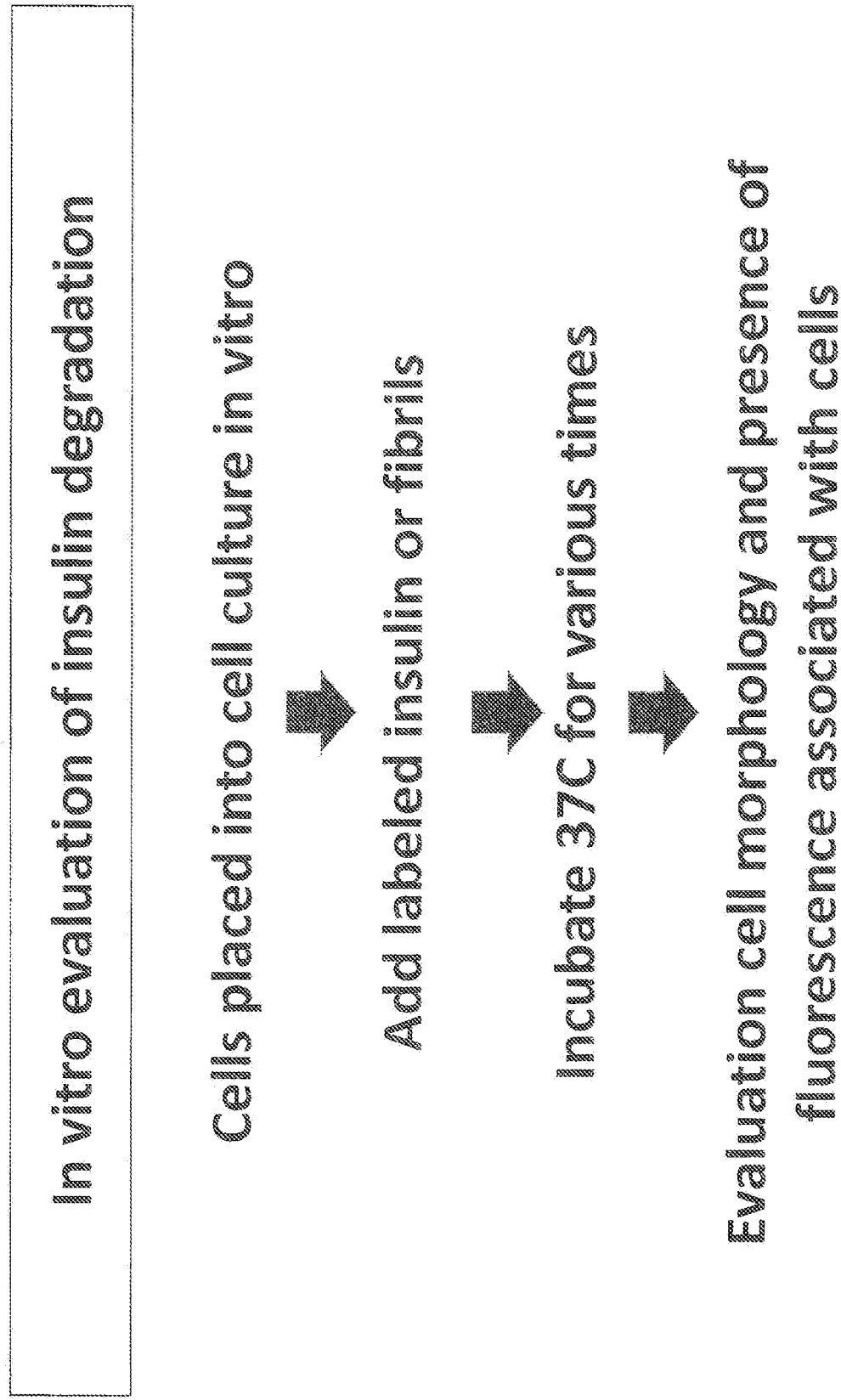

FIG. 62 is a flow chart for in vitro evaluation of insulin degradation.

Figure 63:

FIG. 63 is a flow chart for in vitro evaluation of inhibition of insulin degradation.

Figure 64:
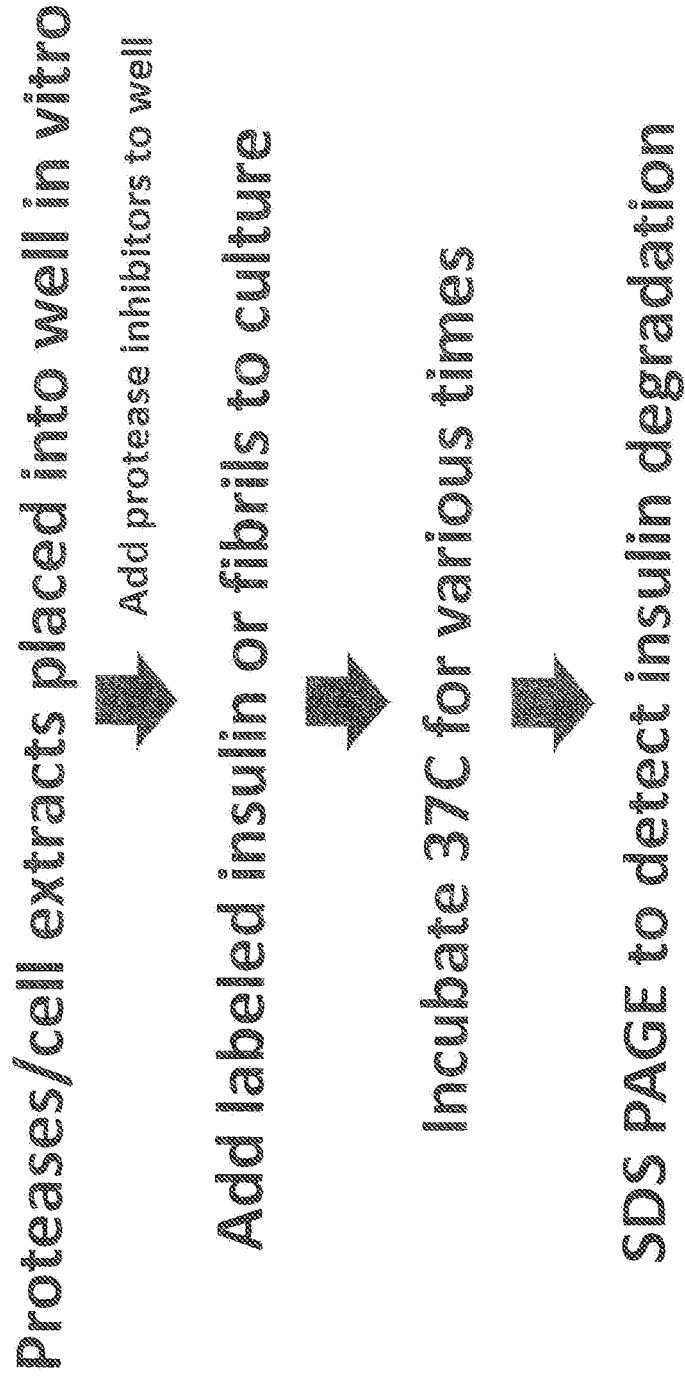

FIG. 64 is a flow chart for in vitro evaluation of inhibition of insulin degradation by proteases and cell extracts.

DETAILED DESCRIPTION

Insulin infusion remains one of the least studied, but most critical elements of an integrated artificial pancreas (AP) system. Successful AP system requirements include the need to maintain precise and accurate in vivo delivery of very minute and continuously variable amounts of insulin in response to changing blood glucose (BG). Additionally, the physical absorption and BG response to infused insulin should remain constant permitting stable AP algorithm performance. Interestingly, little was known in the past about the impact of insulin excipients/diluents and continuous subcutaneous insulin infusion (CSII) failures including loss of blood glucose regulation.

Embodiments disclosed herein solve problems associated with insulin/excipient induced tissue reactions during CSII and syringe delivery of insulin. We have found that insulin infusion triggers tissue injury and local inflammatory responses at insulin infusion sites, which ultimately results in limited infusion site longevity, premature infusion failure and PK absorption variability. We also have found that IFP trigger tissue injury and local inflammatory reactions (inflammation and fibrosis) both during infusion and afterwards (i.e. after cannula withdrawal), that ultimately limit infusion site longevity, infusion failure and PK absorption (FIGS. 1A and 1B). Furthermore, based on the data described herein, we understand that insulin formulations containing phenol and/or m-creosol (excipients/diluents) trigger infusion site tissue injury and local tissue reactions (inflammation and fibrosis), occurring during both infusion and afterwards (i.e. after cannula withdrawal). The consequences of these diluent induced tissue reactions include limiting Embodiments infusion site longevity (short and long term), premature infusion failure and pharmacokinetics (PK) absorption variability. based on our present data we believe that the influx of chemokine-recruited leukocytes into the infusion site, results in the release of leukocyte-derived proteases that degrade insulin. Insulin degradation will further limit the effectiveness of insulin mediated BG regulation in vivo (FIG. 1). We further understand that inhibitors of cytokine, chemokine and leukocyte proteases will decrease infusion site inflammation, tissue injury and thereby improve both short-term (decrease inflammation) and long-term (decrease fibrosis) CSII performance and BG regulation in vivo.

One embodiment described herein uses an adsorption technology such as ion exchange resin to reduce the concentration of at least one of fibrils, and insulin preservatives from an insulin solution before the insulin is administered to a patient. Non-limiting examples of suitable adsorption resins include ion exchange resins include nonfunctionalized hyper-cross-linked polymer Macronet MN200 and two ion exchange resins, Dowex XZ (strong anion exchange resin) and AuRIX 100 (weak anion exchange for removal of phenols in water treatment). Another embodiment described herein uses a cyclodextrin-containing component (or another absorbing component) to remove at least one of insulin fibril and insulin preservatives from an insulin solution before the insulin is administered to a patient.

Example 1—In Vivo Model for Measuring Tissue Reactions

Currently commercial insulin formulations contain phenol, m-cresol or a mixture of both, to stabilize insulin in vitro. We have demonstrated that phenol/m-cresol are not only cell and tissue toxic, resulting in tissue injury and inflammation, but are also able to induce expression of 1) pro-inflammatory cytokines 2) chemokines (directly and indirectly via cytokine mediated induction of chemokines), as well as 3) insulin degrading proteases (see preliminary data section). Translation of these observations into clinically meaningful strategies and treatments requires the development of quantitative in vivo models. Developing and validating these in vivo models is critical to developing effective strategies and therapies to overcome failure of CSII to sustain insulin based BG regulation in vivo. To this end we have modified the classic murine "air pouch" model for evaluation of inflammatory agents and inhibitors to evaluate diluent induced tissue reactions and BG regulation. For this model, sterile air was injected subcutaneously into mouse skin creating a sustained compartment (pouch) for injection of test agents (FIG. 2). At various times post-air/post-agent injection, the "air pouch" can be lavaged, and the cell and fluid content removed and characterized using standard technology (FIG. 2). After lavage, tissue reactions in the air pouch walls can also be determined using standard histopathology/immunohistochemistry (FIG. 2). Using this model we have demonstrated that injection or infusion of diluent into the "air pouch", using human insulin pumps, induces significant inflammation when compared to saline infusion. We have extended this model by replacing the traditional insulin infusion pump system with a wireless totally implantable pump (Iprecio totally implantable pumps, Alzet inc) by converting it into a transdermal pump for uses in murine CSII (FIG. 3). This conversion was achieved by mounting the pump on the back of the mouse using a bio-jacket or running a line from the Ipericio pump into the mouse skin (see preliminary data below (FIG. 4). As such, the pump is not implanted under the skin. Thus, limiting an excessive trauma or inflammation. We have also added our murine CGM system to create a murine "open loop" system (i.e. "air pouch" CGM/CSII model).

Example 2—In Vitro Cell Studies

For these in vitro studies, generally either human or mouse leukocyte cells or cell lines were cultured in vitro in the presence or absence of insulin preservatives or fibrils at various concentrations. at selected times cell viability and or cell activation has (cytokine expression) was determined. The results of these studies are presented below the general work flow for these studies are located in FIG. 61.

FIG. 5 demonstrates decreasing cell viability of human peripheral blood mononuclear cells (PMBC) after 3 days of exposure to increasing concentrations of insulin or insulin diluent/preservatives as measured by Alamar Blue assay. Insulin diluent contains the formulation components of commercial insulin solutions but without the insulin protein itself.

FIG. 6. Toxicity of insulin and fibrils in vitro: Preliminary in vitro morphology of human peripheral blood mononuclear cells (PBMC) after exposure to control media, high (1.0 mg/mL), and low (0.1 mg/mL) concentrations of insulin or insulin fibrils (i.e. insulin degradation byproducts) FIG. 6). Healthy control cells [Left column] show a rounded morphology. Cells exposed to high concentrations of insulin fibril preservatives (IFP) factors [Middle column] show tight contracted morphology indicative of cell death/dying. Cells exposed to low concentrations of Insulin or insulin fibrils factors [Right column] show a spread, expanded morphology indicative of cell injury/activation.

FIG. 7. Our in vitro studies Insulin and excipients induced expression of pro-inflammatory cytokines in PBMC in vitro. Specifically these in vitro studies demonstrated that insulin (+/−preservatives) and preservatives alone, as well as fibrils (data not shown), induce expression of pro-inflammatory cytokines including IL-6, IL-8 and TNFa from PBMC in vitro (IL-8 data presented in FIGS. 7B-D) Summary results for PBMCs is presented in FIG. 7A. Similar data has been obtained with human cell lines (THP-1) and mouse macrophages (MQ). This supports our belief that I/E can induce inflammation in vivo, and that chronic infusion of IFP can cause chronic inflammation and fibrosis.

For these studies we utilized the work flow described in FIG. 61. FIG. 7B shows the impact of insulin and fibrils on cytokine expression by human PBMCs in vitro. At physiologic concentrations, both insulin formulation and insulin fibrils are toxic for human cells in vitro. FIG. 7C shows insulin induced activation of Human PBMCs in vitro: IL-8. The Protocol was: Hu-PBMC+insulin (72 hr)=>Assay Interleukin 8 (IL-8). FIG. 7D shows insulin induced activation of human PBMCs in vitro: IFN-g. The Protocol was Hu-PBMC+insulin (7 days)=>Assay Interferon gamma. This data clearly demonstrates that insulin, diluents and fibril cause pro-inflammatory activation of these cells in vitro. The in vivo activation of these cells would cause inflammation and tissue destruction resulting in loss of effective CSII function.

Example 3A—"Open Loop" Mouse Model—In Vivo

The "airpouch" model was prepared and evaluated as presented in the workflow diagram in FIG. 60. FIGS. 8A-8D. Combined CSII and CGM mouse model (A B, C). Non-obese diabetic (NOD) mouse implanted with Abbott Navigator glucose sensor (GS) and a short polymer infusion set for CSII. The set and sensor were placed sufficiently far apart to avoid interference. Open Loop CGM and CSII insulin infusion system cage and assembly, that allows animal ambulation and mobility during simultaneous continuous glucose sensing and insulin infusion. FIG. 8D is an example of CGM blood glucose levels (blue line) and external BG control tests (red diamonds), monitored in a diabetic NOD mouse that received periodic insulin infusion (bars present at the top of FIG. 8D). These studies demonstrate the successful open loop BG control in our murine model of CSII and CGM.

Example 3B—In Vivo Data—Tissue Reactions to CSII Insulin and Diluents

Tissue toxicity of insulin in vivo: Injection: Saline control tissues manifest minimal infiltration of inflammatory cells. Diluent treated tissues demonstrate substantially higher levels of inflammatory cells, potentially due top inflammatory activation and recruitment in the injection site, as is shown in FIG. 19, which compares a saline control to a diluent. FIG. 19 shows H & E stained sections of a mouse skin and subcutaneous tissue after 3 consecutive 2X daily injections of saline or insulin diluent.

FIG. 9. Tissue Toxicity of Insulin in vivo: Infusion: The sectioned polymer catheter wall is visible and marked with a black asterisk (*) in all tissues. Darker colored zones (marked with a black I) in the diluent and insulin infusion sample indicate the presence of extensive cell damage, inflammation and cellular infiltrate at the infusion site immediately surrounding the infusion catheter. Infusion was accomplished using the open loop delivery system described in FIG. 5. It is important to note that the insulin infusion cannula alone (i.e. saline infusion did not induce tissue reactions thus indicating the reactions seen with insulin infusion are not related to the cannula.

Example 3C—Tissue Toxicity of Multi-Diluent Injections; Tissue Reactions to CSII Cannulas For these studies he workflow diagram described in FIG. 59 was utilized. FIGS. 40-42. (saline vs. diluent) These figure shows that multiple injections of diluent, but not saline, cause major inflammatory reactions at injection sites on mouse skin. As is shown in the figure, saline control tissues manifest minimal infiltration of inflammatory cells (dark dots). Diluent treated tissues demonstrate substantially higher levels of inflammatory cells potentially due to inflammatory activation of recruitment to the injection site.

The purpose of these studies was to demonstrate that the cannula alone (not infusion of fluids) would induced tissue reactions that would compromise SCII. Thus, we need to coat the cannulas with more biocompatible substances (like claims) so the cannula alone would not damage the tissue.

FIG. 40 shows low to high power magnification of the implantation site for the cannula showing that cannulas induce inflammation on the entire length of the cannula (labeled tip middle and skin entry point) after 3 days implantation in in 2 mice. This demonstrates that the cannula along triggers inflammation the entire length of the cannula as well as the entry point of the cannula thru the skin thus to prevent this you would coat the cannula with materials that would enhance biocompatibility alone or with the incorporation of agents in those coating agents. It also demonstrates that there is tissue injury and inflammation at the entry point of the cannula thus having infusion set collars (with or without impregnated agents to reduce inflammation and tissue reactions as well as infections would be extremely important to extending the lifespan of the infusion sets in vivo. 7 day data is shown in FIG. 41. FIG. 42 shows inflammation next to the catheter.

Example 4—"Air Pouch/Open Loop" Mouse Model

Leukocyte Influx into Air Pouch Model to Evaluate Tissue Response to Saline or Insulin Excipient The air pouch model (FIG. 60) has been used for the evaluation of tissue responses to tissue irritants and/or for the evaluation of tissue reaction inhibitors. We adapted this model for the evaluation of tissue responses to infusion of insulin, excipients, factors, drugs and control solutions (e.g. saline). An example of air pouch model response to infusion of saline or insulin excipient is present in FIG. 2. Initially, CD-1 mice received air injections (3 mL) into the dorsal site of the low back to induce the air pouch in each animal. On the following day individual mice received infusions of either saline or insulin diluent. The infusion rate for both fluids was infused at 6 units/hr. (equivalent to insulin infusion volumes) for 3 consecutive days into the air pouch. At the end of that time period mice were anesthetized and the air pouch cavity was washed three times with 2 mL pyrogen-free PBS. Exudate was then centrifuged and a TC10 automated cell counter determined the total viable leukocyte cells. The potential inflammatory effect of insulin diluent was evaluated through the analysis on the mouse leukocyte count and exudate concentrations in the inflamed air pouch cavity. Diluent infusion over a 3-day period caused an average of 7-10 fold increase in the total leukocyte count when compared to saline treated air pouch (FIG. 10). Cytocentrifuge/H&E staining of these cell populations indicated that at 3 days post infusion, approximately 60% of the leukocyte present were PMN and 40% mononuclear cells, predominately macrophages. Additional studies of saline vs. excipient infusions indicated that at 4 days post infusion the predominate leukocyte in the lavage were mononuclear and again predominately macrophages (i.e. >80% macrophages). This data clearly demonstrates that diluent causes a significant increase of inflammatory cells and that these reactions evolve from a PMN dominated inflammation to a macrophage dominated tissue reaction. Similar results were obtained in other non-diabetic mice (e.g. B6.V-Lepob/J and C57BL/6).

Example 5—Mouse Air Pouch Model

Using cells obtained from "air pouch" models (FIG. 60) by lavage, we demonstrated that diluents and insulin which contains diluents, but not saline, cause tissue reactions characterized by the influx of PMNs, monocytes and macrophages.

FIG. 43 shows total cell number for treatments with various diluents and saline, demonstrating insulin preservative/diluent induced inflammation in a normal CD-1 mouse using a modified "air pouch" model. Air was injected subcutaneously into the mouse skin creating a sustained compartment (pouch) for injection of diluent or saline (control). The diluent and the control agent (saline) were infused continuously for 7 days at a rate of 5 units equivalents/hour one day post air pouch creation. After 7 days of infusion, the air pouch was lavaged. The resulting fluid was characterized for cell number (auto-hemo-cytometer), and cell type using fluorescence activated Cell sorting (FACS). Consistently, diluent treated preservative mice demonstrated a dramatically higher cell count when compared to saline infused mice. Additionally, Neutrophil, Monocyte/Macrophage and Lymphocyte counts were significantly higher in the diluent/preservative infused mice when compared to the saline treated mice. This data demonstrates that diluents cause major inflammatory reactions when infused into the air pouch model, but saline do not cause inflammatory reactions. Since the major components in diluent (preservatives) is phenol and met-cresol removing these preservatives would prevent inflammation seen when they are infused into the air pouch of SQ tissue.

Example 6—Histological Evaluation of Tissue Reactions Induced at Air Pouch Infusion Sites by Saline Vs. Excipients In addition to leukocyte counts in the lavage, we also evaluated the effect of saline and insulin infusion excipient on inflammation over a 3-day period (see workflow diagram FIG. 60). Initial histological analysis of the infusion sites demonstrated that leukocyte accumulation was only prevalent in the excipient infused tissue site (FIGS. 11 B, D and F). The predominant leukocytes were PMN and monocyte/macrophages. The saline treated infusion site experienced minimal to no tissue reaction (FIGS. 11 A, C and E). These results confirm the observation that insulin excipient causes significant tissue reaction at site of infusion. The black star (*) in FIG. 11 indicates the location of the air pouch. The individual magnification is listed on each figure (lower left corner). This data directly demonstrates that diluents present in commercial preparations of insulin trigger inflammation in the air pouch model in vivo and thus likely induce the same inflammatory reactions in the subcutaneous tissue when infused during CSII in vivo. Example 7—Effect of insulin and its preservatives on human peripheral blood leukocytes For theses in vitro studies we utilized the general worflow diagram presented in FIG. 61.

FIG. 52 shows the number of PMN's surviving after 3 days in buffer+/−a serial dilution of insulin or its preservatives (phenol and m-cresol). Even at a 1:48 dilution, there were significantly fewer cells surviving than in buffer alone. As the concentration increased, the number of cells surviving decreased for both insulin and insulin diluent. As the highest concentration texted (a 1:3 dilution of standard insulin formulations), fewer than 1,000 cells survived, compared to over 100,000 in the buffer solution (estimated from optical density). this data demonstrates that complete insulin (insulin plus preservatives) and preservatives only are toxic to human leukocytes when the leukocytes are co cultured with the insulin or preservatives.

Example 8—Fluorescent Uptake of Insulin into Leukocytes In Vitro

Studies in our laboratories demonstrated that insulin uptake and degradation by inflammatory and tissue cells lowers effective insulin levels, ultimately requiring higher insulin dosages to achieve blood glucose regulation. This added insulin infusion also results in increased tissue inflammation at the infusion site. The aim of this example was to determine whether leukocytes can degrade insulin in vitro. We utilized fluorescent insulin (FITC-insulin; Sigma, St. Louis, Mo.), Humalog insulin, and human peripheral blood leukocytes isolated from diabetic and non-diabetic patients. We cultured leukocyte subpopulations (PMN's, macrophages, and lymphocytes) in vitro+/−f-Met-Leu-Phe (a chemotactic and leukocyte activating factor). We then added FITC-insulin and monitored leukocyte uptake of FITC-insulin using fluorescent microscopy (FIG. 12A, 12B, 12C). inverted microscope and cyto-chemical staining was used to confirm subpopulations that took up FITC-insulin and to assess cell viability with trypan blue and intact nuclei by DAPI staining.

Example 9—In Vitro Insulin Degradation

For these studies we utilized the general workflow diagrams presented in FIGS. 62, 63 and 64.
Role of Leukocytes and Leukocyte Proteases in Limiting Insulin Regulation of Blood Glucose Levels During CSII To characterize the ability of purified proteases or leukocyte extracts to degrade FITC-insulin in vitro we analyzed the impact of cell culture supernatants and cell lysates on insulin degradation using 10-20% SDS-PAGE gels. This was performed+/−anti-protease cocktails to characterize proteases responsible for insulin degradation. The functional activity of individual leukocyte proteases was analyzed using protease PAGE gels+/−protease inhibitors. This study clarifies the role of leukocytes in insulin therapy. (FIG. 13a, 13b, 13c and FIG. 14). Our results show that (1) leukocytes take up and degrade FITC-insulin in vitro, (2) activating leukocytes with f-Met-Leu-Phe increases this degradation, (3) Humalog insulin and insulin-FITC are degraded by leukocyte proteases including neutrophil elastase, trypsin, and insulin-degrading enzyme, and (4) the activity of these proteases can be reduced by natural inhibitors including alpha-1 antitrypsin and aprotinin.

FIG. 53 shows degradation of insulin by leukocyte proteases. Analysis by lane: (1) Insulin appears as a bright band (MW=5.8 kDa), (2) Molecular marker to 2 kDa, 25 kDa and 75 kDa in red, insulin in yellow (what is relative position of yellow—final drawing will be in black and white. (3)Trypsin degrades insulin so that the original band is no longer visible, replaced by two primary degradation products. (4) Elastase cleaves insulin at many sites, leaving a streak of products at a wide range of molecular weights. (5) Insulin degrading enzyme cleaves insulin into several smaller peptides, including a bright band at a low molecular weight. (6) PMNs taken from a Type I diabetic patient and lysed with Triton X100 completely degrade insulin into a wide range of products. Lymphocytes and monocytes taken from human peripheral blood also degraded insulin, although not to the same extent (data not shown). PMNs from non-diabetic patients degraded insulin as well (data not shown). In FIG. 53, I=insulin, T=Trypsin, E=Elastase, IDE=Insulin Degrading Enzyme, PMN=Triton X100 extract of human PMN, mwn=molecular weight marker.

FIG. 12 shows human and mouse leukocytes uptake of FITC-insulin. Our initial in vitro studies demonstrated that FITC-insulin (green) is taken up by human peripheral blood leukocytes such as PMNs (FIG. 12 A) monocytes (FIG. 12B). FIG. 12 is a combined bright field and fluorescence photomicrograph with FITC-insulin appearing green once phagocyte by the individual leukocyte subpopulations (primarily PMN & MQ, but not Lymphocytes (FIG. 12C)). Mouse MQ also uptake FITC-insulin in vitro and degrade FITC-insulin in vitro (SDS PAGE analysis data not shown).

FIGS. 50 A and 50B show mouse MQs plus GFP insulin—FIGS. 51 A (bright light) and 51B (Fluroescence) show mouse MQ plus GFP fibril study.

FIG. 13 shows insulin degradation by cells. Degradation of FITC-insulin by elastase (E) and human leukocyte extracts (LE): To determine whether triton X100 extracts of total human leukocytes isolated from blood could degrade insulin in vitro we incubated FITC-Insulin with LE or +/−HALT (protease inhibitor cocktail (FIG. 13 A), E or +/−aprotinin (elastase inhibitor) (FIG. 13B) E+/−protease inhibitor AAT (FIG. 13C) and analyzed the results by PAGE. LE or E degraded FITC insulin, and this degradation was blocked by the serine protease inhibitor aprotinin (A), HALT and AAT. We have analyzed the ability of various proteases and anti-proteases to degrade insulin and or block degradation of FITC-insulin (FIG. 14). We obtained similar data using Humalog and SDS-PAGE with Coomassie staining (protein staining). These studies demonstrate that leukocytes induced at IFP infusion sites decreases functional insulin levels in vivo, thereby decreasing the effective control of blood glucose levels in vivo. The addition of protease to insulin formulation not only increases insulin effectiveness but also suppresses tissue injury and inflammation.

Example 10—Effect of Anti-Proteases in Inhibiting Insulin Degradation

For these studies we utilized the workflow diagram presented in FIG. 64. In FIG. 54, I=insulin, PMN=Triton X100 extract of human PMN, mwn=molecular weight marker, AAT=alpha-1-antitrypsin, SP16=synthetic short peptide from AAT), H=Halt=AEBSF-HCL+Aprotinin+Bestatin++e-64+Leupeptin+Pep statin A.

FIG. 54 shows PMN degradation of insulin=+/−inhibitors. Analysis by lane: (1) Insulin appears as a bright band (MW=5.8 kDa), (2) Molecular marker to 2 kDa, 25 kDa and 75 kDa in red, insulin in yellow (what is relative position of yellow—final drawing will be in black and white.) (3) PMN extracts completely degrade insulin (as in Lane 6 above). (4) AAT completely inhibits the degradation of insulin; insulin is visible at 5.8 kDa. (5) SP16 fails to inhibit degradation; at higher concentrations, it is able to do so. (6) HALT (anti-protease cocktail) inhibits the degradation of insulin.

In this example, we tested the ability of various anti-proteases to inhibit insulin degradation by leukocyte extracts and proteases. The table in FIG. 14 summarizes the results of these studies. HALT anti-protease cocktail was the only inhibitor to block degradation of IDE. Aprotinin, AAT, SP16, and HALT all blocked insulin degradation by Elastase, Trypsin, and Trion X100 extracts of human PMNs. This shows that addition of anti-proteases to insulin formulations inhibits degradation of insulin in vivo.

Example 11—Impact of Insulin on Mast Cell Morphology—In Vitro

FIGS. 46-47 show the impact of insulin on mast cell morphology. At physiologic concentrations, both insulin formulations fibrils (not shown) are toxic to mouse mast cells in vitro. FIG. 47 shows results based on concentation.

Example 12—Impact of Insulin on Mast Cell Viability and Degranulation—In Vitro

For these studies we utilized the general workflow diagram presented in FIG. 61. FIGS. 48-49 show the impact of insulin on mast cell viability and degranulation. Mast cells (MC) are key skin "sentinel" cells and are generally the first tissue cell population activated by tissue trauma triggering acute inflammatory or allergic reactions and serve a central role in chronic inflammation and wound healing. Recent results from our laboratory indicate that skin mast cells affect glucose sensor induced tissue reactions and CGM function (13). FIG. 48 demonstrates that increasing concentration of insulin causes increasing increasing cell death (alamar Assay) Our data demonstrate that insulin can be MC toxic and activate MCs in vitro (FIG. 49). We believe that IFP also trigger MC toxicity and activation in vivo thus triggering acute sustained inflammation during continuous IFP infusion, which could be significantly decreased by MC deficiency or depletion. At physiologic concentrations, both insulin formulations fibrils (not shown) are toxic to human mast cells and also cause mast cell degrandulation in vitro.

Example 13—Insulin, Fibrils and Preservative Induce Tissue Injury and Inflammation Using general flow diagrams 59-64 we have shown that 1) insulin, fibrils and preservatives (IFP) induced tissue injury and inflammation when infused in vivo, 2) IFP induced toxicity and immune-dysfunction (e.g. cytokine expression) in exposed leukocytes and tissue cells in vitro, and 3) using our new open loop system in diabetic mice glucose control requires an increased insulin infusion with CSII post infusion time, and 4) leukocytes take-up insulin and degrade it using serine proteases e.g. elastase and 5) blockage of insulin degradation using anti-proteases. All these issues decrease the local and systemic levels of insulin. The increased requirement of insulin infusion with time on CSII is also seen in patients with diabetes. These data show that IFP trigger SQ tissue reactions that compromise infused insulin regulation of blood glucose (BG).

The data shown demonstrated that 1) IFP trigger inflammation at SQ infusion sites, and 2) leukocytes (PMN and MQ) take up and degrade insulin in vitro.

Example 14—Observed Tissue and Cellular Effects after Exposure to IFP Components FIG. 36 shows the outcome of in vivo and in vitro exposure testing using various cell types and various IFP factors. Concentrations represent the levels of various IFP factors at which effects can be observed. These data show the impact of IFP factors on tissue and cells.

Acute and long-term failure of CSII blood glucose (BG) regulation in T1D is the result of insulin/excipient (FE) induced tissue reactions (i.e. inflammation, loss of vasculature and fibrosis). Specifically, FE induced tissue reactions limit insulin access/transport to the vasculature (blood and lymphatic vessels) due to inflammation (acute phase) and fibrosis (chronic phase), as well as inflammation induced degradation of insulin at the infusion site (see FIG. 1). The solutions described below overcome CSII induced tissue reactions and thereby extend the lifespan and effectiveness of CSII. This result is demonstrated using our in vivo murine "air pouch/open loop" model). A brief summary of the specific approaches and methodology are detailed below.

PROPHETIC EXAMPLES

Prophetic Example 15—Murine "Air Pouch/Open Loop" Model of Blood Glucose Regulation Utilizing CGM and CSII Distribution of infused fluids, such as insulin or excipients, into the tissue occurs in highly variable patterns due to tissue structure and gravity. This variability makes tissue reaction evaluation often extremely difficult. In order to be able to consistently evaluate insulin/excipients/saline (I/E/S) induced tissue sites, a predictable infusion site for histologic analysis is required. The ability to retrieve viable cell population from that site in a simple fashion is an additional requirement for quantitative evaluation of tissue reactions and cell expression profiles. To achieve this goal we utilize a classic model to evaluate inflammation and agents that induce or suppress inflammation: known as the "air pouch model". Additionally, for these studies our focus is on using rapid acting analog (Humalog) insulin. Humalog is currently routinely used for CSII pump infusion reducing the rationale for testing longer acting insulin proteins and their formulation excipients. In addition, most insulin excipients are conserved across regular and rapid acting insulin analog preparations with minor exceptions in preservative type and concentration.

For these studies we utilized the general work flow diagram described in FIG. 60. We use the murine "AP/OL" model described in the preliminary data section of this application (see workflow diagram in FIG. 60). I/E/S infusion is done using Iperico wireless pumps (FIG. 3) as well as traditional patient insulin infusion pumps. FIG. 16 lists mouse models for evaluation. FIG. 17 lists working ranges of I/E/S and FIG. 18 lists tissue reactions for evaluation. We evaluate I/E/S induced tissue reactions daily during 3-days of infusion as well as the cumulative effects at the end of 3 days. Subsequent studies focus on tissue reactions for up to 7 to 14 days of infusion. Infusion sites are marked for location using tattoo ink. Insulin+excipient and excipient only induced tissue reactions and lavage samples are be evaluated systematically in control (non-diabetic) and diabetic mice using standard immunohistopathology and immunocytocemistry (ICC) (FIG. 18).

Qualitative or quantitative differences in tissue reactions between I/E/S components & concentrations as well as between animal models are determined. For example, due to wound healing defects associated with diabetes, I/E/S induced tissue reactions may substantially differ in the diabetic state. As such, spontaneous NOD (autoimmune) and streptozotocin (STZ) models of type 1-diabetes mouse models and the db/db mouse model of type 2-diabetes will also be considered. Tissue reactions and cell influx will be correlated with insulin regulation of BG levels and CGM in control and I/E/S treated and compared between diabetic and non-diabetic mice on the C57BL/6 background. These studies elucidate the baseline IFP induced tissue reactions and their relative component potencies.

It is expected that I/E/S induces significant and increased tissue reactions (histology and cell influx) over the first 3 days of infusion. Due to I/E/S induced tissue injury we anticipate a potential for sustained tissue reactions after infusion removal.

Prophetic Example 16—Evaluations of Cell and Gene Expression Obtained Through Lavage Following Insulin, Excipient or Saline Exposure Using the Murine "Air Pouch" Model The focus of this study is primarily on characterization lavage and blood associated cells and factors involved in the E/I induced tissue reactions. Specifically, the "air pouch" model allows lavage of leukocytes that have been recruited into the air pouch. The recruited leukocytes can be sorted into significant subpopulations using standard FACS sorting and analysis (FIG. 16). Using FACS analysis allows greater speed analysis of large and diverse numbers of samples and leukocyte subpopulations. For example, evaluation of the impact on various treatment protocols and therapies, as well as new infusion pump technology. As such, the analysis of lavaged cells represents an important tool dissecting the mechanisms as well as effectiveness of approaches to better control CSII induced tissue reactions. Additionally, one of the byproducts of lavage are unique microvesicles that can be used for both biomarkers, as well as for mechanistic insights into the E/I induced tissue injury. Microvesicles are small membrane extrusions (packets) that are released from activated and injured cells and bind to target cells (FIG. 17). Once bound to target cells microvesicles unload their "cargos" of RNA and proteins and as such take control of the target cells. Since these microvesicles are also released into the blood stream, they have been used as biomarkers for disease progression in cancer and vascular disease. The evaluation of cells and microvesicles obtained from the air pouch lavages is an extremely important tool in obtaining insights in order to control CSII induced tissue reactions.

Leukocytes and microvesicles derived from lavaged fluid are obtained from various animal population and treatment regiments (described above including Tables 3-5). Blood samples from these same animals are utilized for analysis of peripheral blood leukocyte gene expression, as well as isolated blood-derived microvesicles for RNA and protein analysis (FIG. 16). Lavage or blood derived cells are separated from the fluid phase by low speed centrifugation. The resulting cell populations are fixed and analyzed by FACS analysis and sorted for leukocyte subpopulations (https://www.bdbiosciences.com/documents/cd marker handbook.pdj). The sorted cells are then extracted for RNA and processed (cDNA libraries) for NexGen RNA Sequencing and analysed by SBI (https://www.systembio.com/services/exo-miseq/overview). The microvesicles are isolated for lavage fluid or blood plasma using Exoquick (SBI) and processed for NexGen RNA sequencing and analysis (https://www.systembio.com/services/exo-miseq/overview), as well as MS/MS analysis by SBI (https://www.systembio.com/services/exosomes/mass-spec). Unique biomarkers for E/I induced tissue reactions are processed using qPCR/RNA arrays as well as ELISA assays to aid in the development of simple rapid assays to determine the impact of therapies and new devices on I/E/S induced tissue injury and CSII blood glucose regulation.

We expect that RNA analysis of the lavaged leukocytes subpopulation will demonstrate significant increases in pro-inflammatory proteins versus anti-inflammatory proteins. The specific nature of these RNA/proteins and their levels could provide useful and important prognostic tools for evaluating the success or failure of E/I infusion in our animal models. I/E/S infusion in normal and diabetic mice will determine diabetes wound-healing defects on I/E/S induced tissue reactions and blood glucose regulation. Currently there is no literature on the existence of microvesicles in murine models or human models regarding insulin and excipient infusion. As such, it is important to determine whether the RNA/protein profiles seen in the microvesicles are associated with any of the leukocyte populations seen in the lavage, tissue or in the blood of the infused diabetic and non-diabetic animal populations. Results of these data provide important insights into potential mediators and mechanism related to I/E/S induced CSII failure. The discovery of E/I specific biomarkers or biomarker panels would provide useful tools for rapid evaluation of various therapeutics or new devices that may prevent I/E/S induced tissue injury and subsequent failure of blood glucose regulation in vivo.

Prophetic Example 17 Evaluation of Gene Expression in Tissue Derived from the Murine "Air Pouch" Model One of the cornerstones of the present studies is to characterize reactions that occur at I/E/S infusion site within the open loop murine air pouch model. Although we have developed significant preliminary data indicating that the insulin/excipients cause substantial tissue reactions including tissue injury and influx of inflammatory cells, these observations need to be confirmed and expanded. It is important to emphasize that these studies provide important insights into leukocyte gene expression in vivo. These studies also allow insights into the gene expression of tissue cells such as mast cells, dendritic cell, endothelial cells and fibroblasts all of which are critical in inflammation and wound healing. This data provide the foundation for developing useful assays (RNA arrays and ELISA) that aid in the evaluation of I/E/S induced injury markers, as well as lead to the effectiveness of therapeutic approaches to prevent I/E/S induced tissue reaction.

Initially tissue obtained from sites of I/E/S infusions in our "air pouch open loop model" will be removed enbloc, fixed and processed using standard technology FIG. 18. We will identify cells, proteins as well as RNA present at the infusion site. In addition to these traditional methods of "staining" tissue we will also utilize new cutting edge technologies including RNAScope for RNA presence and distribution of RNA probes for detection of all classes of RNA including mRNA, miRNA, siRNA (http://www.acdbio.com/products). These probes have the advantage detecting all forms of RNA present in cells including RNA for proteins that are unknown or not transcribed, as well as proteins that currently no antibodies exist. We will also use LaserCapture Microscopy coupled with Next-Gen RNA and MS/MS sequencing to determine all RNA and proteins present in injured and non-injured cells. These studies utilized LCM and RNA arrays to characterize gene expression in various inflammatory giant cell subpopulations. For the AP/OL studies we will isolate specific cell populations located at the I/E/S infusion sites including: macrophages, mast cells, lymphocytes, fibroblasts and endothelial cells. In vivo RNA expression in these various cell population over time and various conditions enables better understanding of the cells, mediators and mechanisms that affect CSII function. Comparing RNA and protein present in both injured and non-injured cell after various treatments (i.e. I/E/S or saline infusion) will allow us to determine unique signatures of RNA, proteins and pathways that are affected by I/E infusion into the murine air pouch.

These studies provide important insights into leukocyte gene expression including gene expression of tissue cells such as mast cells, dendritic cell, endothelial cells and fibroblasts. The combination of traditional histopathology, IHC and LCM coupled with RNAScope and NexGen RNA.

Prophetic Example 18—Impact of Post-CSII on Tissue Reactions in the "Air Pouch" Model Although the clinical dictum for CSII failure is "when in doubt, pull it out". Changing the infusion location (arm, belly or butt) may address blood glucose regulation in the short-term, it does not address the long term consequence of the induced tissue reaction at the original infusion site. Our belief predicts that even with the secession of insulin infusion and removal of the cannula at the infusion site, tissue reactions set in motion continue. Subsequent tissue repair leads to chronic inflammation characterized by increased recruitment of pro-inflammatory macrophages and lymphocytes ending with scarring (fibrosis) of the original infusion site, which compromises that site for future CSII infusion. Due to well-established defects in wound healing seen in diabetic populations the outcome is most likely more pronounced. To a large degree this deficiency in wound healing is believed to be a lack of transitioning macrophages from pro-inflammatory M1 macrophages into pro-wound healing M2 macrophages. This transition failure from M1 to M2 induces chronic inflammation, which causes prolonged tissue injury and ultimately results in more severe fibrosis associated with the disappearance of vasculatures networks (blood and lymphatic vessels) at the tissue site. The lack of vasculature networks delays tissue repair and as such leads to limiting the effectiveness of CSII at that site in the future. Understanding and preventing the prolonged tissue reactions seen at CSII sites is critical to maintaining viable tissue infusion sites.

For these studies we use the same general protocol, approaches and metrics as described above. As described above we will also initially tattoo the perimeters of the "air pouch" prior to infusion in an effort to assure identification of the infusion site used during the initial I/E/S infusion segment of the experiment. Post 3 day E/I/S infusion the cannula is removed and the tissue site is evaluated for tissue reactions for 7, 14 and 21 days post termination of infusion. Tissue reaction is evaluated utilizing standard histopathologic (H&E and trichrome), immunohistochemical analysis for cell populations and biomarkers including RNAScope analysis. In a second set of studies we will sustain the "air pouch" after cession of infusion and removal of the cannula. This is accomplished by infusion of sterile air into the "air pouch" once every third day. Lavage and "air pouch" tissue analysis can be done as described in FIG. 60. We expect that despite secession of FE infusion and cannula removal, tissue injury leads to chronic inflammation with significant fibrosis and associated loss of vasculature networks. There is nothing known about potential cells and mediators that drive these post CSII tissue reactions including how to overcome them. The studies outlined above will lead the way to therapies and new devices that will limit this insulin induced tissue destruction. Initial studies in our lab suggest that the evolution from acute inflammation, with PMN hallmark cells, will progress to a more chronic inflammation characterized by the presence of macrophages and lymphocytes. The exact nature and products of these PMN and macrophages and their influence on controlling tissue reaction at the insulin infusion site remains unknown. Considering that wound-healing defects are more pronounced as a result of diabetes, the insulin infusion induced tissue reactions are most likely more prolonged. Understanding the mechanisms and mediators that drive these tissue reactions will aid in the development of new therapeutic strategies and devices which will limit the chronic inflammation and fibrosis at sites of CSII infusion.

Prophetic Example 19—Impact of Extended Infusion and "Same Site" Insulin/Excipient Re-Infusions on Tissue Reactions and Blood Glucose Regulation We believe that sustained or repeated I/E/S infusion within the same tissue area (e.g. repeated infusion in the lower abdomen) induces chronic tissue injury, inflammation and fibrosis ultimately resulting in loss of viable tissue sites for CSII and CGM. This study examines the impact of extended and repeated "same site" I/E/S infusion on tissue reactions and CSII blood glucose regulation in normal and diabetic mice.

To investigate the impact of extended CSII infusion we will extend I/E/S infusion into normal and diabetic mice beyond the normal 3 days to 7 and 14 days and evaluate tissue reactions, blood glucose regulation and gene expression, In the case of same site infusion studies, we intermittently-infuse I/E/S at the same site using the "air pouch open loop" model. For these studies we use at least three complete cycles of continuous 3-day IFP infusion separated by catheter removal, and a 7-day rest period prior to reinitiate the I/E/S reinfusion in the same "air pouch". Tissue dye (i.e. tattoo a 4 corner box around the original infusion site) will ensure a consistent infusion location. Diabetic mice receive bolus insulin injections in the peritoneum during the 7-day rest period to control BG levels in also see FIG. 14. The ability of the infused insulin to maintain blood glucose regulation in our open loop murine model is also considered.

Based on the clinical observations of site fibrosis in T1D patients, we anticipate increased chronic inflammation and tissue scarring/fibrosis at repetitive infusion sites. The most potent fibrosis inducing I/E/S component or combination thereof could provide a key target for either insulin reformulation or mechanical removal prior to delivery. Systematic characterization of I/E/S induced tissue reactions are critical steps in determining the primary causative factors and mechanisms as well as determining concentrations & timing of tissue injury & site viability for studies described below.

Prophetic Example 20 Insulin Degradation In Vivo

We believe that I/E induced tissue reactions can induce loss of blood glucose regulation as a result of degradation of insulin by proteases at the infusion site. This belief is supported by our in vitro preliminary data, which demonstrates that leukocyte protease can degrade insulin in vitro. This degradation can be inhibited by the addition of clinically relevant anti-proteases (see FIG. 22 for list of antiprotease to be used). These studies provide the foundation for in vivo anti-protease studies and determine whether protease inhibitors can block the degradation of insulin in vivo and thereby extend CSII.

The occurrence and degree of insulin degradation is studied utilizing the "AP/OL" model followed by analyzing the lavage fluid. Using both traditional as well as fluorescent insulin (see preliminary data) coupled with traditional analysis (SDS peptide PAGE, western blot and/or gel filtration) we will determine the extent of protease-based degradation of insulin. We will consider 2 approaches 1) the addition of florescent insulin to the existing insulin formulation in infusion pumps and/or 2) the analysis of insulin fragmentation using standard Western blot technology using the same PAGE conditions as used for our in vitro studies (see preliminary data above). Standard gel filtration/ion exchange studies may also be undertaken to isolate individual insulin fragments of the degraded insulin. Intact & degraded florescent-insulin are detected in the PAGE gels using black light (see prelim data). Proteases present in the lavage fluids will also be characterized using BioRad protease PAGE gels (BioRad Zymogram gels) and protease inhibitors (FIG. 22).

Based on our preliminary data we expect that insulin present in the lavage fluids will be degraded. Proteases (particularly leukocyte derived proteases) will also be detected in the lavage (e.g. insulin degrading enzyme (IDE), elastase, trypsin). Once we have confirmed the degradation of insulin in the lavage fluids, we will determine the ability of specific protease inhibitors to block insulin degradation in vivo). If the studies find that specific protease inhibitors will block insulin degradation in vivo, and that this blockage of insulin degradation enhances CSII effectiveness in regulating blood glucose levels in diabetic mice, we will use this information as the foundation for future studies in swine and eventually humans.

Prophetic Example 21—In Vitro Evaluation of the Impact of Insulin and Components on the Activation/Gene Expression in Blood (Leukocytes) and Tissue Cells from Normal and Diabetic Mice It is important to develop in vitro screening tools that will mimic these in vivo results (see FIG. 23 for flow diagram). This will allow high throughput evaluation of various inhibitors and introducers of FE specific gene expression, which is critical in saving time and cost when compared to in vivo assays. We propose to utilize NexGen RNA sequencing and in vitro cell cultures to establish a screening panel for various inhibitor/enhancers of FE induced reactions. The most likely therapeutic agents and concentrations are then tested in our murine model.

For this screening tool we will utilize representative murine cell populations as indicator cells, i.e. leukocytes, adipose cells and fibroblasts. Cells are cultured in vitro with varying concentrations of I/E/S for 24 hrs (Table 4). Following RNA harvest, cDNA libraries are prepared and NexGen RNA sequencing undertaken (FIG. 21). Since only 100-1000 ng of RNA is required for deep sequencing, only 8,000-10,000 cells are required for each assay. NexGen RNA sequencing results are used to develop RNA arrays for subsequent selection of the most effective agents for in vivo studies. We will consider the use of standard ELISA assays to also screen agents for consideration in the in vivo "air pouch" model. We will also consider usage of this same approach to compare responsiveness of leukocytes from diabetic versus non-diabetic mice to see if there is any difference in the responsiveness of these 2 cell populations in vitro. It should be noted that all cell culture supernatants are collected and frozen at −80° C. for potential microvesicle analysis in the event that studies in Section 1 (above) suggest that microvesicles are useful biomarkers for FE induced tissue reactions. See FIG. 24 for the general approach for analysis of the exosomes.

We already established the utility of screening leukocyte populations exposed to FE in vitro as a useful tool for modeling FE tissue reactions, i.e. cytokine express studies in preliminary data section above. We believe that coupling NexGen RNA sequencing with high throughput RNA arrays will give us the most comprehensive view of FE induced cell activation since it will represent the entire expression profile in cells in response to specific inducers (FE) or agents (inducers or inhibitors). Comparison of these in vitro data with the in vivo data will validate the in vitro data and help understand the underlying pathophysiology involved in FE induced tissue reactions. With the establishment of this in vitro assay system we anticipate that we can undertake rapid analysis of the various inhibitor described above, which will allow rapid selection of candidate agents, which can prevent FE induced tissue reactions and extend CSII lifespan and function in vivo. It should be noted that if time and money is available we will undertake selected studies using leukocyte populations from normal and diabetic patients to establish a human FE profile panel, which is useful in future human CSII studies.

Our current preliminary data supports our belief that FE induced tissue reactions at infusion sites compromises CSII function and lifespan both in the short term (inflammation and loss of vasculature networks) and long term (fibrosis at the infusion site). We have selected a representative group of candidate inhibitors to deliver locally to site of FE infusion (see FIG. 221). This group was selected based on our current understanding of major inhibitors of inflammation, fibrosis and proteolysis as well as vascularization. We plan to use the same insulin infusion pumps and co-deliver inhibitors individually or in combination. We will determine the impact of co-delivery on the FE induced tissue reactions and CSII infusion effectiveness and lifespan. We will utilize 2 approaches for this delivery 1) add the inhibitors in the FE formulations in a traditional pump system or 2) use the dual pump delivery system from Ipercio dual pump. The choice of 2 approaches for inhibitor delivery is that 1) the potential of the inhibitors affecting the insulin while in the same pump container and 2) possible FDA concerns regarding changes to currently approved insulin formulation when combining inhibitors.

Prophetic Example 22—Impact of Infusion of Inhibitors/Inducers of Tissue Response on Tissue Reactions and CSII Blood Glucose Regulation Using the "AP/OL" Model in Normal and Diabetic Mice For the candidate inhibitors and inducers present in FIG. 22, we have selected the most likely candidates based on our current preliminary data. Nevertheless, as knowledge is gained from Goal 1, this list will be modified to select the most likely tissue modifiers that will successfully control FE induced tissue reactions in vivo.

We use representative general anti-inflammatory drugs (FIG. 22), followed by more targeted inhibitors on inducer as presented in FIG. 22. Each drug is injected into the air pouch twice daily to determine FE inhibitory impact. Once the optimal dose of drug is obtained from these injection studies, we will determine the stability of the individual drug in the FE solutions. For that selected inhibitors are incubated with I/E/S individually at 37 C for 3 days to mimic the typical on-patient exposure time and temperature. The resulting (individual or combination) of drug FE of saline treated samples will be infused into air pouch model for 3 days and tissue reactions evaluated If combining of the drugs with I or E results in loss of insulin functionality or drug function we will utilize the dual pump system It should be noted that in the case of the anti-protease studies we plan on incorporating protease inhibitors that show effective blockade of insulin degradation. Possible examples are: alpha 2 macroglobulin, IDE inhibitors (neutralizing antibodies) as well as protease inhibitors including aprotinin, alpha-1-antitrypsin (AAT), SP16, pepstatin, and or HALT alone or in combinations, into the various insulin formulations (including FITC-insulin, +/−preservatives) used for infusion in our diabetic mouse model (see Preliminary data section). We will also consider additional protease targets such as plasmin plasminogen activator and cathepsin D. It has recently been demonstrated that cyclodextrins are able to protect insulin from protease degradation in vitro. Since our studies have shown that leukocyte proteases can degrade insulin (see preliminary data sections), the usage of cyclodextrins would provide added protection to insulin degradation. Further determine whether local infusion of individual protease inhibitors (or combination of inhibitors) can block insulin (FITC-insulin+/−insulin) degradation, inhibit tissue reactions, and maintain BG regulation in our diabetic mouse models.

If any of these inhibitors or inducers demonstrate the ability to inhibit FE induced tissue reactions and enhancing CSII performance, we will extend the studies from 3 to 7 days of infusion and beyond depending on the results. Depending on the result we will also consider using drug combinations to maximize control of the tissue reactions at the infusion sites.

We anticipative that the general anti-inflammatory drug (Group 1 in FIG. 22) will block the FE induced tissue reactions and promote CSII in the mouse model. As such, these will represent positive controls for evaluation of other drugs. We anticipate that cytokine and chemokine inhibitors will also inhibit leukocyte recruitment and activation and as such enhance CSII performance directly as well as decrease the amount of protease present at the infusion sites. The ability of Borezomib to inhibit fibrosis will be particularly important in preventing long-term loss of infusion sites. Of particular interest will be if increasing vascular networks at the infusion sites will enhance CSII performance and lifespan. Based on our studies and others that demonstrate that VEGF induced vascular networks at glucose sensor implantation sites increases sensor performance in vivo, we anticipate that increased vascular networks will benefit CSII function.

Our preliminary data supports our belief that current insulin excipients (phenol/m-cresol) are tissue toxic. Although it is important in finding solutions to control excipient induced tissue reaction, it is equally important to consider alternatives. As such, it is our goal to consider solvents to replace existing excipient with solutions already FDA approved and which provide insulin stability. Cyclodextrins, a family of cyclic compounds made up of sugar molecules from starch by enzymatic conversion, have been demonstrated to provide insulin stability for extended period of time. Cyclodextrins are designated as GRAS by the FDA (i.e. Generally Regarded As Safe) and are utilized as a solvent in drug delivery and in a wide variety of food.

Cyclodextrins are composed of glucose monomers ranging from six to eight units in a ring, creating a cone shape. The original cyclodextrins contained 6-8 sugar rings: α (alpha)-cyclodextrin: 6-membered sugar ring molecule β (beta)-cyclodextrin: 7-membered sugar ring molecule γ (gamma)-cyclodextrin: 8-membered sugar ring molecule. Cyclodextrins have a "donut" shape with the polar hydrophobic hole and a hydropilic outer ring. Due to this configuration cyclodextrins can solubilize and stabilize both small and large molecules including proteins in aqueous solutions. In the case of large molecules, like proteins, cyclodextrin make "caps" over hydrophobic regions of the protein thus allowing the hydrophilic outer ring to be exposed to the water molecules which increases its solubility. Cyclodextrins have been shown to be more effective than current phenol based excipients in stabilizing insulin in vitro. It has also been demonstrated that long-term insulin (insulin-Glargine) solubilized by Cyclodextrins are functionally active in diabetic animals. Unfortunately, there is not data on the functionality of fast acting insulin utilized in CSII. As such, we propose to determine the effectiveness of 1) total replacement of current phenol based excipients and 2) significantly decrease current CSII excipients while replenishing them with the addition of Cyclodextrins.

Prophetic Example 23—Evaluation of Cyclodextrins as Excipients for Infusible Insulin The central goal of this investigation is to determine whether cyclodextrins can be used to replace traditional phenol based excipients. For that, we will focus our study on Dexolve (http://cyclolab.hu/index.php/dexolve), also referred to as Dexolve. Due to its high solvent efficacy and FDA approval (http://cyclolab.hu/index.php/dexolve), Dexolve is an ideal candidate for stabilizing insulin in aqueous solutions. As such, our goal for this section of the application is to demonstrate that cyclodextrins, such as Dexolve, when replaced with phenol can serve as an insulin stabilizer and that cyclodextrins do not cause tissue reaction. It has recently been demonstrated that cyclodextrins are able to protect insulin from protease degradation in vitro. Since our studies have shown that leukocyte proteases can degrade insulin (see preliminary data sections), the usage of cyclodextrins would provide added protection to insulin degradation.

We will first investigate whether Dexolve can function as replacement recipients for current CSII fast acting insulin (Humalog) preparations. In order to remove phenol, Humalog insulin is dialyzed according to protocols described by Kitagawa. Humalog insulin is then replaced with Dexolve at a concentration of 10-50% as recommended by CycloLab. Alternatively, insulin formulations are dialyzed against varying concentrations of Dexolve (10-50% solutions). Following dialyses, the kinetics of amyloid fibril formation of Humalog is investigated according to protocols of Kitagawa, i.e., fibrillation of Humalog is monitored as a function of time by measuring Thioflavin T fluorescence intensity and by the usage of transmission electron microscopy. Dexolve exchanged insulin will be compared for functionality and biocompatibility by injection into the diabetic air pouch mouse model. If the Dexolve exchange insulin shown functionality similar to the original insulin we will incubate both forms of insulin at 37 C for 1 month and determine the functionality and biocompatibility of these 2 insulin preparations again using the diabetic mice. If the dialysis exchange studies are successful we will under take studies to investigate the direct solubilization of insulin with Dexolve or other related cyclodextrins.

Based on the data already developed by CycloLab, as well as the literature related to cyclodextrins and long lasting insulin we believe that the Dexolve will successfully replace phenols in the insulin formulation, and that the new Dexolve based insulin will be more stable and more biocompatible when compared to current insulin formulations. If the Dexolve is not effective, CycloLab has a large number of other forms of cyclodextrins that will be investigated for both insulin stability and biocompatibility. If successful we will than investigate the ability of Dexolve to solubilize other factors with the insulin including the various factors described in Goal 2 above and incorporate them into the Dexolve insulin formulations.

We are investigating new pump devices that will enhance the effectiveness of both existing as well as new insulin formulation in the future. The 2 approaches we are considering are the usage of dual drug pumping devices (Iprecia Dual Pump; FIG. 27) and secondly the removal of phenol form insulin formulations immediately before infusion into the tissue, i.e. phenol removing resins/beads.

Prophetic Example 24—Effectivenesss of Iprecin Wireless Dual Insulin Pumps on CSII Function and Lifespan as Well as Blood Glucose Regulation Central to our belief is the concept of lowering phenol concentrations within insulin formulations currently available for CSII. The approach focuses on long-term removal of the phenol has part of the original formulation of the insulin. An alternative approach is to dilute insulin immediately prior to infusion thereby lowering the effective dose of phenol infused into the site during CSII. To achieve this we propose to use an Iperci dual pump to allow dilution of the standard insulin formulation with buffer or other solvents such as Dexolve just before it is infused into the tissue. Additionally using this dual pump approach it will be possible to combine various agents drugs described above with the insulin immediately prior to infusion thus limiting effect of insulin or factor on each other during normal shelve life of any new drug-insulin formulation (e.g. inhibitor-insulin formulation). This could also simplify issues with approval of new configuration of insulin for uses in CSII.

For these studies will begin by determining the impact of diluting the current formulation of insulin 1/10 using the dual pump in real time during CSII into the "AP/OL" mouse model and evaluate the blood glucose regulation and tissue reactions as described above. In this case full strength insulin will be pumped through channel 1 and buffer will be pumped at 10× higher speed through channel 2. The effective result will be a 10 fold dilution of the insulin and phenol immediately before infusion. The pump rates will be adjusted to account for the lower insulin concentration. As controls we will also pump combinations of insulin and standard excipants in channel 2 to account for any pump variations. The metric will be to see if diluting the excipiants will decrease tissue reactions and increase CSII function and lifespan in vivo. Additionally, we will determine if pumping insulin via one channel and various drugs and factors that control tissue reactions will be more effective than mixing the drugs/factors into the original insulin formulation.

Prophetic Example 25—in-Line Removal of Phenols During CSII

An alternative to utilizing dual pump technology to lower the concentration of phenols in the current formulations of insulin in real time, would be to have inline filters immediately in front of the infusion site to remove the phenol (see FIG. 27). Ion exchange resins have been shown in vitro to remove phenols from solution of insulin and we have also demonstrated that ion exchange resins can remove phenols form current insulin formulations. Additionally, Cyclodextrin also bind to phenol in vitro and as such are a candidate for ion exchange resins to remove phenols in insulin formulations. Although there is currently no published data on Cyclodextrin binding to phenols, personnel communication with our consultants at Cyclolab highlights that phenol is bound by cyclodextrin polymer (cyclodextrin immobilized into a network by crosslinking with epichlorohydrin) strongly most probably with higher affinity than to the aromatic amino acids of the protein. The moieties in the para position strengthen the interaction with the cyclodextrin but those at the ortho or meta (especially meta) position weaken it. For preliminary experiments we recommend to use our beta-cyclodextrin bead polymer"."

For these studies wel utilize a simple in-line filter that is placed immediately before the infusion needle on a standard CSII infusion set and at various amounts of cation resin or beta-cyclodextrin bead polymer will be added and standard insulin formulation will be pumped thru a established flow rates. We will first monitor the rate and capacity of phenol and insulin removal be these beads in vitro and once optimized in vitro we will begin in vivo studies using our air pouch/open loop model in mice. We will use the same metric for evaluating CSII effectiveness and blood regulation as described in Goal 1.

We believe that these inline filters are effective in removing phenol immediately prior to infusion into tissue in our mouse model. If it is successful this may be a simple and effective approach since it will not require the reformulation of the current FDA insulin promulgations. Prophetic Example 28—Impact of IFP on SQ tissue reactions in normal & diabetic mice Tissue reactions induced by individual IFP components (i.e. insulin, fibrils & preservatives,), alone and in combination, are evaluated systematically in control (non-diabetic) and diabetic mice using standard histopathology and immunohistochemistry (IHC) (FIG. 323). The focus is on Humalog insulin since only rapid acting analog insulin is currently routinely used for CSII pump infusion. Most insulin excipients are conserved across regular and rapid acting insulin analog preparations with minor exceptions in preservative type and concentration. Because of wound healing defects associated with diabetes, IFP induced tissue reactions may substantially differ in the diabetic state, so spontaneous NOD (autoimmune) and streptozotocin (STZ) models of type 1-diabetes mouse models and the ob/ob mouse model of type 2-diabetes are examined. These studies show the baseline IFP induced tissue reactions and their relative component potencies.

FIG. 30 lists mouse models for evaluation. FIG. 31 lists working ranges of IFP components, and FIG. 32 lists tissue reactions for evaluation. We evaluate IFP induced tissue reactions daily during 3-days of infusion, and days 4, 5, 6 and 7 post infusion. Extended duration infusion of 7-d will also be examined. Infusion sites will be marked for location using tattoo ink. Qualitative or quantitative differences in tissue reactions between IFP components & concentrations and between animal models will be determined. Tissue reactions are correlated with insulin regulation of BG levels and CGM in control and IFP treated mice.

Based on our preliminary data, we expect that all IFP will induce significant and increased tissue reactions over the first 1-3 days of infusion with a potential for sustained tissue reactions after infusion removal. Insoluble fibril may have the most sustained effects, while preservatives are expected to be immediately tissue toxic. Insulin alone may have cellular activation potential.

Prophetic Example 29—Impact of "Same Site" IFP Re-Infusions on Tissue Reactions

We believe that sustained or repeated IFP infusion induces repeated tissue injury, inflammation and fibrosis, ultimately resulting in loss of viable tissue sites for CSII and CGM. This study examines the impact of repeated "same site" IFP infusion in normal and diabetic mice.

At least three complete cycles of continuous 3-day IFP infusion separated by catheter removal and a 7-day rest period simulate catheter site rotation. Tissue dye (i.e. tattooing a 4 corner box) ensures a consistent infusion location. Pathology and IHC tissue reactions (FIG. 35) provides quantitative endpoints for IFP components as above. In diabetic mice both cumulative tissue reactions and the ability to maintain blood glucose regulation in our open loop murine model are considered.

Based on the clinical observations of site fibrosis in diabetic patients, we expect increased chronic inflammation and tissue scarring/fibrosis at repetitive infusion sites along with additional adverse effects in diabetic animals due to impaired wound healing.

Prophetic Example 30—Impact of Inflammation on Insulin Regulation of Blood Glucose Levels in Diabetic Mice To evaluate the impact of inflammation of insulin regulation of BG in diabetic mice, inflammation is induced prior to or during insulin infusion (FIG. 33) using direct injection of inflammatory agents (LPS (endotoxin) [12], leukocyte chemotactic factors: $f$-MLP or KC (rodent version of IL-8) or leukocytes (insulin uptake and degradation) at insulin infusion sites. Agents will be injected or added to insulin formulations used for SCII. Saline infusions will serve as control for insulin infusions. Fluorescent insulin (Sigma) will be used in selected experiments to track the distribution and uptake of insulin by tissue and inflammatory cells at the infusion sites. Tissue reactions and BG regulations (FIG. 35) will be determined in diabetic mice with inflamed infusion sites. Treatment protocols include:
1. Inject/infuse insulin subcutaneous in pre-existing diabetic mice with LPS/$f$-MLP induced inflammation present
2. Co-infusion of insulin subcutaneous plus LPS/$f$-MLP in diabetic mouse
3. Local injection of LPS (0.1-10 ug)/$f$-MLP ($10^{\wedge}$-5M)/KC (0.5 ug) at infusion sites during ongoing SCII
4. Local injection of $10^5$-$10^6$ leukocytes (PMN, macrophages or lymphocytes)+/−IFP or LPS/$f$-MLP pretreatment at infusion sites BG levels and CGM and tissue reactions will be monitored and correlated with the above treatments.

We expect that LPS/$f$-MLP induced inflammation or direct injection of leukocytes compromises insulin therapy in diabetic mice, as reflected by decreased responsiveness of BG to insulin infusion/injection. We expect that the decrease in BG responsiveness to insulin will correlate with the increased inflammation and number of leukocytes injected at infusion site.

Prophetic Example 31—Impact of Corticosteroid Therapy on Insulin Control of Blood Glucose in Diabetic Mice Given that IFP induces inflammation and that inflammation decreases BG insulin regulation, it is believed inflammation is responsible for these regulatory effects. As such, we will correlate IFP and LPS/f-MLP induced tissue reactions with insulin control of blood glucose in diabetic mice with and without systemic or local (corticosteroid added to insulin formulation) corticosteroid (hydrocortisone [15]/dexamethasone) treatment for 3-7 days of SCII. The impact of corticosteroid on IFP and LPS/f-MLP induced tissue reactions is determined by standard histopathology and BG using our murine model of CGM and insulin infusion (see preliminary data section).

It is expected that anti-inflammatory treatment suppresses IFP and LPS/f-MLP induced tissue reactions and enhances insulin BG regulation.

Prophetic Example 32—Demonstrate Insulin/Fibril Binding and Uptake by Leukocytes (PMN, MQ and Lymphocyte Cells) In Vitro and In Vivo Using Fluorescent Insulin We utilize FITC-insulin (Sigma) alone or "spiked" into Humalog insulin. Insulin fibril will be obtained by standard protocol using the FITC-insulin or the spiked insulin. For in vitro studies mouse peritoneal PMN or MQ, and spleen lymphocytes as well as human peripheral blood leukocytes+/−LPS or $f$-MLP are used. Individual leukocyte populations are isolated and cultured in vitro. Once the cultures are established FITC insulin or FITC fibrils are added and florescence uptake by cells is followed microscopically for up to 3 days. Cell viability is determined with trypan blue and presence of intact nuclei by DAPI staining. For in vivo studies FITC-insulin or fibrils will be injected or infused SQ in diabetic mice over a 3-day period. At days 1, 2, and 3 mice are sacrificed and the resulting fixed tissue is processed for standard histopathology. Fluorescence distribution is determined by microscopy. Additional in vivo studies include secession of SCII and removal of the cannula and evaluation of FITC-insulin and fibril at the infusion site for up to 1 week. Standard immunohistochemistry (IHC) for leukocyte populations is used for the analysis as needed.

Based on our preliminary data shown in FIG. 12 above, we expect that FITC-insulin and fibrils will be taken up by leukocytes in vitro and in vivo. We also anticipate that normal and injured tissue cells at the injection/infusion sites are likely taken up the FITC-insulin and fibrils. We anticipate fluorescence insulin is seen in the plasma & leukocytes.

Prophetic Example 33—Demonstrate Cell-Based Degradation of Insulin and Fibril In Vitro and In Vivo To characterize the ability of leukocyte derived protease (total leukocytes, PMN, MQ, Lymphocytes or mast cells) to degrade FITC-insulin or fibrils in vitro or in vivo. For in vitro studies we analyze in vitro leukocyte culture supernatants and leukocyte lysates or IFP injected tissue extracts (non-glutaraldhyde fixed) obtained from Prophetic Example 24 above. Standard 10-20% SDS PAGE gels (Bio-Rad) are utilized to show insulin degradation. Standard anti-proteases (see FIG. 14 above), and anti-protease cocktails (e. g. HALT) are added to the extract to characterize proteolysis in leukocyte and tissue extract involved in the degradation of the FITC insulin. Intact & degraded insulin or fibrils are detected in the PAGE gels using black light (see prelim data). We also measure the levels of human insulin, IDE and elastase in the IFP infusion sites tissue extracts using commercial ELISA. Proteases are characterized using BioRad protease PAGE gels (BioRad Zymogram gels) and protease inhibitors (FIG. 14).

Based on our data we anticipate that total leukocyte extracts (FIG. 14 and FIG. 13 above), as well as their related proteases (e.g. insulin degrading enzyme (IDE), elastase, trypsin), will degrade FITC-Insulin and that this degradation can be blocked with various protease inhibitors (see preliminary data). Once we have confirmed the degradation of the FITC-insulin, we will determine the ability of specific protease inhibitors to block FITC-insulin degradation (FIG. 14) in vitro.

Prophetic Example 34—Role of Resident Skin Leukocytes, Such as Mast Cells (MC) and their Products to IFP Induced Tissue Reactions Mast cells (MC) are key skin "sentinel" cells and are generally the first tissue cell population activated by tissue trauma. Recent results from our laboratory indicate that skin mast cells affect glucose sensor induced tissue reactions and CGM function. FIG. 35 demonstrates insulin is MC toxic and activates MC in vitro. We expect that in vivo IFP trigger MC toxicity and activation and as such trigger inflammation during continuous IFP infusion. We expect that IFP induced tissue reactions are decreased in mouse model of MC deficiency or depletion.

For these MC studies we utilize 2 established murine models of MC deficiency and depletion. Bone marrow of MC (i.e. MC reconstitution) are used to confirm the MC involvement in the IFP induced tissue reactions. A third model of MC involvement in IFP reactions is to directly inject isolated MC into the IFP infusion sites. We also evaluate chemical based mast cell inactivation as possible future therapeutic interventions. To deplete MC of the granules we utilize Compound 48/80 (1.2 mg/kg body wt./24 hr) prior to implantation using the procedure by Kolaczkowska et al. We compare streptozotocin as well as NOD and ob/ob diabetic mice as described above. Tissue MC numbers and distribution are determined histologically, and histamine (granule marker) levels are monitored by ELISA/RIA using tissue homogenates obtained from the sites of IFP infusion/injection. Blood glucose and leukocyte levels also are monitored. The impact of granule depletion on the tissue reactions and CSII is determined as described above. The impact of 48/80 on all tissue, blood factors and cells is done as described in the Cromolyn studies above.

These models were recently used in our laboratories to evaluate MC induced reactions to CGM glucose sensors. We expect that mast cell deficiency and depletions dramatically suppress IFP induced tissue reactions. Conversely, we expect that MC injections at IFP delivery sites will increase tissue reactions & decrease glucose control in diabetic mouse models.

Prophetic Example 35A—Contributions of Circulating Leukocytes, Such as Polymorphonuclear Leukocytes (PMN), to IFP Induced Tissue Reactions MC and dendritic cell (DC) activation can trigger inflammation by releasing leukocyte chemotactic factors. Generally, PMN (neutrophils, granulocytes) are the "first wave" of peripheral inflammatory blood leukocytes recruited to tissue injury sites. Our preliminary data has clearly demonstrated IFP induced PMN recruitment to insulin infusion sites. Nevertheless, the contribution of these PMN to IFP induced tissue injury and MQ recruitment is not known. We believe that PMN depletion will decrease tissue damage and MQ recruitment in IFP induced reactions.

Systemic depletion of mouse PMN/granulocytes using anti-GR-1 antibodies is routinely used to evaluate the role of PMN/granulocytes in tissue reactions. Here, we will pre-deplete and maintain depletion of circulating PMN/granulocytes in normal and diabetic mice prior to IFP infusion for up to 7 day exposure. Non-immune IgG injections will be used as negative procedural controls. A 3-day and 7-day infusion timeline will be used for these studies. Tissue samples at 1, 2, 3, 4, 5 and 7-day time points post IFP infusion from both normal and diabetic mice will be evaluated using our histopathology panel. In the case of the diabetic mice, we will also evaluate the impact of the PMN depletion on CSII control of blood glucose levels. A second approach is to determine the impact of direct injections of PMN at insulin infusion sites & determine the impact of PMN injections on tissue reactions & BG levels in diabetic mice.

We expect that systemic PMN depletion will decrease tissue injury/inflammation by limiting the availability of tissue toxic PMN as well as their products, i.e. MQ chemotactic factors (MCF) at insulin infusion sites and thereby decreasing MQ recruitment to these sites. Alternatively, peripheral macrophages alone may be key contributors to IFP reactions and MQ deficient and depletion studies will be examined as described below. We also anticipate that the direct injection of PMN at insulin infusion sites will decrease insulin BG regulation in diabetic mice.

Prophetic Example 35B—Contributions of Circulating Monocyte/Macrophages to IFP Induced Tissue Reactions To address MQ impact on IFP local tissue reactions, we will utilize a classic "addition/deletion" approach, enhance or deplete M/MQ populations. Specifically we will utilize:
1) Direct Injection of Monocyte/Macrophages at Sites of IFP Injection or Infusion Our previous data demonstrated that direct MQ injection at CGM sensor sites induces rapid loss of CGM sensor function. Based on our in vitro data, which showed IFP toxicity, we believe that IFP induce MQ activation and thereby amplify IFP induced inflammatory reactions by releasing MQ mediators. We also believe that MQ decreases CSII effectiveness by insulin uptake & degradation by MQ derived proteases (see also below).

We will utilize our published approach by first isolating thioglycolate induced peritoneal MQ from C57BL/6. These cells will then directly injected at the IFP infusion site in normal and diabetic mice ($10^5$-$10^7$ MQ per site). CSII and CGM sensor function, blood glucose levels and histology at the implantation site will be determined up to 7 days post MQ injection. Injection of equivalent numbers of strain matched spleen-derived lymphocytes are used as a negative cellular control. If discernible effects are observed, we may utilize direct injection of MQ using strain-matched cells in other pre-diabetic and diabetic mouse models including ob/ob mice.

Thioglycolate induced MQ are generally referred to as M1 and are inflammation promoters. Alternatively, M2/angiogenesis-repair MQ could have a positive impact on CSII. We believe the direct injection of thioglycolate derived pro-inflammatory M1 (both normal and diabetic derived) will negatively affect CSII function and trigger increased inflammation at the insulin infusion sites. This model should simulate MQ recruitment to CSII sites.
2) Transgenic Macrophage Depletion (CD11b-Diptheria Toxin (DT) Receptor (DTR) Mice)

Similar to the above studies on local DT DC depletion, this study will examine the effects of depletion of peripheral M/MQ using a DTR/DT transgenic depletion mouse model. This model has been used successfully to demonstrate the importance of recruited MQ in CGM sensor induced tissue reactions.

Similar to the transgenic DC model in 2.2.2 above, mice over-expressing the diphtheria toxin (DT) receptor on CD11b positive monocytes/macrophages (Jackson Lab, stock number 005515) provide a method to deplete peripheral MQ selectively by low dose IV DT injection (10 ng DT/g body weight). DT will be injected in a priming dose 1-week before testing, and weekly thereafter to maintain M/MQ depletion. Cellular and histological markers including blood leukocyte levels, including PMN, lymphocytes and monocytes, as well as blood glucose levels will be monitored. DT injection into non-transgenic animals and development of chimeric animals after M/MQ replenishment from normal mouse bone marrow donors will be used as negative and positive controls respectively.

We anticipate that DT mediated M/MQ depletion will result in decreased IFP induced tissue reactions in both normal and diabetic mice, similar to the depletion models described above, while M/MQ replenished chimeric mice should display similar outcomes as normal controls.

3) Genetically Macrophage Deficient Mice (Op/Op Mice)

As an alternative to M/MQ addition or depletion models, op/op mice, are genetically M/MQ deficient due to a gene mutation that eliminates colony-stimulating factor-1 (CSF-1) production resulting in severe monocytopenia and diminished granulomatious responses. We have used this model to successfully demonstrate the role of MQ in CGM in vivo response studies.

The op/op mice are commercially available (Jackson Lab). IFP induced tissue reactions in the op/op and control mice will be evaluated from 0-7 days post IFP infusion. CSII and CGM sensor function, blood glucose levels and histology will be evaluated in this model. If decreased inflammation or decreased CSII function is observed in the op/op strain, M/MQ reconstitution from matched control bone marrow donors will be examined. STZ-induced diabetic version of this strain may also be examined. Blood monocyte levels will be correlated to the degree of tissue reactions and CSII function.

We anticipate that op/op (MQ deficient) mice will have decreased IFP induced tissue reactions and increased CSII lifespan. However, these differences will be abolished after M/MQ reconstitution. This would support the role of MQ in IFP induced tissue reactions, and also suggest that CSF-1 dependent MQ may be specifically involved. Lack of difference in IFP induced tissue reactions and CSII function would suggest that CSF-1 independent MQ may be central to tissue reactions. If this is the case clodronate/etoposide depletion (Aim 4) of monocyte/macrophages in op/op and control mice would likely decrease IFP induced tissue reactions and increase CSII function in both mouse strains. Finally, op/op mice with STZ induced diabetes may have decreased tissue reactions and enhanced sensor function due to defective wound healing including decreased collagen production.

Prophetic Example 36—Cell Specific Gene Expression In Vivo—Laser Capture Microsurgery (LCM)

To better correlate the above in vivo results and in vitro results from our experiments, we use LCM to dissect individual cell populations at the IFP infusion tissue-device cannula interface and characterize cytokine expression and tissue reaction pathways using qRT-PCR and standard RT-PCR arrays (FIG. 21).

These studies will isolate specific cell populations located at the device implantation site including: giant cells, macrophages, mast cells, lymphocytes, fibroblast and endothelial cells. In vivo RNA expression in these various cell population over time and various conditions enables better understanding of the cells, mediators and mechanisms that affect CSII function.

Prophetic Example 37—High Throughput In Vitro Cellular Toxicity, Cell and Cytokine Expression Screening Assays While there are numerous commercially available PCR, cytokine and cytotoxicity assay kits available, assays must be identified and/or customized that are appropriate for the cell lines of interest, capable of performing within the anticipated dynamic range of cellular expression or viability, and that are compatible with a high throughput format.

Screening assays will be developed utilizing real time polymerase chain reaction (RT-PCR) as a high throughput-screening assay followed by multi-marker ELISA assays in order to confirm important expression patterns revealed in the RT-PCR screening panels, with both negative and positive controls for mediator expression. Cytotoxicity assays will also be validated with relevant cell types such that marker expression can be correlated with the viable cell population. These studies will utilize human immortalized or primary inflammatory and tissue cells to maximize the data's translational reliability.

Assay development will result in reproducible, accurate, high throughput screening methodologies for use in Prophetic Examples 38-39.

Prophetic Example 38—Screen and Quantify In Vitro Impact of IFP Components on Gene and Cytokine Expression Across the Range of Expected Concentrations Found During Normal CSII Use, Using Primary Leukocytes, Tissue Cells and Related Cell Lines The contribution of individual IFP components to pro-injury and pro-inflammatory mediator(s) expression is unexplored. IFP component effect on gene and cell marker expression will be investigated using leukocyte and tissue cell populations described in FIG. 38. These studies will establish endpoints and baselines for gene and cytokine expression including the chief mediators and pathways of local cell injury and inflammation (FIG. 38). Preliminary data indicate that a wide concentration range of IFP can induce expression of pro-inflammatory cytokines in human PBMC including IL-1B, IL-6 and IL-8 in vitro. Additionally, LCM technology plus RT-PCR has been used to characterize gene expression in multinucleated giant cells generated in vitro. These studies demonstrate important insights into causes of inflammation, loss of viable tissue, and the failure of CSII and CGM in vivo.

IFP components, single and in combination, will be incubated in select non-diabetic and diabetic (if available) cell populations at concentration ranges expected during normal CSII and over 3-5 days to simulate normal and extended duration wear. PCR and cytokine assays (ELISA) developed in Prophetic Example 29 will be used to evaluate cytokine and receptor gene marker up-regulation of cellular inflammation pathways at relevant time points to assess possible inflammation mechanisms. Specific cells of interest include various leukocytes and representative subcutaneous tissue cells, from immortalized lines or primary human blood isolates: THP-1 Monocyte/Macrophage, HMC-1 mast cells, PMN, PBMC, adipose cells, and fibroblasts. Baseline data can be established in non-diabetic cell populations followed by comparison in diabetic cells.

In vitro endpoints will be examined in order to determine the mediators and pathways that drive IFP-induced tissue injury, inflammation, and fibrosis, as well as to compare the effects in non-diabetic vs. diabetic cell populations. These data will be compared to in vivo data previously collected, as well as aid in designing or refining additional in vitro and in vivo studies. In future studies it will be important to quantify the in vitro impact of IFP components on various cell function (e.g. chemotaxis, phagocytosis, proliferation) across the range of expected concentrations found during normal CSII use, using primary leukocytes, tissue cells & related cell lines.

The focus of Prophetic Examples 39-43 is to demonstrate the mediators, mechanisms and cells involved in IFP induced tissue reactions and interference with CSII, and identify targets that can overcome the negative impact of IFP on CSII. Approaches to deliver various inhibitors at the insulin infusion site must also be developed. We believe the insulin infusion pump/formulations may already enable this, by co-mixing various anti-inflammatory and anti-protease drugs and factors) with the existing insulin formulations or through use of dual pump/lumen infusion cannulas. The below drug examples provide initial translation of the above "proof of concept" studies into practical solutions. For these studies we utilize our open loop mouse model (see FIGS. 8A-8D).

Prophetic Example 39—Impact of Local Delivery of Dexamethasone/Prednisone on IFP Induced Tissue Reactions and CSII Function Previously we have demonstrated that dexamethasone or prednisone can dramatically suppress tissue reactions induced by CGM sensors as well as significantly increase sensor function in our mouse model. Based on the results of the systemic dexamethasone studies in Aim 1, we will next determine whether local dexamethasone/prednisone infusions or injections, in combination with insulin formulations or other IFP agents, can suppress IFP induced tissue reaction as well as CSII function in diabetic mice.

We determine the impact of systemic dexamethasone on CSII considering the published mouse protocol and the results from Aim 1 in order to establish dexamethasone levels. We will evaluate the impact of dexamethasone on various IFP at all concentrations that induce significant tissue reactions or interfere with CSII in our initial studies from above. If systemic dexamethasone treatment significantly decreases IFP induced tissue reactions and increases/maintains CSII in our diabetic mouse model, we will subsequently incorporate various concentrations of dexamethasone into the insulin solutions for injection and/o infuse in the mouse models. The impact of the local infusion/injection of the insulin, preservatives or fibrils+/−dexamethasone or prednisone combinations will be included to evaluate tissue reactions and blood glucose levels in diabetic mice.

Based on our previous studies we anticipate that local dexamethasone/prednisone will suppress IFP induced tissue reactions and enhance CSII in our diabetic mouse models. The salient issue is whether co-infusion of dexamethasone will be able to suppress IFP induced tissue reactions. If we are able to demonstrate that an insulin injection or pump infusion can locally co-deliver dexamethasone at effective levels for short periods of time (1-3 and up to 7 days), it will be an ideal system to test other anti-inflammatory, anti-fibrotic or other tissue engineering drugs and agents directly at the infusion site such as investigations described below.

Prophetic Example 40—Impact of Local Drug Depletions of Mast Cells (MC)/MC Products on IFP Induced Tissue Reactions and CSII Function Many of the agents used to test the role of mast cell function in these studies have been used to therapeutically control mast cell effects in allergic diseases. For example, existing drugs, such as oral Cromolyn (Gastrocrom) or Ketotifen (Apo-ketotifen, Zaditen) commonly used to treat patients with allergic disorders, could be used in the near future to extend CSII. These same agents, likely in a topical form, could also control mast cell function at CSII sites.

Previous studies have reported that blocking mast cell degranulation and the associated release of pro-inflammatory factors with granule stabilizing agents prevents mast cell induced inflammation and disease. Current data from our lab supports a role for mast cell degranulation in the loss of CGM sensor function: blocking MC degranulation with the stabilizing agents Cromolyn or Doxantrozole extends sensor lifespan in vivo, and MC granule contents can directly inhibit sensor function in vivo. Thus, we propose to evaluate MC granule stabilization on IFP induced tissue reactions in wild type and diabetic mice as well as CSII in diabetic mice.

A classic approach to determine the role of mast cell in tissue reactions and disease is to use Cromolyn or Doxantrozole to stabilize MC membranes and block MC degranulation. We utilize co-infusion or co-injection of Cromolyn (100-400 mg/kg body wt.) or Doxantrozole (20-100 mg/kg body wt) with insulin at sites of CSII infusion in C57BL/6 control and streptozotocin (diabetic) C57BL/6 mice as previously described. Upon completion of the studies, we will evaluate these treatments on both NOD and ob/ob mice, and their corresponding controls. Since diabetes in the NOD and ob/ob mice is progressive, (i.e. they progress from non-diabetic to pre-diabetic and finally full diabetic states), we will evaluate the impact of drug treatment at each diabetic stage to provide data regarding the role of disease progression on CSII function. Tissue MC numbers will be determined histologically, and blood leukocyte counts and differentials will be performed in order to confirm the absence of these drugs' side effects. No drug side effects are anticipated as these drugs have been extensively used in mast cell research, but we must consider any potential impact of diabetes on the various cells of interest.

Based on our sensor data, we expect that Cromolyn or Doxantrozole based stabilization of mast cell will decrease IFP induced tissue site reactions and will significantly enhance CSII in diabetic mice. It will be particularly interesting to assess for any significant differences between diabetic mouse strains as well as any subtle differences in tissue responses and as a function of disease progression.

Prophetic Example 41—Impact of Local Drug Blockade of PMN Accumulation & Edema on IFP Induced Tissue Reactions and CSII Function Aspirin is a safe and effective non-steroidal anti-inflammatory agent that blocks acute inflammation including PMN recruitment and edema. As such, we will consider its effectiveness in controlling IFP induced tissue reactions regulation in our open loop mouse model.

For these aspirin studies we will use the same general approach described above for local delivery of dexamethasone/Prednisone.

Due to the effectiveness of aspirin as an anti-inflammatory agent it will suppress IFP induced tissue reactions as well as promote more effective and long lasting blood glucose regulation in diabetic mice.

Prophetic Example 42—Impact of Local Macrophage Depletion (Etoposide and Clodronate Liposome Depletion) on IFP Induced Tissue Reactions and CSII Function Chemical/pharmacologic depletion of monocytes/MQ in mice has been employed to determine the role of macrophages in a variety of diseases and tissue reactions. We propose to independently use two different pharmacologic agents, clodronate liposomes and etoposide to deplete mice of circulating monocytes (i.e. systemic depletion). Comparing two agents minimizes possible artifacts due to drug side effects. We will initially use these agents to deplete normal and diabetic mice (streptozotocin treated (type I), NOD (type I) and db/db (type II) diabetic mice). For the initial studies C57BL/6 are selected since they are a common control for a number of the proposed mouse deficiency models. NON-mice will be used as controls for the db/db mice. Other mice backgrounds will be utilized for the various deficient and transgenic mice described in Aim 3.

CSII is evaluated in MQ depleted and non-MQ depleted mice. Initially, we will deplete non-diabetic as well as diabetic mice (streptozotocin treated, NOD and db/db mice) etoposide. Mice will be depleted of monocytes/MQ (M/MQ) using i.v. injections of clodronate liposomes (200 ul) that are available commercially from http://www.clodronateliposomes.org/. Liposomes lacking clodronate will be injected as a control. Blood leukocyte levels, including PMN, lymphocytes and monocytes, as well as blood glucose levels will be monitored in all mice. We will also monitor continuous sensor function in all mice using our recently described CGS Model. At selected time points mice (1, 2, 3 and 7) will be sacrificed for histological evaluation of tissue reactions at sites of sensor implantation.

In the case of the two control mice strains (C57BL/6 and NON), we expect that systemic depletion of M/MQs will decrease inflammation and fibrosis at the site of CSII. If we see that M/MQ depletion enhances CSII of one of the control strain mice to a different degree, this may suggest that there are some strain variations. Since all our mutant and knockout animals share the same background as the matched control/normal mouse, any strain variation can be automatically incorporated into the evaluations. Additionally, we anticipate that depletion of M/MQ in the diabetic mice (NOD and db/db) will markedly decrease inflammation as well as increase CSII, since it is known that diabetic mice have impaired wound healing, similar to what is observed in diabetic patients. It will also be interesting to determine the effect of MQ depletion on CSII in the spontaneous diabetic mice as they progress from the normal to pre-diabetic to diabetic states. Demonstrating that systemic depletion of M/MQ decreases tissue reactions and enhances CSII will provide key support for their role in the tissue reactions & loss of CSII.

Prophetic Example 43 Impact of Local Drug Blockade of Fibrosis on IFP Induced Tissue Reactions and CSII Function Bortezomib is a known inhibitor of fibrosis by blocking TGFb signaling pathways in both mouse skin and lungs. As such, we will determine whether Bortezomib will suppress fibrosis at IFP infusion sites in our mouse models of open loop blood glucose regulation. Controlling fibrosis is important in preventing IFP loss of healthy tissue. As CSII is extended beyond 7 days, preventing fibrosis will become even more important.

For these Bortezomib studies we will use the same general approach described above for local delivery of dexamethasone/Prednisone.

We expect that Bortezomib will be an effective inhibitor of IFP induced tissue reactions and will significantly extend CSII in our open model of blood glucose regulation. This should provide the proof of concept for CSII exceeding 7 days or longer.

Prophetic Example 44—Impact of Local Drug Induced Blood/Lymphatic Vessel on IFP Induced Tissue Reactions and CSII We have previously demonstrated that increasing blood and lymphatic vessel density at glucose sensor implantation increases sensor performance and lifespan. Based on these findings we believe that increasing both blood and lymphatic vessels at sites of SCII will increase the effectiveness and lifespan (>7 days) of this device.

For these studies we use the angiogenic factor VEGFa and lymphogenic factors VEGFc and VEGFd to induce blood and or lymphatic vessels at sites of SCII. With that we will determine the impact of vessel formation on tissue reactions and blood glucose regulation in our open loop mouse model of blood regulation.

Based on our experience on inducing blood and lymphatic vessels at glucose sensor implantation sites we anticipate that this family of angiogenic and lymphatic agents will enhance blood regulation at sites of CSII. The increased vessel network at CSII sites will more effectively transport insulin into the systemic circulation as well as decrease inflammation at the insulin infusion sites.

Prophetic Example 45—Local Suppression of Inflammation, Insulin Degradation and Enhanced Blood Glucose Regulation by Introducing Anti-Protease Drugs and Agents in Insulin Formulations In Vivo Our previously generated data support the concept that leukocyte derived proteases can degrade insulin in vitro and in vivo. In vivo this would lower the effective insulin levels at the infusion site and thereby impede BG regulation. Therefore, we expect that utilizing addition of protease inhibitors to insulin formulations would decrease insulin degradation and thereby prevent variation in the quantities of insulin required to achieve effective BG regulation. Since these anti-proteases are known to have anti-inflammatory effects we believe that they will also decrease inflammation at sites of insulin infusion of injection.

Initially we incorporate protease inhibitor that show effective blockade of insulin degradation. Examples include IDE inhibitors (neutralizing antibodies) as well as protease inhibitors including aprotinin, alpha-1-antitrypsin (AAT), SP16, pepstatin, and or HALT alone or in combinations, into the various insulin formulations (including FITC-insulin, +/−preservatives) used for infusion in our diabetic mouse model. We will believe that additional protease targets such as plasmin plasminogen activator and cathepsin D will be effective. Determine whether local infusion these individual protease inhibitors (or combination of inhibitors) can block insulin (FITC-insulin+/−insulin) degradation, inhibit tissue reactions, and maintain BG regulation in our diabetic mouse models (see Preliminary Data, FIGS. 7A and 8 as well as FIG. 7B).

We anticipate that incorporating protease inhibitors into insulin formulations will prevent insulin degradation, which will result in sustained insulin functional levels at infusion sites and assure effective regulation of BG levels in the murine mouse model. It is likely that there will be a need for multiple inhibitors to have a significant impact on insulin levels at the infusion sites and BG regulation. We also feel that although systemic uses of protease inhibitor will likely parallel the impact of local co-infusion with insulin formulations that in the long run incorporating the inhibitors into the insulin formulation will be the most function on cost effective approach to preventing insulin degradation and enhancing BG regulation in vivo.

Prophetic Example 46—Swine Model Qualification: Evaluate and Qualify the Relative Response of Normal and Diabetic Swine Models for IFP Infusion Site Inflammation Effects Compared to Mice Although swine are more physiologically similar to humans, their inflammatory response may be different from that predicted from murine models. These studies are designed to differentiate the similarities or differences between murine and porcine models.

Both non-diabetic (Yorkshire) and diabetic (alloxan induced Yucatan mini-pigs; Sinclair) with appropriate physiological SC dimensions based on historical studies, are exposed to IFP components at concentrations and time points identified to cause inflammatory cellular responses in mouse models from Aim 1. Excised tissue samples are examined by IHC and histopathology in order to compare the cellular response, for activated cell types of interest, time course, and response severity and local tissue toxicity. Method development or IFP exposure without active insulin protein may utilize primarily non-diabetic animals, although the salient responses will be confirmed in diabetic swine. Acute IFP effect will be evaluated over 5 consecutive wear days, while repetitive same site exposure will use 3 cycles of the 3 day on, 7 day rest, in order to simulate both extended acute wear and chronic repetitive site exposure. Pathology assessment will be as above but will also include assessment of fibrin capsule formation at the delivery site. Prior to biopsy, tissue sites are evaluated in vivo at 3d intervals, using high-resolution ultrasound and photo-acoustic microvascular imaging in order to examine the local tissue density and capillary network density in order to determine if repetitive inflammatory challenge causes physiological changes that could affect local insulin uptake. Infusion sites will be followed longitudinally after device removal and will also evaluate healing/scarring processes.

The porcine cellular response is expected to be similar in nature, scope and causation to murine models. However, the increased SC tissue density and increased dermal vascularity may result in some differences, especially for peripherally recruited PMN or M/MQ, or local tissue toxicity on the more organized SC adipose cells.

Prophetic Example 47—Correlate IFP Inflammatory Effects to Insulin PK/PD Variability in Diabetic Swine The above examples should yield sufficient knowledge to produce a controlled inflammatory response in the swine model, which will be utilized to examine the inflammatory effects on insulin uptake and BG control. Similar parallel studies can be performed in the mouse model but are limited by delivery volume, insulin concentration, sample numbers and volume, and repetitive studies in a given individual.

IFP component, concentration, and timing from Aim 5.1 will be dosed in order to establish a "standardized" inflammatory potential that will be confirmed by pathological examination acute inflammatory effects on insulin PK will be evaluated as follows: insulin PK absorption from standardized single bolus injections (3 IU) will be evaluated longitudinally over 5 consecutive days in naïve and intentionally pre-inflamed tissue sites. Concomitant blood glucose will be obtained via lab analyzer and/or a contralaterally implanted CGM sensor. PK outcomes will be compared for speed of uptake ($t_{max}$, $t_{50\% \, max \, rising \, and \, falling}$) and relative bioavailability ($C_{max}$, Insulin AUC) as a function of time and degree of inflammation. Effects on BG response will also be examined based on the delta BG, and calculated insulin sensitivity/insulin responsiveness. Sites exposed to repetitive inflammation injury with subsequent wound healing and scarring will also be examined for changes in PK/PD outcomes using methods similar to those previously described. Delivery at scarred sites will be measured using X-ray fluoroscopy studies of a radio-opaque dye in order to quantify deposition area, patterning, and tissue diffusion rate.

There is no consensus in the literature to predict the expected study outcomes. We believe that acute inflammation will reduce insulin availability and glucose regulation as a function of inflammatory severity, possibly due to local insulin degradation from inflammatory cells. Sites of repetitive injury showing increased collagen density, and reduced tissue diffusion should exhibit decreased insulin absorption and increased dose variability. Historically swine provide an excellent predictive PK response model.

Prophetic Example 48—Determine if Systemic or Local Administration of Anti-Inflammatory Compounds Mitigate the Inflammatory Response and PK Variability in Diabetic Swine Models Using methods developed in lower order mouse models, diabetic swine are exposed systemically or locally to anti-inflammatory agents developed in our murine models above. Reduced local tissue site reactions from IFP infusion will be confirmed histopathologically. Comparative PK/PD studies using the methods developed as described above are used to evaluate the effect of inflammation reduction on PK/PD outcomes and variability. Ideally, local or systemic intervention to minimize inflammation will result in PK/PD responses equivalent to naïve tissue sites. Later device prototypes with integrated anti-inflammatory agents are examined for direct effect on inflammation reduction via pathology and ultrasonagraphy and effects on PK/PD uptake (from Invest. 2b).

Based on the anticipated responses from above, it is expected that the swine model should exhibit similar effects although dose scaling or optimization may be required. Once optimized, these results should be a reliable predictor of human responses in translational clinical studies based on previous device testing experience in swine.

Prophetic Example 49—Impact of Anti-Inflammatory, Anti-Fibrosis & Anti-Protease Strategies on Porcine Models of CSII Protocols for the porcine studies will be developed based on the porcine models in described above. We anticipate that that the anti-inflammatory and anti-protease studies developed will translate into the porcine models.

Solutions to Problems Resulting from the Use of Insulin Formulations

The Examples provided above tissue infection and injury resulting from insulin injection and continuously infused insulin can cause inflammation, which leads to the loss of viable tissue for continuous subcutaneous insulin infusion and fibrosis.

Artificial pancreas system requirements include the need to maintain precise and accurate in vivo delivery of very minute and continuously variable amounts of insulin in response to changing blood glucose. Additionally, the physical absorption and BG response to infused insulin should remain constant, permitting stable AP algorithm performance. Based upon our recent work, we understand that insulin infusion triggers tissue injury and local inflammatory responses at insulin infusion sites, which ultimately results in limited infusion site longevity, premature infusion failure and PK absorption variability. We also understand the IFP trigger tissue injury and local inflammatory reactions (inflammation and fibrosis) both during infusion and afterwards (i.e. after cannula withdrawal), that ultimately limit infusion site longevity, infusion failure and PK absorption.

Problem 1. Insulin, insulin additives and their products are cell and tissue toxic, as well as immunomodulatory, and induce inflammation and scarring at sites of insulin injection and infusion.

Solution for Problem 1. Employ "In-line" device for the removal of insulin preservatives from insulin formulations immediately prior to injection or infusion. Using commercial preparations of insulin, we have made an in vitro device that demonstrates that insulin preservatives can be removed "in-line" from insulin formulations without reduction of insulin levels. These data demonstrate that a (small void volume) device can be placed in-line in an infusion set (or may be fabricated as an element of an infusion set) to remove toxic preservatives just prior to the insulin formulation entering the patient. Using this system will extend tissue Integrity at sites of insulin injections and infusion.

Problem 2. Insulin, insulin additives and their products are cell and tissue toxic, as well as immunomodulatory, and thereby decrease local host defenses at sites of insulin injections and infusion and thereby increases site infections. This increase in site infections lead to increased inflammation, and scarring which compromises short and long term insulin therapy for diabetes.

Solution for Problem 2. Employ collar-like barriers with added-microbial agents in order to alleviate CSII associated infection(s). We have developed a (tacky) silicone-based collar that contains an added antimicrobial agent and we have demonstrated that this device attribute extends the functional lifespan of commercial glucose sensors in vivo[1]. We believe these same silicone collars can be used with current insulin infusion sets to extend tissue Integrity at sites of insulin injections and infusion.

Problem 3. Movement of infusion set cannula causes tissue injury to both insertion site (cannula entry site) as well as underlying tissue. This movement 1) damages skin epithelial layers, thereby increasing risk of infection, and 2) induces dermal and subcutaneous tissue injury, inflammation and scarring which compromises short and long term insulin therapy for diabetes. Additionally, extended CSII infusion can cause compression on tissue beneath the infusion set, thereby inducing tissue injury, inflammation, and scarring which compromises short and long-term insulin therapy for diabetes.

Solution A for Problem 3. Employ non-drug/agent supplemented silicone collars as device "shock absorbers" to minimize tissue damage and "barriers" to infections associated with cannula movement that would compromise both short term and long term CSII tissue site integrity and to minimize the migration of bacteria into the open wound at the implantation site. Studies in our lab on the use of collar-like tacky silicone barriers with transcutaneous glucose sensors supports the concept that barrier-like collars without the addition of an antimicrobial agent can enhance transcutaneous device biocompatibility. We believe this technology can be very effective in enhancing CSII technology, particularly in efforts to extend the effective usage beyond 3 days.

Problem 4. Because CSII requires insertion of the insulin cannula across the skin into the subcutaneous tissue layer, the insertion site remains an open wound for the period of infusion that exposes the underlying tissue to the risk of infiltrating pathogens and subsequent infection and the associated inflammation, scarring and loss of tissue integrity.

Solution A for Problem 4. Employ collar-like barriers with added-antimicrobial agents in order to alleviate CSII-associated infection(s) and resulting inflammation that can compromise both short-term and long-term CSII tissue site integrity. We have developed a (tacky) silicone-based collar, that contain(s) antimicrobial or other clinically accepted agents, which extend the functional lifespan of commercial glucose sensors in vivo. We believe these same silicone collars can be used with current insulin infusion sets to decrease infusion site infections, inflammation and tissue scarring at sites of device implantation.

Solution B for Problem 4. Employ collar-like barriers modified to include epithelial growth factor (EGF) in order to promote wound closure by re-epithelialization of the cannula insertion site. We are currently developing epithelial cell growth factor (ECGF) collar-like barriers for implantable glucose sensors as part of our SBIR grant from the NIH. We believe these ECGF-containing collars will be extremely useful in extending CSII functional life spans in vivo.

Solution C for Problem 4. Employ collar-like barriers modified to include epithelial growth factor (EGF) and an antimicrobial agent. The development of growth factor based silicone collars we believe we can quickly integrate this growth factor technology into our existing anti-microbial collar technology.

Problem 5. Extended CSII causes increased adhesive damage to skin epithelium, thereby increasing the risk of infections, inflammation and scarring, all of which compromises short and long term insulin therapy for diabetes.

Solution for Problem 5. Employ "extended" collar-like barriers containing epithelial cell growth factors to promote wound closure at cannula insertion site and prevent infection associated inflammation that would compromise both short term and long term CSII Tissue site integrity.

Problem 6. CSII Cannula's induced tissue reactions and associated infections.

Solution A for Problem 6A. Employ a local drug delivery coated cannula to help minimize infections and inflammation and promote new blood vessel formation at sites of CSII. We have developed data that both CSII cannulas and Insulin formulations can induce inflammation at implantation sites. As such developing local anti-inflammatory and anti-fibrosis as wells as angiogenesis therapy would likely significantly extend tissue viability and thereby CSII. As part of our SBIR Grant we are currently developing drug delivery "sleeves" for implantable glucose sensors, and believe that these drug delivery "sleeves" can easily be translated into CSII cannula format.

Solution B for Problem 6B. Develop pump based drug delivery (single or dual lumen cannulas) to decrease infection, inflammation and fibrosis and induce new blood vessels at CSII infusion sites. An alternative of "coating" based drug delivery is to utilize the insulin pump system as part of an integrated insulin+drug delivery system. This could be done using a single or dual lumen system that could deliver insulin and drugs such as an anti-inflammatory and anti-fibrotic agent like dexamethasone and angiogenesis factors such as VEGF. We have developed a murine model of continuous glucose monitoring (CGM) with CSII (open loop) that we plan to utilize for these and other related studies.

Problem 7. CSII Induced Tissue Reactions and Infection Risk Continue after Insulin Infusion and Removal of the CSII Cannula Solution for Problem 7. We believe that it is critical to preserve infusion site tissue integrity by controlling inflammation and infection both during and after insulin infusion. We use post-infusion topical agents and delivery systems that control post-infusion tissue reactions and infections.

Methods to make cannulas and cannulas chronic insertion wounds more biocompatible and or prevent cannula infections/biofilms using liquid coating such as silicone, SLIPS and or Liquiglide with and without local drug delivery systems. Since poor cannula biocompatibility causes inflammation which insulin and its preservative can even further enhance, thereby decreasing CSII effectiveness, increasing cannula biocompatibility using liquid coating such as silicone, SLIPS and or Liquiglide with and without local drug delivery systems. Additionally, incorporating anti-microbial agents into the liquid coating such as silicone, SLIPS and or Liquiglide will also prevent cannula related biofilms, infections and inflammation.

Removal of preservative and/or fibrils, from CSII systems; using drugs, factor and other agent to improve cannula compatibility.

Embodiments that Incorporate Collars at the Point of Insertion into the Skin

FIG. 55A shows a Diagram of pump and infusion set with indicating sites where preservatives are removed by insertion of a removal or filtration system (designated as A with a white box in the diagram). Non-limiting examples of removal systems are ion exchange resins or cyclodextrin beads/polymers. Examples of filtration by size are porous membrane with specific sizing pores (e.g. membranes that retain complexes >50,000 kD).

FIG. 55B shows a Diagram of pump and infusion set with indicating sites were fibrils are removed by insertion of a removal or filtration system (designated as B with a white box in the diagram). Non-limiting examples of the removal systems are ion exchange resins or cyclodextrin beads/polymers. Examples of filtration by size are porous membrane with specific sizing pours (e.g. membranes that retain complexes >50,000 kD.

FIG. 55C shows Sites for addition of drugs, factors and or agents (e.g cyclodextrins) before or during CSII (designated C in white box) including addition of drug delivery systems. For example, adding drugs, factors and or agents to insulin formulations before or after introducing the insulin into the pump; introducing drugs, factors and or agents as the insulin leaves the pump or inline release in the tubing; release of drugs, factors and or agents in the infusion housing or "cap" releasing drugs, factors and or agents from the cannula or cannulas in the tissue.

FIG. 55D shows Dual lumen cannulas for separate delivery channels for insulin and other drugs, factors and or agents simultaneously at CSII infusion sites. This configuration prevents negative interactions between the insulin and drugs, factors and or agents use to control tissue reactions such as inflammation, fibrosis neovascularizations during storage of the insulin or drugs, factors and or agents prior to infusion. This system can utilize a single pump or 2 separate pumps.

FIG. 55E depicts Methods to make cannulas more biocompatible and or prevent cannula infections/biofilms using hydro-gels such as Basement membrane (BM) cross-linked or combinations of cross-linked and non-cross-linked BM with and without local drug delivery systems. Since poor cannula biocompatibility causes inflammation which insulin and its preservative can even further enhance, thereby decreasing CSII effectiveness, increasing cannula biocompatibility using bio-hydrogels such as basement membrane coatings with or without drugs incorporated into the hydrogels will decrease inflammation. Additionally, incorporating anti-microbial agents into the hydrogels will also prevent cannula related biofilms, infections and inflammation.

FIG. 55F shows Methods to make cannula chronic insertion wounds more biocompatible and or prevent infections using collars of hydrogels such as Basement membrane (BM) cross-linked or combinations of cross-linked and non-cross-linked BM with and without local drug delivery systems. Since chronic wounds result from extended cannula insertion, which in turn causes inflammation which insulin and its preservative can even further enhance, thereby decreasing CSII effectiveness, increasing wound healing and biocompatibility using biohydrol gels such as basement membrane coatings with or without drugs incorporated into the hydrogels will decrease inflammation. Additionally, incorporating anti-microbial agents into the hydrogels will also prevent cannula related biofilms, infections and inflammation.

FIG. 55G Methods to make cannulas and collars more biocompatible and or prevent infections by combining the cannula coatings and cannula collars described in FIGS. 64E and 64F above will significantly prevent inflammation and infections when used in conjunction with each other as well as with as without drugs factors and or agents.

FIG. 55H shows methods to make cannulas more biocompatible and or prevent cannula infections/biofilms using liquid coating such as silicone, SLIPS and or Liquiglide with and without local drug delivery systems. Since poor cannula biocompatibility causes inflammation which insulin and its preservative can even further enhance, thereby decreasing CSII effectiveness, increasing cannula biocompatibility using liquid coating such as silicone, SLIPS and or Liquiglide with and without local drug delivery systems. Additionally, incorporating anti-microbial agents into the liquid coating such as silicone, SLIPS and or Liquiglide will also prevent cannula related biofilms, infections and inflammation.

FIG. 55I shows Methods to make cannulas chronic insertion wounds more biocompatible and or prevent cannula infections/biofilms using liquid coating such as silicone, SLIPS and or Liquiglide coating collars with and without local drug delivery systems. Since poor cannula biocompatibility causes inflammation which insulin and its preservative can even further enhance, thereby decreasing CSII effectiveness, increasing cannula biocompatibility using liquid coating such as silicone, SLIPS and or Liquiglide with and without local drug delivery systems. Additionally, incorporating anti-microbial agents into the liquid coating such as silicone, SLIPS and or Liquiglide will also prevent cannula related biofilms, infections and inflammation. Use of filters and/or absorbing materials at other locations in the csii system to remove preservatives and/or fibrils Control—FIG. 56A shows a conventional insulin delivery system. FIGS. 56B-56F schematically show filtration cannula and/or cannula prefilter systems to remove preservatives and/or insulin fibrils from insulin. In FIG. 56 A the overall CSII system is generally designated as 50. The system 50 includes an insulin pump 51, which pumps insulin through an insulin delivery line 52. The insulin then enters an infusion housing 53 positioned between the delivery line 52 and a cannula 54. The cannula 54 is in direct contact with subcutaneous tissue in the body of a patient.

Figure 56B:
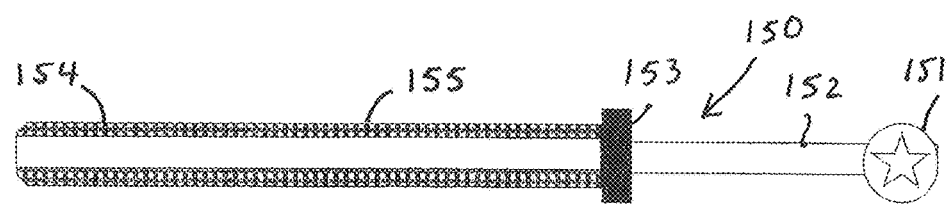

Coated Cannula—FIG. 56B shows an insulin delivery system in which the cannula is coated with, or made from, materials that can remove preservatives and/or fibrils from insulin formulations. In FIG. 56B the overall CSII system is generally designated as 150. The system 150 includes an insulin pump 151, which pumps insulin through an insulin delivery line 152. The insulin then enters an infusion housing 153 positioned between the delivery line 152 and a cannula 154. In the coated embodiment, the cannula is coated with a coating layer 155 of a filtration or absorbing material. In other cases, the cannula walls themselves are made from a filtration or absorbing material, which is a filtration system that removes preservatives and/or fibrils from the insulin before the insulin enters the patient's body. The use of the filtration system or absorbing material prevents or reduces tissue inflammation, infection and loss of effective insulin delivery using a CSII system.

Figure 56C:
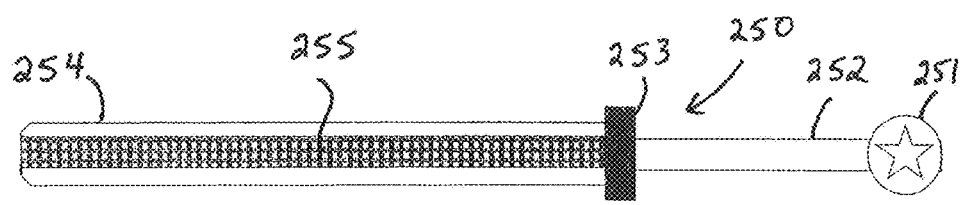

Filled Cannula—FIG. 56C shows an insulin delivery system in which the cannula is filled with a material that can remove preservatives and/or fibrils from insulin formulations. In FIG. 56C the overall CSII system is generally designated as 250. The system 250 includes an insulin pump 251, which pumps insulin through an insulin delivery line 252. The insulin then enters an infusion housing 253 positioned between the delivery line 252 and a cannula 254. The cannula 254 is filled with a material 255, which absorbs preservative and/or fibrils from the insulin before the insulin enters the patient's body. The use of the absorbing material prevents or reduces tissue inflammation, infection and loss of effective insulin delivery using a CSII system.

Figure 56D:
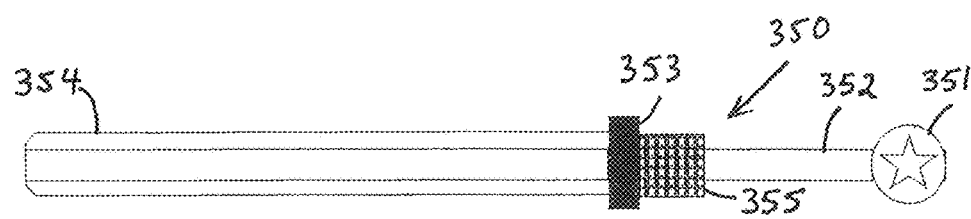

Modified Cannula Housing—FIG. 56D shows a system in which the cannula housing is filled with a material that can remove preservatives and/or fibrils from insulin, or is made from a material that can remove preservatives and/or fibrils from insulin. In FIG. 56D the overall CSII system is generally designated as 350. The system 350 includes an insulin pump 351, which pumps insulin through an insulin delivery line 352. The insulin then enters an infusion housing 353 positioned between the delivery line 352 and a cannula 354. The infusion housing 353 contains a filtration or absorbing material 355, or is made from a filtration or absorbing material, which removes preservatives and/or fibrils from the insulin.

Figure 56E:
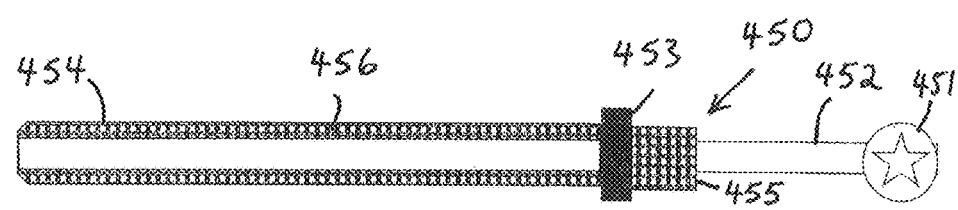

Coated Cannula and Modified Cannula Housing—FIG. 56E shows a system which is a combination of the systems of FIGS. 56B and 56D. In FIG. 56E the overall CSII system is generally designated as 450. The system 450 includes an insulin pump 451, which pumps insulin through an insulin delivery line 452. The insulin then enters an infusion housing 453 positioned between the delivery line 452 and a cannula 454. In this embodiment, the infusion housing 453 contains a filtration or absorbing component 455, which removes one or both of preservatives and fibrils. The walls of the cannula 454 are made of a filtration or absorbing material, which removes at least one of preservatives in fibrils. In some cases, component 455 removes preservatives and the cannula 454 wall material removes fibrils. In other cases, the component 455 removes fibrils and the cannula wall removes preservatives. Further embodiments, component 455 removes both preservatives and fibrils, while the cannula wall 454 removes either one of both of preservatives and fibrils. In other embodiments, the cannula wall removes both preservatives and fibrils while component 455 removes either preservatives or fibrils.

Figure 56F:
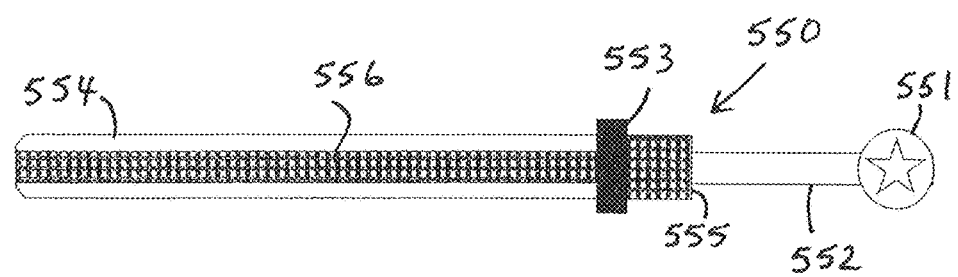

Filled Cannula and Modified Cannula Housing—FIG. 56F shows a system that is a combination of the systems of FIGS. 56C and 56D. In FIG. 56F the overall CSII system is generally designated as 550. The system 550 includes an insulin pump 551, which pumps insulin through an insulin delivery line 552. The insulin then enters an infusion housing 553 positioned between the delivery line 552 and a cannula 554. In this embodiment, the infusion housing 553 contains a filtration or absorbing component 555, which removes one or both of preservatives and fibrils. The cannula 554 is filled with a filtration or absorbing material 556, which absorbs preservative and/or fibrils from the insulin before the insulin enters the patient's body. In some cases, component 555 removes preservatives and the material 556 inside the cannula 554 removes fibrils. In other cases, the component 555 removes fibrils and material 556 removes preservatives. In further embodiments, component 555 removes both preservatives and fibrils, while material 556 removes either one of both of preservatives and fibrils. In other embodiments, material 556 removes both preservatives and fibrils while component 555 removes either preservatives or fibrils.

Use of Drugs, Factors and/or Other Agents to Improve Biocompatibility of Cannulas in CSII Control—FIG. 57 A shows a conventional insulin delivery system. FIGS. 57B-57F schematically show systems which incorporate drugs, factors and/or other agents to improve biocompatibility of cannulas. In FIG. 57 A the overall CSII system is generally designated as 70. The system 70 includes an insulin pump 71, which pumps insulin through an insulin delivery line 72. The insulin then enters an infusion housing 73 positioned between the delivery line 72 and a cannula 74. The cannula 74 is in direct contact with the body of a patient.

Figure 57B:
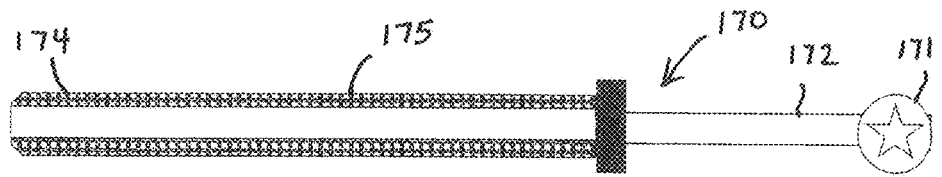

Coated Cannula—FIG. 57B shows an insulin delivery system in which the cannula is coated with materials that can deliver drugs, factors and/or other agents to improve insulin/preservative/cannula biocompatibility. In FIG. 57B the overall CSII system is generally designated as 170. The system 170 includes an insulin pump 171, which pumps insulin through an insulin delivery line 172. The insulin then enters an infusion housing 173 positioned between the delivery line 172 and a cannula 174. In the coated embodiment, the cannula 174 is coated with a coating layer 175, which can deliver drugs, factors or agents that reduce inflammation in the tissue that is in contact with, and surrounding, the cannula 174.

Figure 57C:
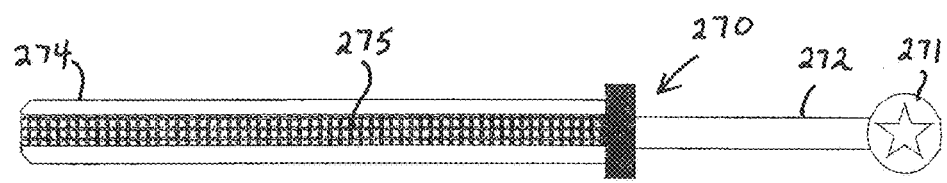

Filled Cannula—FIG. 57C shows an insulin delivery system in which the cannula is filled with a material that can deliver drugs, factors and/or other agents to improve insulin/preservative/cannula biocompatibility. In FIG. 57C the overall CSII system is generally designated as 270. The system 270 includes an insulin pump 271, which pumps insulin through an insulin delivery line 272. The insulin then enters an infusion housing 273 positioned between the delivery line 272 and a cannula 274. The cannula 274 is filled with a component 275, which delivers drugs, factors or agents that reduce inflammation in the tissue that is in contact with, and surrounding, the cannula 274. The use of the drugs, factors or agents prevents or reduces tissue inflammation, infection and loss of effective insulin delivery using a CSII system.

Figure 57D:
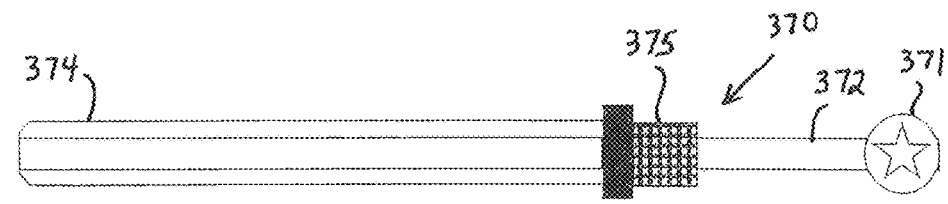

Modified Cannula Housing—FIG. 57D shows a system in which the cannula housing is filled with a material that can deliver drugs, factors and/or other agents to improve insulin/preservative/cannula biocompatibility. In FIG. 57D the overall CSII system is generally designated as 370. The system 370 includes an insulin pump 371, which pumps insulin through an insulin delivery line 372. The insulin then enters an infusion housing 373 positioned between the delivery line 372 and a cannula 374. The infusion housing 373 contains a material 375 that can deliver drugs, factors and/or other agents, or is made from a material that can deliver drugs, factors or other agents.

Figure 57E:
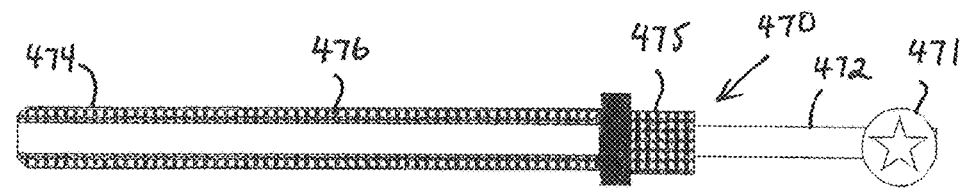

Coated Cannula and Modified Cannula Housing—FIG. 57E shows a system which is a combination of the systems of FIGS. 57B and 57D. In FIG. 57E the overall CSII system is generally designated as 470. The system 470 includes an insulin pump 471, which pumps insulin through an insulin delivery line 472. The insulin then enters an infusion housing 473 positioned between the delivery line 472 and a cannula 474. In this embodiment, the infusion housing 473 contains a component 475, which delivers drugs, factor or other agents that promote biocompatibility. The wall 476 of the cannula 474 has an outer coating 478 of this type of material. In some cases, component 475 delivers one type of substance and the coating 478 delivers another type of substance. In other cases, both component 475 and the coating 478 of the cannula 474 deliver the same substances.

Figure 57F:
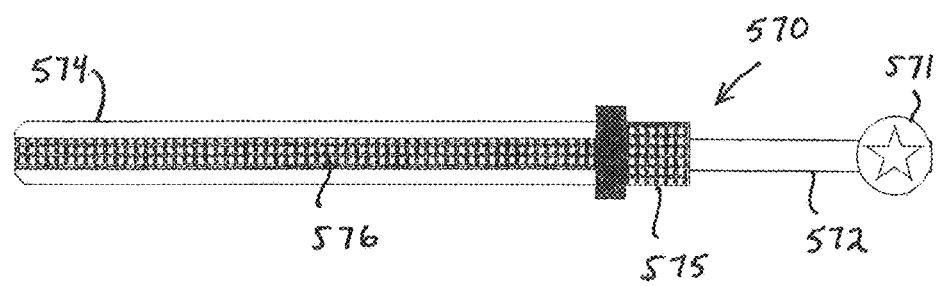

Filled Cannula and Modified Cannula Housing—FIG. 57F shows a system that is a combination of the systems of FIGS. 57C and 57D. In FIG. 57F the overall CSII system is generally designated as 570. The system 570 includes an insulin pump 571, which pumps insulin through an insulin delivery line 572. The insulin then enters an infusion housing 573 positioned between the delivery line 572 and a cannula 574. In this embodiment, the infusion housing 573 contains a component 575, which delivers drugs, factor or other agents that promote biocompatibility. The cannula 574 is filled with a material 576, which delivers drugs, factor or other agents that promote biocompatibility. In some cases, component 575 delivers one type of substance and the material 576 delivers another type of substance. In other cases, both component 575 and the material 576 deliver the same substances.

Removal of Fibrils and/or Preservatives from Insulin Delivered by a Syringe

Control—FIG. 58A shows a conventional syringe-type insulin delivery system. FIGS. 58B-58F schematically show syringe chamber and/or plunger sleeve systems to remove preservatives and/or insulin fibrils from insulin. In FIG. 58A the overall insulin delivery system is generally designated as 80. The system 80 includes a plunger cap 81, a plunger sleeve 82, a syringe housing 83, a syringe chamber 84 and a needle 86. The insulin enters the patient through the outer end of the needle 86. At least a portion of the needle 86 is in direct contact with subcutaneous tissue in the body of a patient during insulin delivery.

Figure 58B:
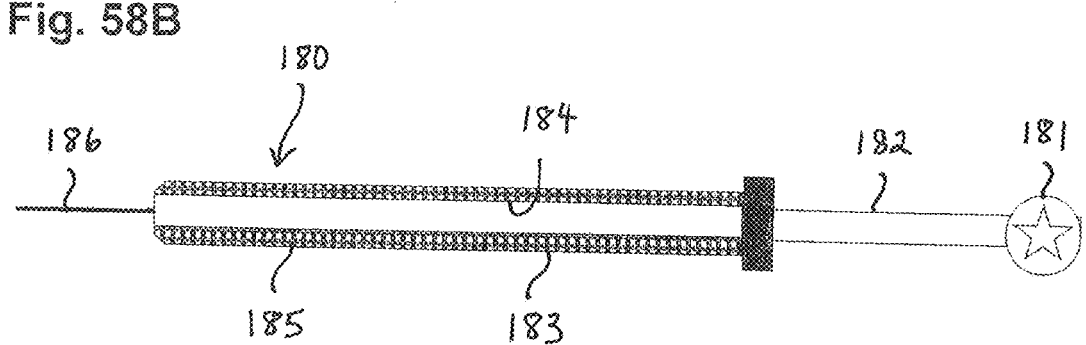

Coated Syringe Chamber—FIG. 58B shows an insulin delivery system in which the inner wall of the syringe housing is coated with, or made from, materials that can remove preservatives and/or fibrils from insulin formulations. In FIG. 58B the overall syringe-type insulin delivery system is generally designated as 180. The system 180 includes a plunger cap 181, a plunger sleeve 182, a syringe housing 183, a syringe chamber 184 and a needle 186. The insulin in the syringe chamber 184 enters the patient's body through the needle 186. In the coated embodiment, the inner wall 187 of the syringe housing, that is, the tubular wall defining the syringe chamber 184, is coated with a coating layer 185 which can remove preservatives and/or fibrils. In other cases, the syringe inner chamber wall 184 itself is made from a system that removes preservatives and/or fibrils from the insulin before the insulin enters the patient's body. The use of the filtration system or absorbing material prevents or reduces tissue inflammation, infection and loss of effective insulin delivery using a syringe-type insulin delivery system.

Figure 58C:
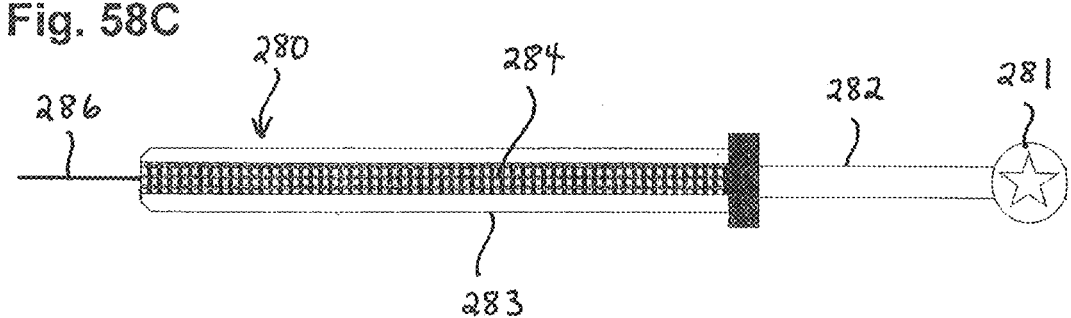

Filled Syringe Chamber—FIG. 58C shows an insulin delivery system in which the syringe chamber contains a porous material that can remove preservatives and/or fibrils from insulin formulations. In FIG. 58C the overall syringe-type insulin delivery system is generally designated as 280. The system 280 includes a plunger cap 281, a plunger sleeve 282, a syringe housing 283, a syringe chamber 284 and a needle 286. The insulin in the syringe chamber 284 enters the patient's body through the needle 286. The component 285 is formed from a porous material that removes preservatives and/or fibrils from the insulin and is contained within the syringe chamber 284.

Figure 58D:
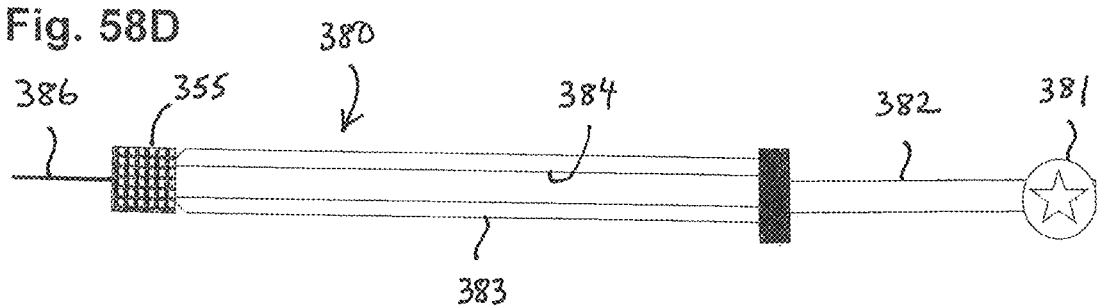

End-Modified Syringe Chamber—FIG. 58D shows an insulin delivery system in which the downstream end of the syringe housing is coated with, or made from, materials that can remove preservatives and/or fibrils from insulin formulations. In FIG. 58D the overall syringe-type insulin delivery system is generally designated as 380. The system 380 includes a plunger cap 381, a plunger sleeve 382, a syringe housing 383, a syringe chamber 384 and a needle 386. The insulin in the syringe chamber 384 enters the patient's body through the needle 386. At the downstream end of the syringe chamber, a filter, absorbing material, or other component 385 is incorporated in order to remove preservatives and/or fibrils before the insulin enters a patient's body. The use of the filtration system or absorbing material prevents or reduces tissue inflammation, infection and loss of effective insulin delivery using a syringe-type insulin delivery system.

Figure 58E:
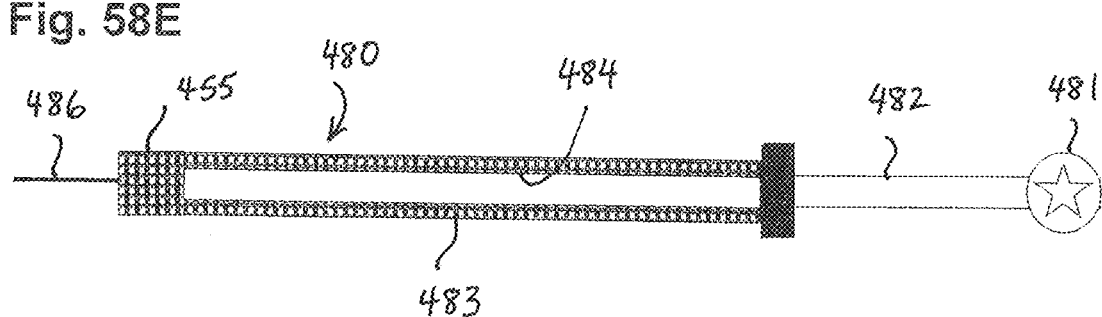

Coated and End-Modified Syringe Chamber—FIG. 58E shows an insulin delivery system that contains a combination of the elements shown in FIGS. 58B and 58D. In FIG. 58E the overall syringe-type insulin delivery system is generally designated as 480. The system 480 includes a plunger cap 481, a plunger sleeve 482, a syringe housing 483, a syringe chamber 484 and a needle 486. The component that removes preservatives and/or fibrils is designated as 485a and 485b.

Figure 58F:
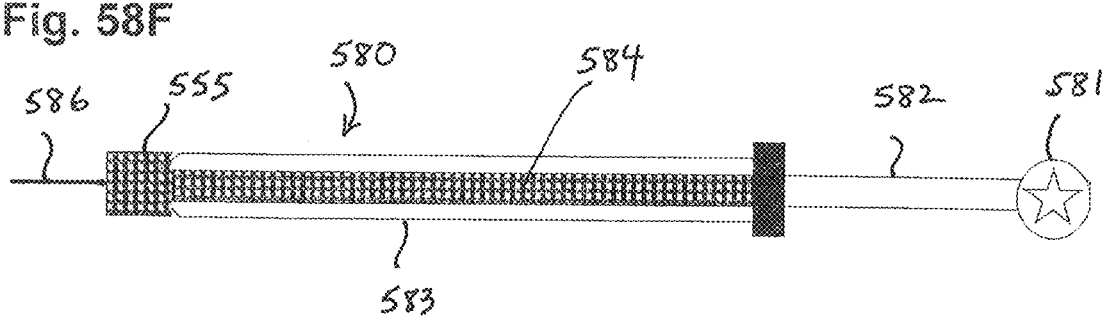

Filled and End-Modified Syringe Chamber—FIG. 58F shows an insulin delivery system that contains a combination of the elements shown in FIGS. 58C and 58D. In FIG. 58F the overall syringe-type insulin delivery system is generally designated as 580. The system 580 includes a plunger cap 581, a plunger sleeve 582, a syringe housing 583, a syringe chamber 584 and a needle 586. The components that remove preservatives and/or fibrils is designated as 585a and 585b.

The embodiments shown in FIGS. 58A-58F can be revised to incorporate drugs, factors, and/or agents in place of, or in addition to, the components that remove preservatives and/or fibrils.

What is claimed is:

1. A method of lowering the concentrations of preservatives in a liquid insulin composition delivered through transdermal insulin pump system, the preservatives including at least one of phenol and m-cresol, the method comprising filtering the liquid insulin composition by incorporating into the insulin pump system a filter comprising a cyclodextrin bead polymer configured to remove phenol and m-cresol without removing insulin.

2. The method of claim 1, wherein the insulin pump system includes an insulin infusion set including an insulin delivery line, and the cyclodextrin is incorporated into a filter disposed in at least one of the insulin delivery line, a cannula, and a housing that can be disposed between the insulin delivery line and the cannula.

3. The method of claim 2, further comprising coating at least one of a cannula and a collar for a cannula in the insulin infusion set with at least one of an extracellular matrix, a gel, an oil and a biological lubricant.

4. The method of claim 1, wherein the cyclodextrin is configured to remove additional anti-microbial agents from the liquid insulin composition.

5. The method of claim 1, further comprising incorporating an agent that suppresses inflammation into an infusion site for the insulin pump system, the agent comprising at least one member selected from the group consisting of corticosteroids, acetylsalicylic acid, and 3-chloro-N-tert-butyl-β-keto-α-methylphenethylamine (buproprion).

6. The method of claim 1, wherein the cyclodextrin is located in inline tubing, in an infusion cap, or in a cannula of the insulin infusion set.

7. The method of claim 1, further comprising including an anti-protease component in the liquid insulin composition, the anti-protease component comprising at least one of aprotinin, alpha-1-antitrypsin (AAT), SP16 serine protease inhibitor, and pepstatin.

8. The method of claim 1, further comprising incorporating [(1R)-3-methyl-1-[[(2S)-3-phenyl-2-(pyrazine-2-carbonylamino)propanoyl] amino]butyl]boronic acid into an infusion site for the insulin pump system.

9. The method of claim 1, further comprising incorporating into an infusion site for the insulin pump system an agent that suppresses insulin degradation, the agent comprising at least one member selected from the group consisting of alpha-2-macroglobulin, alpha-1-antitrypsin, aprotinin and pepstatin.

10. The method of claim 1, further comprising incorporating into an infusion site for the insulin pump system at least one member selected from the group consisting of VEGFa, VEGFc and VEGFd.

11. The method of claim 1, further comprising incorporating into an infusion site for the insulin pump system a chemokine inhibitor comprising at least one member selected from the group consisting of 3,7-dimethyl-1-(5-oxohexyl)purine-2,6-dione, (2R)-2-[4-(2-methylpropyl)phenyl]-N-methylsulfonylpropanamide, (2S)-2-[[(2R)-2-[[(2S)-2-[[(2S)-2-[[(2S)-2-[[(2S)-2-acetamido-5-(diaminomethylideneamino) pentanoyl]amino]-5-(diaminomethylideneamino)pentanoyl]amino]-3-(1H-indol-3-yl)propanoyl]amino]-3-(1H-indol-3-yl)propanoyl]amino]-3-sulfanylpropanoyl]amino]-5-(diaminomethylideneamino)pentanamide, and 2-[(1-benzylindazol-3-yl)methoxy]-2-m ethylpropanoic acid.

12. The method of claim 1, further comprising removing fibrils by incorporating a fibril filtration system into the insulin pump system in order to remove at least one of proteins and protein complexes having a molecular weight between 36 thousand and 50 thousand.

13. The method of claim 1, wherein the insulin pump system comprises a syringe.

14. The method of claim 13, wherein the syringe includes a syringe chamber and the filter is incorporated into the syringe chamber.

15. The method of claim 1, wherein the insulin pump system comprises a needle and a plunger system and the filter is associated with the plunger system.

* * * * *